US012781227B2

(12) United States Patent
Rawlings et al.

(10) Patent No.: US 12,781,227 B2
(45) Date of Patent: Nov. 3, 2026

(54) TALEN-BASED AND CRISPR/Cas-BASED GENE EDITING FOR BRUTON'S TYROSINE KINASE

(71) Applicant: Seattle Children's Hospital, Seattle, WA (US)

(72) Inventors: David J. Rawlings, Seattle, WA (US); Courtnee Clough, Edmonds, WA (US); Iram F. Khan, Issaquah, WA (US)

(73) Assignee: Seattle Children's Hospital, Seattle, WA (US)

( * ) Notice: Subject to any disclaimer, the term of this patent is extended or adjusted under 35 U.S.C. 154(b) by 1021 days.

(21) Appl. No.: 17/050,794

(22) PCT Filed: Apr. 26, 2019

(86) PCT No.: PCT/US2019/029417
§ 371 (c)(1),
(2) Date: Oct. 26, 2020

(87) PCT Pub. No.: WO2019/210216
PCT Pub. Date: Oct. 31, 2019

(65) Prior Publication Data

US 2022/0064651 A1 Mar. 3, 2022

Related U.S. Application Data

(60) Provisional application No. 62/664,035, filed on Apr. 27, 2018.

(51) Int. Cl.

| | |
|---|---|
| ***C12N 15/113*** | (2010.01) |
| ***C07K 14/47*** | (2006.01) |
| ***C12N 9/22*** | (2006.01) |
| ***C12N 15/11*** | (2006.01) |
| ***C12N 15/86*** | (2006.01) |

(52) U.S. Cl.
CPC .......... *C12N 15/1137* (2013.01); *C07K 14/47* (2013.01); *C12N 9/22* (2013.01); *C12N 15/111* (2013.01); *C12N 15/86* (2013.01); *C12N 2310/20* (2017.05)

(58) Field of Classification Search
CPC ...... C12N 15/1137; C12N 9/22; C12N 15/86; C12N 2310/20
See application file for complete search history.

(56) References Cited

U.S. PATENT DOCUMENTS

| | | | | |
|---|---|---|---|---|
| 8,614,092 | B2 | 12/2013 | Zhang et al. | |
| 8,771,945 | B1 * | 7/2014 | Zhang .................. | C12N 15/902 435/320.1 |
| 9,017,967 | B2 | 4/2015 | Bonas et al. | |
| 10,188,749 | B2 | 1/2019 | Stephan et al. | |
| 2014/0234975 | A1 | 8/2014 | Silva et al. | |
| 2014/0335063 | A1 | 11/2014 | Cannon et al. | |
| 2016/0002671 | A1 | 1/2016 | Smith et al. | |
| 2021/0230565 | A1 | 7/2021 | Rawlings et al. | |
| 2022/0364123 | A1 | 11/2022 | Gay et al. | |

FOREIGN PATENT DOCUMENTS

| | | | |
|---|---|---|---|
| WO | WO-2012007848 | A2 | 1/2012 |
| WO | WO-2013009525 | A1 | 1/2013 |
| WO | WO-2013126794 | A1 | 8/2013 |
| WO | WO-2014167494 | A1 | 10/2014 |
| WO | WO-2014199358 | A1 | 12/2014 |
| WO | WO-2015071474 | A2 | 5/2015 |
| WO | WO-2015161276 | A2 | 10/2015 |
| WO | WO-2017156484 | A1 | 9/2017 |
| WO | WO-2017177137 | A1 | 10/2017 |
| WO | WO-2018022619 | A1 | 2/2018 |
| WO | WO-2019210213 | A1 | 10/2019 |
| WO | WO-2019210216 | A2 | 10/2019 |
| WO | WO-2020219845 | A1 | 10/2020 |

OTHER PUBLICATIONS

Clough, Courtnee, et al. "132. Targeting the BTK locus in primary human hematopoietic cells with TALENs and AAV donor template." Molecular Therapy 24: S54. (Year: 2016).*
Kim, Ekaterina, et al. "Ibrutinib inhibits pre-BCR+ B-cell acute lymphoblastic leukemia progression by targeting BTK and BLK." Blood, The Journal of the American Society of Hematology 129.9 (2017): 1155-1165. (Year: 2017).*
Kohn, Donald B., and Caroline Y. Kuo. "New frontiers in the therapy of primary immunodeficiency: from gene addition to gene editing." Journal of Allergy and Clinical Immunology 139.3 (2017): 726-732. (Year: 2017).*
NIH NCBI. *Homo sapiens* Bruton tyrosine kinase (BTK), transcript variant 1, mRNA. NCBI Reference Sequence: NM_000061.2 (Year: 2008).*
Clough, Courtnee, et al. "132. Targeting the BTK locus in primary human hematopoietic cells with TALENs and AAV donor template." Molecular Therapy 24 (2016): S54. (Year: 2016).*
Mohr, Stephanie E., et al. "CRISPR guide RNA design for research applications." The FEBS journal 283.17 (2016): 3232-3238. (Year: 2016).*
Zhang, Jian-Hua, et al. "Optimization of genome editing through CRISPR-Cas9 engineering." Bioengineered 7.3 (2016): 166-174. (Year: 2016).*
Chylinski, The tracrRNA and Cas9 families of type II CRISPR-Cas immunity systems, RNA biology, May 2013, pp. 726-737.
Database GenBank Accession No. AK057105 "*Homo sapiens* cDNA FLJ32543 fis, clone SMINT2000538, highly similar to Tyrosine-protein kinase BTK (EC 2.7.10.2)", Jul. 3, 2008, 3 pages.

(Continued)

*Primary Examiner* — Teresa E Knight
*Assistant Examiner* — Michael Angelo Riga
(74) *Attorney, Agent, or Firm* — COOLEY LLP

(57) ABSTRACT

The present disclosure provides improved genome editing compositions and methods for editing a human BTK gene. The disclosure further provides genome edited cells for the prevention, treatment, or amelioration of at least one symptom of X-linked agammaglobulinemia (XLA).

8 Claims, 27 Drawing Sheets

Specification includes a Sequence Listing.

(56) References Cited

OTHER PUBLICATIONS

Database GenBank Accession No. BC109079, "*Homo sapiens* Bruton agammaglobulinemia tyrosine kinase, mRNA (cDNA clone MGC:126261 IMAGE:40034287), complete eds", Oct. 4, 2006, 3 pages.
Database GenBank Accession No. BI910072, "603067905F1 NIH_ MGC_ 118 *Homo sapiens* cDNA clone IMAGE:5217096 5', mRNA sequence", Oct. 16, 2001, 2 pages.
Database GenBank Accession No. CF529565, "UI-1-BC1p-asu-f-09-0-UI.s1 NCI_CGAP_PI3 *Homo sapiens* cDNA clone UI-1-BC1p-asu-f-09-0-UI 3', mRNA sequence", Jan. 6, 2011, 2 pages.
Database GenBank Accession No. DA619542, "DA619542 JCMLC2 *Homo sapiens* cDNA clone JCMLC2000455 5', mRNA sequence", Feb. 20, 2011, 2 pages.
Database GenBank Accession No. DB636737, "DB636737 Riken full-length enriched human cDNA library, hippocampus *Homo sapiens* cDNA clone H023059J10 3', mRNA sequence", Jul. 12, 2006, 2 pages.
Database GenBank Accession No. NG_007877.1, "*Homo sapiens* WASP actin nucleation promoting factor (WAS), RefSeqGene (LRG_ 125) on chromosome X", Jun. 1, 2023, 7 pages.
Database GenBank Asccesion No. U19927 "Human Wiskott-Aldrich syndrome (WAS) mRNA, complete cds", Jun. 8, 1995, 2 pages.
Database Geneseq [Online] Jun. 14, 2018 (Jun. 14, 2018), "Ophiostoma novo-ulmi I-Onul LHE variant protein TGFBR2.B3 Seq Id No: 63.", retrieved from EBI accession No. GSP:BFF71128, Database accession No. BFF71128, 1 page.
Database Geneseq [Online] Jan. 15, 2015 (Jan. 15, 2015), "Ophiostoma novo-ulmi mutant I-Onul protein LHE CCR5_S02_1 F5, Seq Id 10.", retrieved from EBI accession No. GSP:BBQ87913 Database accession No. BBQ87913, 1 page.
Database NCBI Accession No. NP_000368.1, "actin nucleation-promoting factor WAS [*Homo sapiens*]", May 29, 2023, 4 pages.
Database NCBI Reference Sequence: NC_000023.11, "*Homo sapiens* chromosome X, GRCh38.p14 Primary Assembly", Mar. 20, 2023, 3 pages.
Database NCBI Reference Sequence: NM_000377.2, "*Homo sapiens* WASP actin nucleation promoting factor (WAS), mRNA", Aug. 4, 2019, 5 pages.
Database NCBI Reference Sequence: NM_001287344.1, "*Homo sapiens* Bruton tyrosine kinase (BTK), transcript variant 3, mRNA", May 24, 2020, 5 pages.
Database NCBI Reference Sequence: NM_001287345.1, "*Homo sapiens* Bruton tyrosine kinase (BTK), transcript variant 2, mRNA", May 24, 2020, 6 pages.
Database NCBI Reference Sequence NP_000052.1, "tyrosine-protein kinase BTK isoform 1 [*Homo sapiens*]", Jul. 26, 2023, 5 pages.
Database NCBI Reference Sequence: NP_001274273.1, "tyrosine-protein kinase BTK isoform 3 [*Homo sapiens*]", Jul. 26, 2023, 4 pages.
Database NCBI Reference Sequence: NP_001274274.1, "tyrosine-protein kinase BTK isoform 2 [*Homo sapiens*]", Jul. 26, 2023, 4 pages.
Database NCBI Reference Sequence: XM_017029786.1, "Predicted: *Homo sapiens* WASP actin nucleation promoting factor (WAS), transcript variant X2, mRNA", Nov. 22, 2021, 2 pages.
Database NCBI Reference Sequence: XP_011542279.1, "actin nucleation-promoting factor WAS isoform X4 [*Homo sapiens*]", Mar. 20, 2023, 2 pages.
Database NCBI Reference Sequence: XP_016885275.1, "actin nucleation-promoting factor WAS isoform X1 [*Homo sapiens*]", Mar. 20, 2023, 2 pages.
Database UniProt Accession No. Q06187 "Agammaglobulinemia tyrosine kinase", created Jun. 1, 1994, 28 pages.
Database UniProt Accession No. Q5JY90, "Bruton agammaglobulinemia tyrosine kinase", created Feb. 15, 2005, 2 pages.
Database UniProt Accession No. Q9BU11, "RecName: Full=Actin nucleation-promoting factor WAS; AltName: Full=Wiskott-Aldrich syndrome protein; Short=WASp", created Nov. 1, 1995, 13 pages.
Database UniProt No. A0A024QYX8, "Wiskott-Aldrich syndrome (Eczema-thrombocytopenia), isoform", Jul. 2014, 3 pages.
Database UniProtKB Accession No. Q9UNJ9, "RecName: Full= Actin nucleation-promoting factor WAS; AltName: Full=Wiskott-Aldrich syndrome protein; Short=WASp", created Nov. 1, 1995, 13 pages.
Database UniProtKB Accession: P42768, "Rec Name: Full=Actin nucleation-promoting factor WAS; Alt Name: Full=Wiskott-Aldrich syndrome protein; Short=WASp", created Nov. 1, 1995, 13 pages.
Database Vega Id No. OTTHUMT00000057532, "Bruton agammaglobulinemia tyrosine kinase", available at: https://vega.archive.ensembl.org/Homo_sapiens/Transcript/ProteinSummary?g=OTTHUMG00000022022;r=X:101349450-101386195;t=OTTHUMT00000057532. Vega Genome Browser release 68—Feb. 2017. 1 printed page.
Database Vega, Transcript: BTK-006: OTTHUMP00000023676, "Bruton agammaglobulinemia tyrosine kinase", available at: https://vega.archive.ensembl.org/Homo_sapiens/Transcript/ProteinSummary?g=OTTHUMG00000022022;r=X:101349450-101386195;t=OTTHUMT00000057532, Vega Genome Browser release 68—Feb. 2017, first seen Aug. 15, 2005. 1 printed page.
Deveau et al., "Phage response to CRISPR-encoded resistance in *Streptococcus thermophilus*", J Bacteriol. Feb. 2008; 190(4): 1390-400. Epub Dec. 7, 2007. 11 pages.
Ensmbl Database archived ID: ENSP00000410537, Ensembl release 95—Jan. 2019, 2 printed pages.
Ensmbl Database, Protein domains for ENSP00000308176.7, "Bruton tyrosine kinase", available online at: http://jan2019.archive.ensembl.org/Homo_sapiens/Transcript/ProteinSummary?g=ENSG00000010671;r=X:101349450-101386195;t=ENST00000308731, Ensembl release 95—Jan. 2019. Retrieved Jan. 16, 2024. 2 pages.
Ensmbl Database Transcript: BTK-201 ENST00000308731.7, "Bruton tyrosine kinase", available at http://jan2019.archive.ensembl.org/Homo_sapiens/Transcript/ProteinSummary?g=ENSG00000010671;r=X:101349450-101386195;t=ENST00000308731, Ensembl release 95—Jan. 2019. Retrieved Jan. 16, 2024. 2 pages.
Ensmbl Database, Archived ID No. ENSP00000365891, "Wiskott-Aldrich Syndrome", Ensemble release 95—Jan. 2019, first seen Apr. 3, 2006. Retrieved Jan. 16, 2024. 1 printed page.
Ensmbl Database No. ENSG00000015285 "WASP actin nucleation promoting factor", EMBL-EBI, European Bioinformatics Institute, Ensemble release 95 Jan. 2019. Available at: http://jan2019.archive.ensembl.org/Homo_sapiens/Gene/Summary?db=core;g=ENSG00000015285;r=X:48676596-48691427. Retrieved Jan. 30, 2024, 2 printed pages.
Esvelt, K., et al., "A system for the continuous directed evolution of biomolecules", Nature. Apr. 28, 2011; 472(7344): 499-503. Epub Apr. 10, 2011.
Esvelt, K., et al., "Orthogonal Cas9 proteins for RNA-guided gene regulation and editing", Nat Methods. Nov. 2013; 10(11): 1116-21. Epub Sep. 29, 2013.
Extended European Search Report for EP Application No. 19793918.4, dated Jan. 10, 2002. 10 pages.
Guilinger, J. P., et al., "Broad specificity profiling of TALENs results in engineered nucleases with improved DNA-cleavage specificity," Nat Methods. Apr. 2014; 11(4): 429-35. Epub Feb. 16, 2014.
Gutierrez-Guerrero et al., "Comparison of Zinc Finger Nucleases Versus CRISPR-Specific Nucleases for Genome Editing of the Wiskott-Aldrich Syndrome Locus", Hum Gene Ther. Mar. 2018; 29(3): 366-380. Epub Oct. 25, 2017.
Horvath et al., "CRISPR/Cas, the Immune System of Bacteria and Archaea", Science. Jan. 8, 2010; 327(5962): 167-70.
Hou et al., "Efficient genome engineering in human pluripotent stem cells using Cas9 from Neisseria meningitidis", Proc Natl Acad Sci USA. Sep. 24, 2013; 110(39): 15644-9. Epub Aug. 12, 2013. 6 pages.
Ikegame et al., "Allogeneic stem cell transplantation for X-linked agammaglobulinemia using reduced intensity conditioning as a

(56) References Cited

OTHER PUBLICATIONS model of the reconstitution of humoral immunity", J Hematol Oncol. Feb. 13, 2016; 9: 9. 9 pages.
International Preliminary Report on Patentability for International Application No. PCT/US2019/029414, mailed Nov. 5, 2020, 6 pages.
International Preliminary Report on Patentability for International Application No. PCT/US2019/029417, issued Oct. 27, 2020, 8 pages.
International Preliminary Report on Patentability for International Application No. PCT/US2020/029771, mailed Nov. 4, 2021, 8 pages.
International Search Report and Written Opinion for International Application No. PCT/US2019/029414, mailed Jul. 10, 2019, 9 pages.
International Search Report and Written Opinion for International Application No. PCT/US2019/029417, mailed Nov. 1, 2019, 14 pages.
International Search Report and Written Opinion for International Application No. PCT/US2020/029771, mailed Sep. 30, 2020, 12 pages.
Invitation to Pay Additional Fees received for International Application No. PCT/US2019/029417, mailed Aug. 1, 2019, 3 pages.
Invitation to Pay Additional Fees received for International Application No. PCT/US2020/029771, mailed Aug. 4, 2020, 2 pages.
Jarjour et al., "High-resolution profiling of homing endonuclease binding and catalytic specificity using yeast surface display", Nucleic Acids Res. Nov. 2009; 37(20): 6871-80. Epub Sep. 8, 2009.
Joung & Sander, "TALENs: a widely applicable technology for targeted genome editing," Nat Rev Mol Cell Biol. Jan. 2013; 14(1): 49-55. Epub Nov. 21, 2012.
Juillerat et al., "Optimized tuning of TALEN specificity using non-conventional RVDs." Scientific Reports 5(2015): 8150. 7 pages.
Khan Iram F et al: "Precision Editing of the WAS Locus via Homologous Recombination in Primary Human Hematopoietic Cells Mediated by Either TALEN or CRISPR/Cas Nucleases", Molecular Therapy, Targeted Genome Editing III, vol. 24, Supplement 1, S227, May 2016, 1 page.
Lambert et al., "Indirect DNA Sequence Recognition and Its Impact on Nuclease Cleavage Activity", Structure. Jun. 7, 2016; 24(6): 862-73. Epub Apr. 28, 2016.
Mali et al., "RNA-guided human genome engineering via Cas9", Science. Feb. 15, 2013; 339(6121): 823-6. Epub Jan. 3, 2013.
NCBI CCDS Datbase ID: CCDS14303.1, retrieved from https://www.ncbi.nlm.nih.gov/CCDS/CcdsBrowse.cgi?REQUEST=CCDS&GO=MainBrowse&DATA=CCDS14303.1, retrieved Aug. 31, 2023, 2 pages.
NCBI CCDS Datbase Id: CCDS14482.1 retreived from https://www.ncbi.nlm.nih.gov/CCDS/CcdsBrowse.cgi?REQUEST=CCDS&DATA=CCDS14482.1+&ORGANISM=0&BUILDS=CURRENTBUILDS, retrieved Aug. 31, 2023, 2 pages.
NCBI Reference Sequence: NM_000061.2, "*Homo sapiens* Bruton tyrosine kinase (BTK), transcript variant 1, mRNA", Sep. 21, 2019, 8 pages.
NCBI Reference Sequence: XM_011543977.2, "Predicted: *Homo sapiens* WASP actin nucleation promoting factor (WAS), transcript variant X1, mRNA", Nov. 22, 2021, 2 pages.
Supplementary European Search Report for EP Application No. 19793680.0, dated Mar. 22, 2022, 10 pages.
Supplementary European Search Report for EP Application No. 20796397.6, mailed May 17, 2023, 12 pages.
Supplementary Partial European Search Report for EP Application No. 19793680.0, dated Dec. 22, 2021, 12 pages.
Takeuchi et al., "Tapping natural reservoirs of homing endonucleases for targeted gene modification", Proc Natl Acad Sci USA. Aug. 9, 2011; 108(32): 13077-82. Epub Jul. 22, 2011.
Transcript: WAS-007 (ENST00000376701) "Wiskott-Aldrich syndrome protein" (WASp) [Source:UniProtKB/Swiss-Prot;Acc:P42768], Archive EnsEMBL release 54—May 2009. 1 printed page.
Tsukada et al., "Role of Bruton's tyrosine kinase in immunodeficiency", Curr Opin Immunol. Aug. 1994; 6(4): 623-30.
Wang et al., "Engineering an XID-Site Specific I-Anil Homing Endonuclease through Combination of Rational Design and Directed Evolution", Molecular Therapy, Gene Regulation and Animal Models, vol. 21, Supplement 1, S122-S123, May 2013, 2 pages.
Wang et al. "Progressive engineering of a homing endonuclease genome editing reagent for the murine X-linked immunodeficiency locus" Nucleic Acids Res. Jun. 2014; 42(10): 6463-75. Epub Mar. 25, 2014.
Wang Yupeng et al: "Engineering a WAS-Targeted megaTAL for High Efficiency Homology-Directed Repair (HDR)", Molecular Therapy, vol. 27, No. 4, Suppl. 1, Apr. 22, 2019, p. 397.
Wei et al., "Preclinical investigation of ibrutinib, a Bruton's kinase tyrosine (Btk) inhibitor, in suppressing glioma tumorigenesis and stem cell phenotypes", Oncotarget. Oct. 25, 2016; 7(43): 69961-69975.
Yamamoto et al., "BTK gene targeting by homologous recombination using a helper-dependent adenovirus/adeno-associated virus hybrid vector", Gene Ther. Feb. 2016; 23(2): 205-13. Epub Aug. 17, 2015.
Zhang, et al., Comparison of non-canonical PAMs for CRISPR/Cas9-mediated DNA cleavage in human cells, Scientific reports, Jun. 2014, 5 pages.
Leenay R T, et al., "Deciphering, Communicating, and Engineering the CRISPR RAM," Journal of Molecular Biology, Jan. 20, 2017, vol. 429(2), pp. 177-191.
Office Action for Japanese Application No. 2020-560207 mailed Dec. 2, 2024. With machine translation, 7 pages.
Kawai, Yasuhiro, "[Current and Future Study of Genome Editing Tools]," Department of Experimental Animal Research, National Institute of Infectious Diseases, Tokyo, The Journal of Animal Genetics, 2016, vol. 44, No. 1-2, p. 23-34. Document in Japanese.

* cited by examiner

SEQUENCE LISTING

```
<160> NUMBER OF SEQ ID NOS: 74

<210> SEQ ID NO 1
<211> LENGTH: 17
<212> TYPE: DNA
<213> ORGANISM: Homo sapiens

<400> SEQUENCE: 1

tctcgactat gaaaact                                          17


<210> SEQ ID NO 2
<211> LENGTH: 16
<212> TYPE: DNA
<213> ORGANISM: Homo sapiens

<400> SEQUENCE: 2

tctaaggcca agtcct                                           16


<210> SEQ ID NO 3
<211> LENGTH: 17
<212> TYPE: DNA
<213> ORGANISM: Homo sapiens

<400> SEQUENCE: 3

tatcaaggac ttggcct                                          17


<210> SEQ ID NO 4
<211> LENGTH: 19
<212> TYPE: DNA
<213> ORGANISM: Homo sapiens

<400> SEQUENCE: 4

taccaacgaa aatttacct                                        19


<210> SEQ ID NO 5
<211> LENGTH: 19
<212> TYPE: DNA
<213> ORGANISM: Homo sapiens

<400> SEQUENCE: 5

tatttcctag cctataact                                        19


<210> SEQ ID NO 6
<211> LENGTH: 18
<212> TYPE: DNA
<213> ORGANISM: Homo sapiens

<400> SEQUENCE: 6

tggcttctta ggaccttt                                         18
```

<210> SEQ ID NO 7
<211> LENGTH: 16
<212> TYPE: DNA
<213> ORGANISM: Homo sapiens

<400> SEQUENCE: 7
ccatttgaaa ctaggt 16

<210> SEQ ID NO 8
<211> LENGTH: 17
<212> TYPE: DNA
<213> ORGANISM: Homo sapiens

<400> SEQUENCE: 8
cctcatccct cttggtt 17

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
agctatggcc gcagtgattc 20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
aggcgcttct tgaagtttag 20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
atgagtatga ctttgaacgt 20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
agggatgagg attaatgtcc 20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
acactgaatt gggggggat 20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
aactaggtag ctaggctgag 20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
gctttagcta gttataggct 20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
agaggtaaat tttcgttggt 20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
gatgcacact gaattggggg 20

<210> SEQ ID NO 18
<211> LENGTH: 659
<212> TYPE: PRT
<213> ORGANISM: Homo sapiens

<400> SEQUENCE: 18

Met Ala Ala Val Ile Leu Glu Ser Ile Phe Leu Lys Arg Ser Gln Gln
1 5 10 15

Lys Lys Lys Thr Ser Pro Leu Asn Phe Lys Lys Arg Leu Phe Leu Leu
20 25 30

Thr Val His Lys Leu Ser Tyr Tyr Glu Tyr Asp Phe Glu Arg Gly Arg
35 40 45

Arg Gly Ser Lys Lys Gly Ser Ile Asp Val Glu Lys Ile Thr Cys Val
50 55 60

Glu Thr Val Val Pro Glu Lys Asn Pro Pro Pro Glu Arg Gln Ile Pro
65 70 75 80

Arg Arg Gly Glu Glu Ser Ser Glu Met Glu Gln Ile Ser Ile Ile Glu
85 90 95

Arg Phe Pro Tyr Pro Phe Gln Val Val Tyr Asp Glu Gly Pro Leu Tyr
100 105 110

Val Phe Ser Pro Thr Glu Glu Leu Arg Lys Arg Trp Ile His Gln Leu

```
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
        435                 440                 445

Met Met Asn Leu Ser His Glu Lys Leu Val Gln Leu Tyr Gly Val Cys
    450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe Gly Leu Ser Arg
    530                 535                 540
```

Tyr Val Leu Asp Asp Glu Tyr Thr Ser Ser Val Gly Ser Lys Phe Pro
545 550 555 560

Val Arg Trp Ser Pro Pro Glu Val Leu Met Tyr Ser Lys Phe Ser Ser
565 570 575

Lys Ser Asp Ile Trp Ala Phe Gly Val Leu Met Trp Glu Ile Tyr Ser
580 585 590

Leu Gly Lys Met Pro Tyr Glu Arg Phe Thr Asn Ser Glu Thr Ala Glu
595 600 605

His Ile Ala Gln Gly Leu Arg Leu Tyr Arg Pro His Leu Ala Ser Glu
610 615 620

Lys Val Tyr Thr Ile Met Tyr Ser Cys Trp His Glu Lys Ala Asp Glu
625 630 635 640

Arg Pro Thr Phe Lys Ile Leu Leu Ser Asn Ile Leu Asp Val Met Asp
645 650 655

Glu Glu Ser

<210> SEQ ID NO 19
<211> LENGTH: 7209
<212> TYPE: DNA
<213> ORGANISM: Artificial Sequence
<220> FEATURE:
<223> OTHER INFORMATION: Synthetic construct - AAV targeting vector

<400> SEQUENCE: 19
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtggga 180
actttatttg tctttctgtg tttcagttac ctaaattgaa tccttctgga gtattgtagg 240
tttggggagg ctaaataagt tgtgtttcat aaatgaacag aggtggcatc tatatcagta 300
agacagttgc atcacttttg catgatgctg tctaaaagaa ctaatttaag ctaaatgggg 360
aaaaggtcag aaaacaacaa ctaccccccc cccaccaaaa cccaccaaaa aaaattatgt 420
tttcaacttt agaacaaatc ttctatcctt tgtagctcag tcagtgggtg tgggcaaaat 480
cagttgggca gcagttagtg tgtgtccaga actgcaggtg cagcctccat atccttatta 540
gttcccttgg ttacagaccc cagtgggaca atgtttgaaa aattatattc accgtctagg 600
aaattgggaa ctgaaagtcc aatatctgcc tcagtggagt tctggcacct gcattatccc 660
ttctgggtat atcaagatca acagctgcac agatactttt gcttttcaca gattctacac 720
atatcatata aaggtgaata gtgtaaagct acctctacac cttaccaagc acacaggtgc 780
gtgccattta acatctagag cattccattg ccttatacaa gaactcagtt tatatgagct 840
cacaacatcg aaccaatccc cccccaattc agtgtgcatc cattatacct gaaacctgac 900
agagctgggg gctgtgggag gaggttggta ggaagaaatt attttgtgag ctgtgcacat 960
ttttgttcca tttgaaacta ggtagctagg ctgagggggga accaagaggg atgaggatta 1020
atgtcctggg tcctcaggaa ctttcattat caacagcaca caggtgaact ccagaaagaa 1080
gaagctatgg ccgcagtgat tctggagagc atctttctga agcgatcccg aacagagaaa 1140
caggagaata tgggccaaac aggatatctg tggtaagcag ttcctgcccc ggctcagggc 1200
caagaacagt tggaacagca gaatatgggc caaacaggat atctgtggta agcagttcct 1260
gccccggctc agggccaaga acagatggtc cccagatgcg gtcccgccct cagcagtttc 1320
tagagaacca tcagatgttt ccagggtgcc ccaaggacct gaaatgaccc tgtgccttat 1380

```
ttgaactaac caatcagttc gcttctcgct tctgttcgcg cgcttctgct ccccgagctc   1440
tatataagca gagctcgttt agtgaaccgt cagatcgcct ggagacgcca tccacgctgt   1500
tttgacttcc atagaaggat ctcgaggcca ccatggtgag caagggcgag gagctgttca   1560
ccggggtggt gcccatcctg gtcgagctgg acggcgacgt aaacggccac aagttcagcg   1620
tgtccggcga gggcgagggc gatgccacct acggcaagct gaccctgaag ttcatctgca   1680
ccaccggcaa gctgcccgtg ccctggccca ccctcgtgac caccctgacc tacggcgtgc   1740
agtgcttcag ccgctacccc gaccacatga agcagcacga cttcttcaag tccgccatgc   1800
ccgaaggcta cgtccaggag cgcaccatct tcttcaagga cgacggcaac tacaagaccc   1860
gcgccgaggt gaagttcgag ggcgacaccc tggtgaaccg catcgagctg aagggcatcg   1920
acttcaagga ggacggcaac atcctggggc acaagctgga gtacaactac aacagccaca   1980
acgtctatat catggccgac aagcagaaga acggcatcaa ggtgaacttc aagatccgcc   2040
acaacatcga ggacggcagc gtgcagctcg ccgaccacta ccagcagaac acccccatcg   2100
gcgacggccc cgtgctgctg cccgacaacc actacctgag cacccagtcc gccctgagca   2160
aagaccccaa cgagaagcgc gatcacatgg tcctgctgga gttcgtgacc gccgccggga   2220
tcactctcgg catggacgag ctgtacaagt aaactagtgt cgactgcttt atttgtgaaa   2280
tttgtgatgc tattgcttta tttgtaacca ttataagctg caataaacaa gttaacaaca   2340
acaattgcat tcattttatg tttcaggttc agggggaggt gtgggaggtt ttttaaaaac   2400
agaaaaagaa aacatcacct ctaaacttca agaagcgcct gtttctcttg accgtgcaca   2460
aactctccta ctatgagtat gactttgaac gtggggtaag tttctcgact atgaaaactg   2520
agtttcaaga tatcaaggac ttggccttag atctttcttg gggaagaggt aaattttcgt   2580
tggtaggagg aggggagtag aatggaccta agttctttca aattcagcaa aatatttcct   2640
agcctataac tagctaaagc cggaaagtca aaggtcctaa gaagccacaa ggaaaatatt   2700
accatggaat cttggaattg atgagcactc attaaatgat tgttgaaaat gaaatcgaag   2760
agttggaaat tgcttcctta cttcctatga ggaaggtaca tacagtcatt cactcttcca   2820
tggtatttgc cctccatttg gtagtcatag atttatagat ctggaaggat tttttttct    2880
tcccccacat gacaggtcct ggtgccacct cactttgttg aatgattaga taacaaaatc   2940
taatcatctg gttgcttaat ccctcttaat ctttctccat tttcttcctc attctacttc   3000
tcagagaaga ggcagtaaga agggttcaat agatgttgag aagatcactt gtgttgaaac   3060
agtggttcct gaaaaaaatc ctcctccaga aagacagatt ccggtaagaa gagaccaatg   3120
tctgagatgg ggaacagcag atttgaagaa atttgcaaca tttaaattct ctgtaaatag   3180
actggtgatg ctgtgcaacg tggaacacgg tcaagtttcc tttaaaaatt cttcactcta   3240
ccatattggt tataaagaat cttagcttct ttccttcata ttcagaacat ctcactaaac   3300
atggaaaatt tgttaacaca aactttttaaa tgatgctata tctagttttc aaactggtca  3360
gagatcattg attttattcc ctcagttctc tcaggatcag atttagaggc ttaagtaagt   3420
ctgaatgtca taatcctagg gctctgctct agagtagata agtagcatgg cgggttaatc   3480
attaactaca aggaacccct agtgatggag ttggccactc cctctctgcg cgctcgctcg   3540
ctcactgagg ccgggcgacc aaaggtcgcc cgacgcccgg gctttgcccg ggcggcctca   3600
gtgagcgagc gagcgcgcca gctggcgtaa tagcgaagag gcccgcaccg atcgcccttc   3660
ccaacagttg cgcagcctga atggcgaatg gcgattccgt tgcaatggct ggcggtaata   3720
```

```
ttgttctgga tattaccagc aaggccgata gtttgagttc ttctactcag gcaagtgatg   3780
ttattactaa tcaaagaagt attgcgacaa cggttaattt gcgtgatgga cagactcttt   3840
tactcggtgg cctcactgat tataaaaaca cttctcagga ttctggcgta ccgttcctgt   3900
ctaaaatccc tttaatcggc ctcctgttta gctcccgctc tgattctaac gaggaaagca   3960
cgttatacgt gctcgtcaaa gcaaccatag tacgcgccct gtagcggcgc attaagcgcg   4020
gcgggtgtgg tggttacgcg cagcgtgacc gctacacttg ccagcgccct agcgcccgct   4080
cctttcgctt tcttcccttc ctttctcgcc acgttcgccg gctttccccg tcaagctcta   4140
aatcgggggc tccctttagg gttccgattt agtgctttac ggcacctcga ccccaaaaaa   4200
cttgattagg gtgatggttc acgtagtggg ccatcgccct gatagacggt ttttcgccct   4260
ttgacgttgg agtccacgtt ctttaatagt ggactcttgt tccaaactgg aacaacactc   4320
aaccctatct cggtctattc ttttgattta taagggattt tgccgatttc ggcctattgg   4380
ttaaaaaatg agctgattta acaaaaattt aacgcgaatt ttaacaaaat attaacgttt   4440
acaatttaaa tatttgctta tacaatcttc ctgtttttgg ggcttttctg attatcaacc   4500
ggggtacata tgattgacat gctagtttta cgattaccgt tcatcgattc tcttgtttgc   4560
tccagactct caggcaatga cctgatagcc tttgtagaga cctctcaaaa atagctaccc   4620
tctccggcat gaatttatca gctagaacgg ttgaatatca tattgatggt gatttgactg   4680
tctccggcct ttctcacccg tttgaatctt tacctacaca ttactcaggc attgcattta   4740
aaatatatga gggttctaaa aatttttatc cttgcgttga aataaaggct tctcccgcaa   4800
aagtattaca gggtcataat gtttttggta caaccgattt agctttatgc tctgaggctt   4860
tattgcttaa ttttgctaat tctttgcctt gcctgtatga tttattggat gttggaatcg   4920
cctgatgcgg tattttctcc ttacgcatct gtgcggtatt tcacaccgca tatggtgcac   4980
tctcagtaca atctgctctg atgccgcata gttaagccag ccccgacacc cgccaacacc   5040
cgctgacgcg ccctgacggg cttgtctgct cccggcatcc gcttacagac aagctgtgac   5100
cgtctccggg agctgcatgt gtcagaggtt ttcaccgtca tcaccgaaac gcgcgagacg   5160
aaagggcctc gtgatacgcc tatttttata ggttaatgtc atgataataa tggtttctta   5220
gacgtcaggt ggcacttttc ggggaaatgt gcgcggaacc cctatttgtt tatttttcta   5280
aatacattca aatatgtatc cgctcatgag acaataaccc tgataaatgc ttcaataata   5340
ttgaaaaagg aagagtatga gtattcaaca tttccgtgtc gcccttattc ccttttttgc   5400
ggcattttgc cttcctgttt ttgctcaccc agaaacgctg gtgaaagtaa aagatgctga   5460
agatcagttg ggtgcacgag tgggttacat cgaactggat ctcaacagcg gtaagatcct   5520
tgagagtttt cgccccgaag aacgttttcc aatgatgagc acttttaaag ttctgctatg   5580
tggcgcggta ttatcccgta ttgacgccgg gcaagagcaa ctcggtcgcc gcatacacta   5640
ttctcagaat gacttggttg agtactcacc agtcacagaa aagcatctta cggatggcat   5700
gacagtaaga gaattatgca gtgctgccat aaccatgagt gataacactg cggccaactt   5760
acttctgaca acgatcggag gaccgaagga gctaaccgct tttttgcaca acatggggga   5820
tcatgtaact cgccttgatc gttgggaacc ggagctgaat gaagccatac caaacgacga   5880
gcgtgacacc acgatgcctg tagcaatggc aacaacgttg cgcaaactat taactggcga   5940
actacttact ctagcttccc ggcaacaatt aatagactgg atggaggcgg ataaagttgc   6000
aggaccactt ctgcgctcgg cccttccggc tggctggttt attgctgata aatctggagc   6060
cggtgagcgt gggtctcgcg gtatcattgc agcactgggg ccagatggta agccctcccg   6120
```

```
tatcgtagtt atctacacga cggggagtca ggcaactatg gatgaacgaa atagacagat   6180
cgctgagata ggtgcctcac tgattaagca ttggtaactg tcagaccaag tttactcata   6240
tatactttag attgatttaa aacttcattt ttaatttaaa aggatctagg tgaagatcct   6300
ttttgataat ctcatgacca aaatccctta acgtgagttt tcgttccact gagcgtcaga   6360
ccccgtagaa aagatcaaag gatcttcttg agatcctttt tttctgcgcg taatctgctg   6420
cttgcaaaca aaaaaaccac cgctaccagc ggtggtttgt ttgccggatc aagagctacc   6480
aactcttttt ccgaaggtaa ctggcttcag cagagcgcag ataccaaata ctgtccttct   6540
agtgtagccg tagttaggcc accacttcaa gaactctgta gcaccgccta catacctcgc   6600
tctgctaatc ctgttaccag tggctgctgc cagtggcgat aagtcgtgtc ttaccgggtt   6660
ggactcaaga cgatagttac cggataaggc gcagcggtcg ggctgaacgg ggggttcgtg   6720
cacacagccc agcttggagc gaacgaccta caccgaactg agatacctac agcgtgagct   6780
atgagaaagc gccacgcttc ccgaagggag aaaggcggac aggtatccgg taagcggcag   6840
ggtcggaaca ggagagcgca cgagggagct tccaggggga aacgcctggt atctttatag   6900
tcctgtcggg tttcgccacc tctgacttga gcgtcgattt ttgtgatgct cgtcaggggg   6960
gcggagccta tggaaaaacg ccagcaacgc ggccttttta cggttcctgg ccttttgctg   7020
gccttttgct cacatgttct ttcctgcgtt atcccctgat tctgtggata accgtattac   7080
cgcctttgag tgagctgata ccgctcgccg cagccgaacg accgagcgca gcgagtcagt   7140
gagcgaggaa gcggaagagc gcccaatacg caaaccgcct ctccccgcgc gttggccgat   7200
tcattaatg                                                           7209
```

<210> SEQ ID NO 20
<211> LENGTH: 7212
<212> TYPE: DNA
<213> ORGANISM: Artificial Sequence
<220> FEATURE:
<223> OTHER INFORMATION: Synthetic construct - AAV targeting vector

<400> SEQUENCE: 20

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtggga    180
actttatttg tctttctgtg tttcagttac ctaaattgaa tccttctgga gtattgtagg    240
tttggggagg ctaaataagt tgtgtttcat aaatgaacag aggtggcatc tatatcagta    300
agacagttgc atcacttttg catgatgctg tctaaaagaa ctaatttaag ctaaatgggg    360
aaaaggtcag aaaacaacaa ctaccccccc cccaccaaaa cccaccaaaa aaaattatgt    420
tttcaacttt agaacaaatc ttctatcctt tgtagctcag tcagtgggtg tgggcaaaat    480
cagttgggca gcagttagtg tgtgtccaga actgcaggtg cagcctccat atccttatta    540
gttcccttgg ttacagaccc cagtgggaca atgtttgaaa aattatattc accgtctagg    600
aaattgggaa ctgaaagtcc aatatctgcc tcagtggagt tctggcacct gcattatccc    660
ttctgggtat atcaagatca acagctgcac agatactttt gcttttcaca gattctacac    720
atatcatata aaggtgaata gtgtaaagct acctctacac cttaccaagc acacaggtgc    780
gtgccattta acatctagag cattccattg ccttatacaa gaactcagtt tatatgagct    840
cacaacatcg aaccaatccc cccccaattc agtgtgcatc cattatacct gaaacctgac    900
```

-continued

```
agagctgggg gctgtgggag gaggttggta ggaagaaatt attttgtgag ctgtgcacat    960
ttttgttcca tttgaaacta ggtagctagg ctgagggggga accaagaggg atgaggatta   1020
atgtcctggg tcctcaggaa ctttcattat caacagcaca caggtgaact ccagaaagaa   1080
gaagctatgg ccgcagtgat tctggagagc atctttctga agcgatcccg aacagagaaa   1140
caggagaata tgggccaaac aggatatctg tggtaagcag ttcctgcccc ggctcagggc   1200
caagaacagt tggaacagca gaatatgggc caaacaggat atctgtggta agcagttcct   1260
gccccggctc agggccaaga acagatggtc cccagatgcg gtcccgccct cagcagtttc   1320
tagagaacca tcagatgttt ccagggtgcc ccaaggacct gaaatgaccc tgtgccttat   1380
ttgaactaac caatcagttc gcttctcgct tctgttcgcg cgcttctgct ccccgagctc   1440
tatataagca gagctcgttt agtgaaccgt cagatcgcct ggagacgcca tccacgctgt   1500
tttgacttcc atagaaggat ctcgaggcca ccatggtgag caagggcgag gagctgttca   1560
ccggggtggt gcccatcctg gtcgagctgg acggcgacgt aaacggccac aagttcagcg   1620
tgtccggcga gggcgagggc gatgccacct acggcaagct gaccctgaag ttcatctgca   1680
ccaccggcaa gctgcccgtg ccctggccca ccctcgtgac caccctgacc tacggcgtgc   1740
agtgcttcag ccgctacccc gaccacatga agcagcacga cttcttcaag tccgccatgc   1800
ccgaaggcta cgtccaggag cgcaccatct tcttcaagga cgacggcaac tacaagaccc   1860
gcgccgaggt gaagttcgag ggcgacaccc tggtgaaccg catcgagctg aagggcatcg   1920
acttcaagga ggacggcaac atcctggggc acaagctgga gtacaactac aacagccaca   1980
acgtctatat catggccgac aagcagaaga acggcatcaa ggtgaacttc aagatccgcc   2040
acaacatcga ggacggcagc gtgcagctcg ccgaccacta ccagcagaac acccccatcg   2100
gcgacggccc cgtgctgctg cccgacaacc actacctgag cacccagtcc gccctgagca   2160
aagaccccaa cgagaagcgc gatcacatgg tcctgctgga gttcgtgacc gccgccggga   2220
tcactctcgg catggacgag ctgtacaagt aaactagtgt cgactgcttt atttgtgaaa   2280
tttgtgatgc tattgcttta tttgtaacca ttataagctg caataaacaa gttaacaaca   2340
acaattgcat tcattttatg tttcaggttc agggggaggt gtgggaggtt ttttaaaagc   2400
taaagccgga aagtcaaagg tcctaagaag ccacaaggaa aatattacca tggaatcttg   2460
gaattgatga gcactcatta aatgattgtt gaaaatgaaa tcgaagagtt ggaaattgct   2520
tccttacttc ctatgaggaa ggtacataca gtcattcact cttccatggt atttgccctc   2580
catttggtag tcatagattt atagatctgg aaggattttt ttttcttccc ccacatgaca   2640
ggtcctggtg ccacctcact ttgttgaatg attagataac aaaatctaat catctggttg   2700
cttaatccct cttaatcttt ctccattttc ttcctcattc tacttctcag agaagaggca   2760
gtaagaaggg ttcaatagat gttgagaaga tcacttgtgt tgaaacagtg gttcctgaaa   2820
aaaatcctcc tccagaaaga cagattccgg taagaagaga ccaatgtctg agatggggaa   2880
cagcagattt gaagaaattt gcaacattta aattctctgt aaatagactg gtgatgctgt   2940
gcaacgtgga acacggtcaa gtttccttta aaaattcttc actctaccat attggttata   3000
aagaatctta gcttctttcc ttcatattca gaacatctca ctaaacatgg aaaatttgtt   3060
aacacaaact tttaaatgat gctatatcta gttttcaaac tggtcagaga tcattgattt   3120
tattccctca gttctctcag gatcagattt agaggcttaa gtaagtctga atgtcataat   3180
cctagggctc tgagtcacat gatatccttt aatacettac tatttattct cttctcactt   3240
tccggagcga gagacataaa acctactgat tttgagttc acttttaaaa aatatatatc   3300
```

```
aatttcagta ttttcttttt ttcttttttt tttcttttttt tagacagagt ctcgctctgt   3360
tgcccaggct ggaatgcact ggtgccatct tggctcactg caaccttcac ctcccgggtt   3420
caagcaattc tcatgcctca gcctcccaag tctagagtag ataagtagca tggcgggtta   3480
atcattaact acaaggaacc cctagtgatg gagttggcca ctccctctct gcgcgctcgc   3540
tcgctcactg aggccgggcg accaaaggtc gcccgacgcc cgggctttgc ccgggcggcc   3600
tcagtgagcg agcgagcgcg ccagctggcg taatagcgaa gaggcccgca ccgatcgccc   3660
ttcccaacag ttgcgcagcc tgaatggcga atggcgattc cgttgcaatg gctggcggta   3720
atattgttct ggatattacc agcaaggccg atagtttgag ttcttctact caggcaagtg   3780
atgttattac taatcaaaga agtattgcga caacggttaa tttgcgtgat ggacagactc   3840
ttttactcgg tggcctcact gattataaaa acacttctca ggattctggc gtaccgttcc   3900
tgtctaaaat ccctttaatc ggcctcctgt ttagctcccg ctctgattct aacgaggaaa   3960
gcacgttata cgtgctcgtc aaagcaacca tagtacgcgc cctgtagcgg cgcattaagc   4020
gcggcgggtg tggtggttac gcgcagcgtg accgctacac ttgccagcgc cctagcgccc   4080
gctcctttcg ctttcttccc ttcctttctc gccacgttcg ccggctttcc ccgtcaagct   4140
ctaaatcggg ggctcccttt agggttccga tttagtgctt tacggcacct cgaccccaaa   4200
aaacttgatt agggtgatgg ttcacgtagt gggccatcgc cctgatagac ggtttttcgc   4260
cctttgacgt tggagtccac gttctttaat agtggactct tgttccaaac tggaacaaca   4320
ctcaacccta tctcggtcta ttcttttgat ttataaggga ttttgccgat ttcggcctat   4380
tggttaaaaa atgagctgat ttaacaaaaa tttaacgcga attttaacaa aatattaacg   4440
tttacaattt aaatatttgc ttatacaatc ttcctgtttt tggggctttt ctgattatca   4500
accggggtac atatgattga catgctagtt ttacgattac cgttcatcga ttctcttgtt   4560
tgctccagac tctcaggcaa tgacctgata gcctttgtag agacctctca aaaatagcta   4620
ccctctccgg catgaattta tcagctagaa cggttgaata tcatattgat ggtgatttga   4680
ctgtctccgg cctttctcac ccgtttgaat ctttacctac acattactca ggcattgcat   4740
ttaaaatata tgagggttct aaaaattttt atccttgcgt tgaaataaag gcttctcccg   4800
caaaagtatt acagggtcat aatgtttttg gtacaaccga tttagcttta tgctctgagg   4860
ctttattgct taattttgct aattctttgc cttgcctgta tgatttattg gatgttggaa   4920
tcgcctgatg cggtattttc tccttacgca tctgtgcggt atttcacacc gcatatggtg   4980
cactctcagt acaatctgct ctgatgccgc atagttaagc cagccccgac acccgccaac   5040
acccgctgac gcgccctgac gggcttgtct gctcccggca tccgcttaca gacaagctgt   5100
gaccgtctcc gggagctgca tgtgtcagag gttttcaccg tcatcaccga aacgcgcgag   5160
acgaaagggc ctcgtgatac gcctattttt ataggttaat gtcatgataa taatggtttc   5220
ttagacgtca ggtggcactt ttcggggaaa tgtgcgcgga acccctattt gtttattttt   5280
ctaaatacat tcaaatatgt atccgctcat gagacaataa ccctgataaa tgcttcaata   5340
atattgaaaa aggaagagta tgagtattca acatttccgt gtcgccctta ttcccttttt   5400
tgcggcattt tgccttcctg tttttgctca cccagaaacg ctggtgaaag taaaagatgc   5460
tgaagatcag ttgggtgcac gagtgggtta catcgaactg gatctcaaca gcggtaagat   5520
ccttgagagt tttcgccccg aagaacgttt tccaatgatg agcactttta aagttctgct   5580
atgtggcgcg gtattatccc gtattgacgc cgggcaagag caactcggtc gccgcataca   5640
```

ctattctcag aatgacttgg ttgagtactc accagtcaca gaaaagcatc ttacggatgg 5700
catgacagta agagaattat gcagtgctgc cataaccatg agtgataaca ctgcggccaa 5760
cttacttctg acaacgatcg gaggaccgaa ggagctaacc gcttttttgc acaacatggg 5820
ggatcatgta actcgccttg atcgttggga accggagctg aatgaagcca taccaaacga 5880
cgagcgtgac accacgatgc ctgtagcaat ggcaacaacg ttgcgcaaac tattaactgg 5940
cgaactactt actctagctt cccggcaaca attaatagac tggatggagg cggataaagt 6000
tgcaggacca cttctgcgct cggcccttcc ggctggctgg tttattgctg ataaatctgg 6060
agccggtgag cgtgggtctc gcggtatcat tgcagcactg gggccagatg gtaagccctc 6120
ccgtatcgta gttatctaca cgacggggag tcaggcaact atggatgaac gaaatagaca 6180
gatcgctgag ataggtgcct cactgattaa gcattggtaa ctgtcagacc aagtttactc 6240
atatatactt tagattgatt taaaacttca tttttaattt aaaaggatct aggtgaagat 6300
cctttttgat aatctcatga ccaaaatccc ttaacgtgag ttttcgttcc actgagcgtc 6360
agaccccgta gaaaagatca aaggatcttc ttgagatcct ttttttctgc gcgtaatctg 6420
ctgcttgcaa acaaaaaaac caccgctacc agcggtggtt tgtttgccgg atcaagagct 6480
accaactctt tttccgaagg taactggctt cagcagagcg cagataccaa atactgtcct 6540
tctagtgtag ccgtagttag gccaccactt caagaactct gtagcaccgc ctacatacct 6600
cgctctgcta atcctgttac cagtggctgc tgccagtggc gataagtcgt gtcttaccgg 6660
gttggactca agacgatagt taccggataa ggcgcagcgg tcgggctgaa cggggggttc 6720
gtgcacacag cccagcttgg agcgaacgac ctacaccgaa ctgagatacc tacagcgtga 6780
gctatgagaa agcgccacgc ttcccgaagg gagaaaggcg gacaggtatc cggtaagcgg 6840
cagggtcgga acaggagagc gcacgaggga gcttccaggg ggaaacgcct ggtatcttta 6900
tagtcctgtc gggtttcgcc acctctgact tgagcgtcga tttttgtgat gctcgtcagg 6960
ggggcggagc ctatggaaaa acgccagcaa cgcggccttt ttacggttcc tggccttttg 7020
ctggcctttt gctcacatgt tctttcctgc gttatcccct gattctgtgg ataaccgtat 7080
taccgccttt gagtgagctg ataccgctcg ccgcagccga acgaccgagc gcagcgagtc 7140
agtgagcgag gaagcggaag agcgcccaat acgcaaaccg cctctccccg cgcgttggcc 7200
gattcattaa tg 7212

<210> SEQ ID NO 21
<211> LENGTH: 7114
<212> TYPE: DNA
<213> ORGANISM: Artificial Sequence
<220> FEATURE:
<223> OTHER INFORMATION: Synthetic construct - AAV targeting vector

<400> SEQUENCE: 21
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtggga 180
actttatttg tctttctgtg tttcagttac ctaaattgaa tccttctgga gtattgtagg 240
tttggggagg ctaaataagt tgtgtttcat aaatgaacag aggtggcatc tatatcagta 300
agacagttgc atcacttttg catgatgctg tctaaaagaa ctaatttaag ctaaatgggg 360
aaaaggtcag aaaacaacaa ctaccccccc cccaccaaaa cccaccaaaa aaaattatgt 420
tttcaacttt agaacaaatc ttctatcctt tgtagctcag tcagtgggtg tgggcaaaat 480

```
cagttgggca gcagttagtg tgtgtccaga actgcaggtg cagcctccat atccttatta    540
gttcccttgg ttacagaccc cagtgggaca atgtttgaaa aattatattc accgtctagg    600
aaattgggaa ctgaaagtcc aatatctgcc tcagtggagt tctggcacct gcattatccc    660
ttctgggtat atcaagatca acagctgcac agatactttt gcttttcaca gattctacac    720
atatcatata aaggtgaata gtgtaaagct acctctacac cttaccaagc acacaggtgc    780
gtgccattta acatctagag cattccattg ccttatacaa gaactcagtt tatatgagct    840
cacaacatcg aaccaatccc cccccaattc agtgtgcatc cattatacct gaaacctgac    900
agagctgggg gctgtgggag gaggttggta ggaagaaatt attttgtgag ctgtgcacat    960
ttttgttcca tttgaaacta ggtagctagg ctgaggggga accaagaggg atgaggatta   1020
atgtcctggg tcctcaggaa ctttcattat caacagcaca caggtgaact ccagaaagaa   1080
gaagctatgg ccgcagtgat tctggagagc atctttctga agcgatcccg aacagagaaa   1140
caggagaata tgggccaaac aggatatctg tggtaagcag ttcctgcccc ggctcagggc   1200
caagaacagt tggaacagca gaatatgggc caaacaggat atctgtggta agcagttcct   1260
gccccggctc agggccaaga acagatggtc cccagatgcg gtcccgccct cagcagtttc   1320
tagagaacca tcagatgttt ccagggtgcc ccaaggacct gaaatgaccc tgtgccttat   1380
ttgaactaac caatcagttc gcttctcgct tctgttcgcg cgcttctgct ccccgagctc   1440
tatataagca gagctcgttt agtgaaccgt cagatcgcct ggagacgcca tccacgctgt   1500
tttgacttcc atagaaggat ctcgaggcca ccatggtgag caagggcgag gagctgttca   1560
ccggggtggt gcccatcctg gtcgagctgg acggcgacgt aaacggccac aagttcagcg   1620
tgtccggcga gggcgagggc gatgccacct acggcaagct gaccctgaag ttcatctgca   1680
ccaccggcaa gctgcccgtg ccctggccca ccctcgtgac caccctgacc tacggcgtgc   1740
agtgcttcag ccgctacccc gaccacatga agcagcacga cttcttcaag tccgccatgc   1800
ccgaaggcta cgtccaggag cgcaccatct tcttcaagga cgacggcaac tacaagaccc   1860
gcgccgaggt gaagttcgag ggcgacaccc tggtgaaccg catcgagctg aagggcatcg   1920
acttcaagga ggacggcaac atcctggggc acaagctgga gtacaactac aacagccaca   1980
acgtctatat catggccgac aagcagaaga acggcatcaa ggtgaacttc aagatccgcc   2040
acaacatcga ggacggcagc gtgcagctcg ccgaccacta ccagcagaac acccccatcg   2100
gcgacggccc cgtgctgctg cccgacaacc actacctgag cacccagtcc gccctgagca   2160
aagaccccaa cgagaagcgc gatcacatgg tcctgctgga gttcgtgacc gccgccggga   2220
tcactctcgg catggacgag ctgtacaagt aaactagtgt cgactgcttt atttgtgaaa   2280
tttgtgatgc tattgcttta tttgtaacca ttataagctg caataaacaa gttaacaaca   2340
acaattgcat tcattttatg tttcaggttc agggggaggt gtgggaggtt ttttaaaggg   2400
gtaagtttct cgactatgaa aactgagttt caagatatca aggacttggc cttagatctt   2460
tcttggggaa gaggtaaatt ttcgttggta ggaggagggg agtagaatgg acctaagttc   2520
tttcaaattc agcaaaatat ttcctagcct ataactagct aaagccggaa agtcaaaggt   2580
cctaagaagc cacaaggaaa atattaccat ggaatcttgg aattgatgag cactcattaa   2640
atgattgttg aaaatgaaat cgaagagttg gaaattgctt ccttacttcc tatgaggaag   2700
gtacatacag tcattcactc ttccatggta tttgccctcc atttggtagt catagattta   2760
tagatctgga aggatttttt tttcttcccc cacatgacag gtcctggtgc cacctcactt   2820
```

tgttgaatga ttagataaca aaatctaatc atctggttgc ttaatccctc ttaatctttc 2880
tccattttct tcctcattct acttctcaga gaagaggcag taagaagggt tcaatagatg 2940
ttgagaagat cacttgtgtt gaaacagtgg ttcctgaaaa aaatcctcct ccagaaagac 3000
agattccggt aagaagagac caatgtctga gatggggaac agcagatttg aagaaatttg 3060
caacatttaa attctctgta aatagactgg tgatgctgtg caacgtggaa cacggtcaag 3120
tttcctttaa aaattcttca ctctaccata ttggttataa agaatcttag cttctttcct 3180
tcatattcag aacatctcac taaacatgga aaatttgtta acacaaactt ttaaatgatg 3240
ctatatctag ttttcaaact ggtcagagat cattgatttt attccctcag ttctctcagg 3300
atcagattta gaggcttaag taagtctgaa tgtcataatc ctagggctct gctctagagt 3360
agataagtag catggcgggt taatcattaa ctacaaggaa cccctagtga tggagttggc 3420
cactccctct ctgcgcgctc gctcgctcac tgaggccggg cgaccaaagg tcgcccgacg 3480
cccgggcttt gcccgggcgg cctcagtgag cgagcgagcg cgccagctgg cgtaatagcg 3540
aagaggcccg caccgatcgc ccttcccaac agttgcgcag cctgaatggc gaatggcgat 3600
tccgttgcaa tggctggcgg taatattgtt ctggatatta ccagcaaggc cgatagtttg 3660
agttcttcta ctcaggcaag tgatgttatt actaatcaaa gaagtattgc gacaacggtt 3720
aatttgcgtg atggacagac tcttttactc ggtggcctca ctgattataa aaacacttct 3780
caggattctg gcgtaccgtt cctgtctaaa atccctttaa tcggcctcct gtttagctcc 3840
cgctctgatt ctaacgagga aagcacgtta tacgtgctcg tcaaagcaac catagtacgc 3900
gccctgtagc ggcgcattaa gcgcggcggg tgtggtggtt acgcgcagcg tgaccgctac 3960
acttgccagc gccctagcgc ccgctccttt cgctttcttc ccttcctttc tcgccacgtt 4020
cgccggcttt ccccgtcaag ctctaaatcg ggggctccct ttagggttcc gatttagtgc 4080
tttacggcac ctcgacccca aaaaacttga ttagggtgat ggttcacgta gtgggccatc 4140
gccctgatag acggtttttc gccctttgac gttggagtcc acgttcttta atagtggact 4200
cttgttccaa actggaacaa cactcaaccc tatctcggtc tattcttttg atttataagg 4260
gattttgccg atttcggcct attggttaaa aaatgagctg atttaacaaa aatttaacgc 4320
gaattttaac aaaatattaa cgtttacaat ttaaatattt gcttatacaa tcttcctgtt 4380
tttggggctt ttctgattat caaccggggt acatatgatt gacatgctag ttttacgatt 4440
accgttcatc gattctcttg tttgctccag actctcaggc aatgacctga tagcctttgt 4500
agagacctct caaaaatagc taccctctcc ggcatgaatt tatcagctag aacggttgaa 4560
tatcatattg atggtgattt gactgtctcc ggcctttctc acccgtttga atctttacct 4620
acacattact caggcattgc atttaaaata tatgagggtt ctaaaaattt ttatccttgc 4680
gttgaaataa aggcttctcc cgcaaaagta ttacagggtc ataatgtttt tggtacaacc 4740
gatttagctt tatgctctga ggctttattg cttaattttg ctaattcttt gccttgcctg 4800
tatgatttat tggatgttgg aatcgcctga tgcggtattt tctccttacg catctgtgcg 4860
gtatttcaca ccgcatatgg tgcactctca gtacaatctg ctctgatgcc gcatagttaa 4920
gccagccccg acacccgcca acacccgctg acgcgccctg acgggcttgt ctgctcccgg 4980
catccgctta cagacaagct gtgaccgtct ccgggagctg catgtgtcag aggttttcac 5040
cgtcatcacc gaaacgcgcg agacgaaagg gcctcgtgat acgcctattt ttataggtta 5100
atgtcatgat aataatggtt tcttagacgt caggtggcac ttttcgggga aatgtgcgcg 5160
gaacccctat ttgtttattt ttctaaatac attcaaatat gtatccgctc atgagacaat 5220
aaccctgata aatgcttcaa taatattgaa aaaggaagag tatgagtatt caacatttcc 5280
gtgtcgccct tattcccttt tttgcggcat tttgccttcc tgtttttgct cacccagaaa 5340
cgctggtgaa agtaaaagat gctgaagatc agttgggtgc acgagtgggt tacatcgaac 5400
tggatctcaa cagcggtaag atccttgaga gttttcgccc cgaagaacgt tttccaatga 5460
tgagcacttt taaagttctg ctatgtggcg cggtattatc ccgtattgac gccgggcaag 5520
agcaactcgg tcgccgcata cactattctc agaatgactt ggttgagtac tcaccagtca 5580
cagaaaagca tcttacggat ggcatgacag taagagaatt atgcagtgct gccataacca 5640
tgagtgataa cactgcggcc aacttacttc tgacaacgat cggaggaccg aaggagctaa 5700
ccgctttttt gcacaacatg ggggatcatg taactcgcct tgatcgttgg gaaccggagc 5760
tgaatgaagc cataccaaac gacgagcgtg acaccacgat gcctgtagca atggcaacaa 5820
cgttgcgcaa actattaact ggcgaactac ttactctagc ttcccggcaa caattaatag 5880
actggatgga ggcggataaa gttgcaggac cacttctgcg ctcggccctt ccggctggct 5940
ggtttattgc tgataaatct ggagccggtg agcgtgggtc tcgcggtatc attgcagcac 6000
tggggccaga tggtaagccc tcccgtatcg tagttatcta cacgacgggg agtcaggcaa 6060
ctatggatga acgaaataga cagatcgctg agataggtgc ctcactgatt aagcattggt 6120
aactgtcaga ccaagtttac tcatatatac tttagattga tttaaaactt catttttaat 6180
ttaaaaggat ctaggtgaag atcctttttg ataatctcat gaccaaaatc ccttaacgtg 6240
agttttcgtt ccactgagcg tcagaccccg tagaaaagat caaaggatct tcttgagatc 6300 cttttttttct gcgcgtaatc tgctgcttgc aaacaaaaaa accaccgcta ccagcggtgg 6360
tttgtttgcc ggatcaagag ctaccaactc tttttccgaa ggtaactggc ttcagcagag 6420
cgcagatacc aaatactgtc cttctagtgt agccgtagtt aggccaccac ttcaagaact 6480
ctgtagcacc gcctacatac ctcgctctgc taatcctgtt accagtggct gctgccagtg 6540
gcgataagtc gtgtcttacc gggttggact caagacgata gttaccggat aaggcgcagc 6600
ggtcgggctg aacggggggt tcgtgcacac agcccagctt ggagcgaacg acctacaccg 6660
aactgagata cctacagcgt gagctatgag aaagcgccac gcttcccgaa gggagaaagg 6720
cggacaggta tccggtaagc ggcagggtcg gaacaggaga gcgcacgagg gagcttccag 6780
ggggaaacgc ctggtatctt tatagtcctg tcgggtttcg ccacctctga cttgagcgtc 6840
gatttttgtg atgctcgtca ggggggcgga gcctatggaa aaacgccagc aacgcggcct 6900
ttttacggtt cctggccttt tgctggcctt ttgctcacat gttctttcct gcgttatccc 6960
ctgattctgt ggataaccgt attaccgcct ttgagtgagc tgataccgct cgccgcagcc 7020
gaacgaccga gcgcagcgag tcagtgagcg aggaagcgga agagcgccca atacgcaaac 7080
cgcctctccc cgcgcgttgg ccgattcatt aatg 7114

<210> SEQ ID NO 22
<211> LENGTH: 7209
<212> TYPE: DNA
<213> ORGANISM: Artificial Sequence
<220> FEATURE:
<223> OTHER INFORMATION: Synthetic construct - AAV targeting sequence

<400> SEQUENCE: 22
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120

```
actaggggtt ccttgtagtt aatgattaac ccgccatgct acttatctac acgcgtggga    180
actttatttg tctttctgtg tttcagttac ctaaattgaa tccttctgga gtattgtagg    240
tttggggagg ctaaataagt tgtgtttcat aaatgaacag aggtggcatc tatatcagta    300
agacagttgc atcacttttg catgatgctg tctaaaagaa ctaatttaag ctaaatgggg    360
aaaaggtcag aaaacaacaa ctaccccccc cccaccaaaa cccaccaaaa aaaattatgt    420
tttcaacttt agaacaaatc ttctatcctt tgtagctcag tcagtgggtg tgggcaaaat    480
cagttgggca gcagttagtg tgtgtccaga actgcaggtg cagcctccat atccttatta    540
gttcccttgg ttacagaccc cagtgggaca atgtttgaaa aattatattc accgtctagg    600
aaattgggaa ctgaaagtcc aatatctgcc tcagtggagt tctggcacct gcattatccc    660
ttctgggtat atcaagatca acagctgcac agatactttt gcttttcaca gattctacac    720
atatcatata aaggtgaata gtgtaaagct acctctacac cttaccaagc acacaggtgc    780
gtgccattta acatctagag cattccattg ccttatacaa gaactcagtt tatatgagct    840
cacaacatcg aaccaatccc cccccaattc agtgtgcatc cattatacct gaaacctgac    900
agagctgggg gctgtgggag gaggttggta ggaagaaatt attttgtgag ctgtgcacat    960
ttttgttcca tttgaaacta ggtagctagg ctgaggggga accaagaggg atgaggatta   1020
atgtcctggg tcctcaggaa ctttcattat caacagcaca caggtgaact ccagaaagaa   1080
gaagctatgg ccgcagtgat tctggagagc atctttctga agcgatcccg aacagagaaa   1140
caggagaata tgggccaaac aggatatctg tggtaagcag ttcctgcccc ggctcagggc   1200
caagaacagt tggaacagca gaatatgggc caaacaggat atctgtggta agcagttcct   1260
gccccggctc agggccaaga acagatggtc cccagatgcg gtcccgccct cagcagtttc   1320
tagagaacca tcagatgttt ccagggtgcc ccaaggacct gaaatgaccc tgtgccttat   1380
ttgaactaac caatcagttc gcttctcgct tctgttcgcg cgcttctgct ccccgagctc   1440
tatataagca gagctcgttt agtgaaccgt cagatcgcct ggagacgcca tccacgctgt   1500
tttgacttcc atagaaggat ctcgaggcca ccatggtgag caagggcgag gagctgttca   1560
ccggggtggt gcccatcctg gtcgagctgg acggcgacgt aaacggccac aagttcagcg   1620
tgtccggcga gggcgagggc gatgccacct acggcaagct gaccctgaag ttcatctgca   1680
ccaccggcaa gctgcccgtg ccctggccca ccctcgtgac caccctgacc tacggcgtgc   1740
agtgcttcag ccgctacccc gaccacatga agcagcacga cttcttcaag tccgccatgc   1800
ccgaaggcta cgtccaggag cgcaccatct tcttcaagga cgacggcaac tacaagaccc   1860
gcgccgaggt gaagttcgag ggcgacaccc tggtgaaccg catcgagctg aagggcatcg   1920
acttcaagga ggacggcaac atcctggggc acaagctgga gtacaactac aacagccaca   1980
acgtctatat catggccgac aagcagaaga acggcatcaa ggtgaacttc aagatccgcc   2040
acaacatcga ggacggcagc gtgcagctcg ccgaccacta ccagcagaac acccccatcg   2100
gcgacggccc cgtgctgctg cccgacaacc actacctgag cacccagtcc gccctgagca   2160
aagaccccaa cgagaagcgc gatcacatgg tcctgctgga gttcgtgacc gccgccggga   2220
tcactctcgg catggacgag ctgtacaagt aaactagtgt cgactgcttt atttgtgaaa   2280
tttgtgatgc tattgcttta tttgtaacca ttataagctg caataaacaa gttaacaaca   2340
acaattgcat tcattttatg tttcaggttc agggggaggt gtgggaggtt ttttaaaaac   2400
agaaaaagaa aacatcacct ctaaacttca agaagcgcct gtttctcttg accgtgcaca   2460
aactctccta ctatgagtat gactttgaac gtggtgtaag tttctcgact atgaaaactg   2520
```

```
agtttcaaga tatcaaggac ttggccttag atctttcttg gggaagaggt aaattttcgt   2580
tggtaggagg aggggagtag aatggaccta agttctttca aattcagcaa aatatttcct   2640
agcctataac tagctaaagc cggaaagtca aaggtcctaa gaagccacaa ggaaaatatt   2700
accatggaat cttggaattg atgagcactc attaaatgat tgttgaaaat gaaatcgaag   2760
agttggaaat tgcttcctta cttcctatga ggaaggtaca tacagtcatt cactcttcca   2820
tggtatttgc cctccatttg gtagtcatag atttatagat ctggaaggat tttttttct    2880
tcccccacat gacaggtcct ggtgccacct cactttgttg aatgattaga taacaaaatc   2940
taatcatctg gttgcttaat ccctcttaat ctttctccat tttcttcctc attctacttc   3000
tcagagaaga ggcagtaaga agggttcaat agatgttgag aagatcactt gtgttgaaac   3060
agtggttcct gaaaaaaatc ctcctccaga aagacagatt ccggtaagaa gagaccaatg   3120
tctgagatgg ggaacagcag atttgaagaa atttgcaaca tttaaattct ctgtaaatag   3180
actggtgatg ctgtgcaacg tggaacacgg tcaagtttcc tttaaaaatt cttcactcta   3240
ccatattggt tataaagaat cttagcttct ttccttcata ttcagaacat ctcactaaac   3300
atggaaaatt tgttaacaca aacttttaaa tgatgctata tctagttttc aaactggtca   3360
gagatcattg attttattcc ctcagttctc tcaggatcag atttagaggc ttaagtaagt   3420
ctgaatgtca taatcctagg gctctgctct agagtagata agtagcatgg cgggttaatc   3480
attaactaca aggaacccct agtgatggag ttggccactc cctctctgcg cgctcgctcg   3540
ctcactgagg ccgggcgacc aaaggtcgcc cgacgcccgg gctttgcccg ggcggcctca   3600
gtgagcgagc gagcgcgcca gctggcgtaa tagcgaagag gcccgcaccg atcgcccttc   3660
ccaacagttg cgcagcctga atggcgaatg gcgattccgt tgcaatggct ggcggtaata   3720
ttgttctgga tattaccagc aaggccgata gtttgagttc ttctactcag gcaagtgatg   3780
ttattactaa tcaaagaagt attgcgacaa cggttaattt gcgtgatgga cagactcttt   3840
tactcggtgg cctcactgat tataaaaaca cttctcagga ttctggcgta ccgttcctgt   3900
ctaaaatccc tttaatcggc ctcctgttta gctcccgctc tgattctaac gaggaaagca   3960
cgttatacgt gctcgtcaaa gcaaccatag tacgcgccct gtagcggcgc attaagcgcg   4020
gcgggtgtgg tggttacgcg cagcgtgacc gctacacttg ccagcgccct agcgcccgct   4080
cctttcgctt tcttcccttc ctttctcgcc acgttcgccg gctttccccg tcaagctcta   4140
aatcgggggc tccctttagg gttccgattt agtgctttac ggcacctcga ccccaaaaaa   4200
cttgattagg gtgatggttc acgtagtggg ccatcgccct gatagacggt ttttcgccct   4260
ttgacgttgg agtccacgtt ctttaatagt ggactcttgt tccaaactgg aacaacactc   4320
aaccctatct cggtctattc ttttgattta taagggattt tgccgatttc ggcctattgg   4380
ttaaaaaatg agctgattta acaaaaattt aacgcgaatt ttaacaaaat attaacgttt   4440
acaatttaaa tatttgctta tacaatcttc ctgtttttgg ggcttttctg attatcaacc   4500
ggggtacata tgattgacat gctagtttta cgattaccgt tcatcgattc tcttgtttgc   4560
tccagactct caggcaatga cctgatagcc tttgtagaga cctctcaaaa atagctaccc   4620
tctccggcat gaatttatca gctagaacgg ttgaatatca tattgatggt gatttgactg   4680
tctccggcct ttctcacccg tttgaatctt tacctacaca ttactcaggc attgcattta   4740
aaatatatga gggttctaaa aatttttatc cttgcgttga aataaaggct tctcccgcaa   4800
aagtattaca gggtcataat gtttttggta caaccgattt agctttatgc tctgaggctt   4860
```

tattgcttaa ttttgctaat tctttgcctt gcctgtatga tttattggat gttggaatcg 4920
cctgatgcgg tattttctcc ttacgcatct gtgcggtatt tcacaccgca tatggtgcac 4980
tctcagtaca atctgctctg atgccgcata gttaagccag ccccgacacc cgccaacacc 5040
cgctgacgcg ccctgacggg cttgtctgct cccggcatcc gcttacagac aagctgtgac 5100
cgtctccggg agctgcatgt gtcagaggtt ttcaccgtca tcaccgaaac gcgcgagacg 5160
aaagggcctc gtgatacgcc tatttttata ggttaatgtc atgataataa tggtttctta 5220
gacgtcaggt ggcacttttc ggggaaatgt gcgcggaacc cctatttgtt tatttttcta 5280
aatacattca aatatgtatc cgctcatgag acaataaccc tgataaatgc ttcaataata 5340
ttgaaaaagg aagagtatga gtattcaaca tttccgtgtc gcccttattc ccttttttgc 5400
ggcattttgc cttcctgttt ttgctcaccc agaaacgctg gtgaaagtaa aagatgctga 5460
agatcagttg ggtgcacgag tgggttacat cgaactggat ctcaacagcg gtaagatcct 5520
tgagagtttt cgccccgaag aacgttttcc aatgatgagc acttttaaag ttctgctatg 5580
tggcgcggta ttatcccgta ttgacgccgg gcaagagcaa ctcggtcgcc gcatacacta 5640
ttctcagaat gacttggttg agtactcacc agtcacagaa aagcatctta cggatggcat 5700
gacagtaaga gaattatgca gtgctgccat aaccatgagt gataacactg cggccaactt 5760
acttctgaca acgatcggag gaccgaagga gctaaccgct tttttgcaca acatggggga 5820
tcatgtaact cgccttgatc gttgggaacc ggagctgaat gaagccatac caaacgacga 5880
gcgtgacacc acgatgcctg tagcaatggc aacaacgttg cgcaaactat taactggcga 5940
actacttact ctagcttccc ggcaacaatt aatagactgg atggaggcgg ataaagttgc 6000
aggaccactt ctgcgctcgg cccttccggc tggctggttt attgctgata aatctggagc 6060
cggtgagcgt gggtctcgcg gtatcattgc agcactgggg ccagatggta agccctcccg 6120
tatcgtagtt atctacacga cggggagtca ggcaactatg gatgaacgaa atagacagat 6180
cgctgagata ggtgcctcac tgattaagca ttggtaactg tcagaccaag tttactcata 6240
tatactttag attgatttaa aacttcattt ttaatttaaa aggatctagg tgaagatcct 6300
ttttgataat ctcatgacca aaatccctta acgtgagttt tcgttccact gagcgtcaga 6360
ccccgtagaa aagatcaaag gatcttcttg agatcctttt tttctgcgcg taatctgctg 6420
cttgcaaaca aaaaaaccac cgctaccagc ggtggtttgt ttgccggatc aagagctacc 6480
aactcttttt ccgaaggtaa ctggcttcag cagagcgcag ataccaaata ctgtccttct 6540
agtgtagccg tagttaggcc accacttcaa gaactctgta gcaccgccta catacctcgc 6600
tctgctaatc ctgttaccag tggctgctgc cagtggcgat aagtcgtgtc ttaccgggtt 6660
ggactcaaga cgatagttac cggataaggc gcagcggtcg ggctgaacgg ggggttcgtg 6720
cacacagccc agcttggagc gaacgaccta caccgaactg agatacctac agcgtgagct 6780
atgagaaagc gccacgcttc ccgaagggag aaaggcggac aggtatccgg taagcggcag 6840
ggtcggaaca ggagagcgca cgagggagct tccaggggga aacgcctggt atctttatag 6900
tcctgtcggg tttcgccacc tctgacttga gcgtcgattt ttgtgatgct cgtcaggggg 6960
gcggagccta tggaaaaacg ccagcaacgc ggccttttta cggttcctgg ccttttgctg 7020
gccttttgct cacatgttct ttcctgcgtt atcccctgat tctgtggata accgtattac 7080
cgcctttgag tgagctgata ccgctcgccg cagccgaacg accgagcgca gcgagtcagt 7140
gagcgaggaa gcggaagagc gcccaatacg caaaccgcct ctccccgcgc gttggccgat 7200
tcattaatg 7209

<210> SEQ ID NO 23
<211> LENGTH: 6050
<212> TYPE: DNA
<213> ORGANISM: Artificial Sequence
<220> FEATURE:
<223> OTHER INFORMATION: Synthetic construct - AAV targeting vector

<400> SEQUENCE: 23

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtattc    180
accgtctagg aaattgggaa ctgaaagtcc aatatctgcc tcagtggagt tctggcacct    240
gcattatccc ttctgggtat atcaagatca acagctgcac agatactttt gcttttcaca    300
gattctacac atatcatata aaggtgaata gtgtaaagct acctctacac cttaccaagc    360
acacaggtgc gtgccattta acatctagag cattccattg ccttatacaa gaactcagtt    420
tatatgagct cacaacatcg aaccaatccc cccccaattc agtgtgcatc cattatacct    480
gaaacctgac agagctgggg gctgtgggag gaggttggta ggaagaaatt attttgtgag    540
ctgtgcacat ttttgttcca tttgaaacta ggtagctagg ctgaggggga accaagaggg    600
atgaggatta atgtcctggg tcctcaggaa ctttcattat caacagcaca caggtgaact    660
ccagaaagaa gaagctatgg tgagcaaggg cgaggagctg ttcaccgggg tggtgcccat    720
cctggtcgag ctggacggcg acgtaaacgg ccacaagttc agcgtgtccg gcgagggcga    780
gggcgatgcc acctacggca agctgaccct gaagttcatc tgcaccaccg gcaagctgcc    840
cgtgccctgg cccaccctcg tgaccaccct gacctacggc gtgcagtgct tcagccgcta    900
ccccgaccac atgaagcagc acgacttctt caagtccgcc atgcccgaag gctacgtcca    960
ggagcgcacc atcttcttca aggacgacgg caactacaag acccgcgccg aggtgaagtt   1020
cgagggcgac accctggtga accgcatcga gctgaagggc atcgacttca aggaggacgg   1080
caacatcctg gggcacaagc tggagtacaa ctacaacagc cacaacgtct atatcatggc   1140
cgacaagcag aagaacggca tcaaggtgaa cttcaagatc cgccacaaca tcgaggacgg   1200
cagcgtgcag ctcgccgacc actaccagca gaacaccccc atcggcgacg gccccgtgct   1260
gctgcccgac aaccactacc tgagcaccca gtccgccctg agcaaagacc ccaacgagaa   1320
gcgcgatcac atggtcctgc tggagttcgt gaccgccgcc gggatcactc tcggcatgga   1380
cgagctgtac aagtaagata atcaacctct ggattacaaa atttgtgaaa gattgactgg   1440
tattcttaac tatgttgctc cttttacgct atgtggatac gctgctttaa tgcctttgta   1500
tcatgctatt gcttcccgta tggctttcat tttctcctcc ttgtataaat cctggttagt   1560
tcttgccacg gcggaactca tcgccgcctg ccttgcccgc tgctggacag gggctcggct   1620
gttgggcact gacaattccg tggactagtg tcgactgctt tatttgtgaa atttgtgatg   1680
ctattgcttt atttgtaacc attataagct gcaataaaca agttaacaac aacaattgca   1740
ttcattttat gtttcaggtt cagggggagg tgtgggaggt tttttaaagg ggtaagtttc   1800
tcgactatga aaactgagtt tcaagatatc aaggacttgg ccttagatct ttcttgggga   1860
agaggtaaat ttccgttggt aggaggaggg gagtagaatg gacctaagtt ctttcaaatt   1920
cagcaaaata tttcctagcc tataactagc taaagccgga aagtcaaagg tcctaagaag   1980
ccacaaggaa aatattacca tggaatcttg gaattgatga gcactcatta aatgattgtt   2040
```

-continued

```
gaaaatgaaa tcgaagagtt ggaaattgct tccttacttc ctatgaggaa ggtacataca   2100
gtcattcact cttccatggt atttgccctc catttggtag tcatagattt atagatctgg   2160
aaggattttt ttttcttccc ccacatgaca ggtcctggtg ccacctcact ttgttgaatg   2220
attagataac aaaatctaat catctggttg cttaatccct cttaatcttt ctccattttc   2280
ttcctcattc tagagtagat aagtagcatg gcgggttaat cattaactac aaggaacccc   2340
tagtgatgga gttggccact ccctctctgc gcgctcgctc gctcactgag gccgggcgac   2400
caaaggtcgc ccgacgcccg ggctttgccc gggcggcctc agtgagcgag cgagcgcgcc   2460
agctggcgta atagcgaaga ggcccgcacc gatcgccctt cccaacagtt gcgcagcctg   2520
aatggcgaat ggcgattccg ttgcaatggc tggcggtaat attgttctgg atattaccag   2580
caaggccgat agtttgagtt cttctactca ggcaagtgat gttattacta atcaaagaag   2640
tattgcgaca acggttaatt tgcgtgatgg acagactctt ttactcggtg gcctcactga   2700
ttataaaaac acttctcagg attctggcgt accgttcctg tctaaaatcc ctttaatcgg   2760
cctcctgttt agctcccgct ctgattctaa cgaggaaagc acgttatacg tgctcgtcaa   2820
agcaaccata gtacgcgccc tgtagcggcg cattaagcgc ggcgggtgtg gtggttacgc   2880
gcagcgtgac cgctacactt gccagcgccc tagcgcccgc tcctttcgct ttcttccctt   2940
cctttctcgc cacgttcgcc ggctttcccc gtcaagctct aaatcggggg ctccctttag   3000
ggttccgatt tagtgcttta cggcacctcg accccaaaaa acttgattag ggtgatggtt   3060
cacgtagtgg gccatcgccc tgatagacgg tttttcgccc tttgacgttg gagtccacgt   3120
tctttaatag tggactcttg ttccaaactg gaacaacact caaccctatc tcggtctatt   3180
cttttgattt ataagggatt ttgccgattt cggcctattg gttaaaaaat gagctgattt   3240
aacaaaaatt taacgcgaat tttaacaaaa tattaacgtt tacaatttaa atatttgctt   3300
atacaatctt cctgtttttg gggcttttct gattatcaac cggggtacat atgattgaca   3360
tgctagtttt acgattaccg ttcatcgatt ctcttgtttg ctccagactc tcaggcaatg   3420
acctgatagc ctttgtagag acctctcaaa aatagctacc ctctccggca tgaatttatc   3480
agctagaacg gttgaatatc atattgatgg tgatttgact gtctccggcc tttctcaccc   3540
gtttgaatct ttacctacac attactcagg cattgcattt aaaatatatg agggttctaa   3600
aaatttttat ccttgcgttg aaataaaggc ttctcccgca aaagtattac agggtcataa   3660
tgtttttggt acaaccgatt tagctttatg ctctgaggct ttattgctta attttgctaa   3720
ttctttgcct tgcctgtatg atttattgga tgttggaatc gcctgatgcg gtattttctc   3780
cttacgcatc tgtgcggtat ttcacaccgc atatggtgca ctctcagtac aatctgctct   3840
gatgccgcat agttaagcca gccccgacac ccgccaacac ccgctgacgc gccctgacgg   3900
gcttgtctgc tcccggcatc cgcttacaga caagctgtga ccgtctccgg gagctgcatg   3960
tgtcagaggt tttcaccgtc atcaccgaaa cgcgcgagac gaaagggcct cgtgatacgc   4020
ctatttttat aggttaatgt catgataata atggtttctt agacgtcagg tggcactttt   4080
cggggaaatg tgcgcggaac ccctatttgt ttatttttct aaatacattc aaatatgtat   4140
ccgctcatga gacaataacc ctgataaatg cttcaataat attgaaaaag gaagagtatg   4200
agtattcaac atttccgtgt cgcccttatt cccttttttg cggcattttg ccttcctgtt   4260
tttgctcacc cagaaacgct ggtgaaagta aaagatgctg aagatcagtt gggtgcacga   4320
gtgggttaca tcgaactgga tctcaacagc ggtaagatcc ttgagagttt tcgccccgaa   4380
gaacgttttc caatgatgag cacttttaaa gttctgctat gtggcgcggt attatcccgt   4440
```

attgacgccg ggcaagagca actcggtcgc cgcatacact attctcagaa tgacttggtt 4500
gagtactcac cagtcacaga aaagcatctt acggatggca tgacagtaag agaattatgc 4560
agtgctgcca taaccatgag tgataacact gcggccaact tacttctgac aacgatcgga 4620
ggaccgaagg agctaaccgc ttttttgcac aacatggggg atcatgtaac tcgccttgat 4680
cgttgggaac cggagctgaa tgaagccata ccaaacgacg agcgtgacac cacgatgcct 4740
gtagcaatgg caacaacgtt gcgcaaacta ttaactggcg aactacttac tctagcttcc 4800
cggcaacaat taatagactg gatggaggcg gataaagttg caggaccact tctgcgctcg 4860
gcccttccgg ctggctggtt tattgctgat aaatctggag ccggtgagcg tgggtctcgc 4920
ggtatcattg cagcactggg gccagatggt aagccctccc gtatcgtagt tatctacacg 4980
acggggagtc aggcaactat ggatgaacga aatagacaga tcgctgagat aggtgcctca 5040
ctgattaagc attggtaact gtcagaccaa gtttactcat atatacttta gattgattta 5100
aaacttcatt tttaatttaa aaggatctag gtgaagatcc tttttgataa tctcatgacc 5160
aaaatccctt aacgtgagtt ttcgttccac tgagcgtcag accccgtaga aaagatcaaa 5220
ggatcttctt gagatccttt ttttctgcgc gtaatctgct gcttgcaaac aaaaaaacca 5280
ccgctaccag cggtggtttg tttgccggat caagagctac caactctttt tccgaaggta 5340
actggcttca gcagagcgca gataccaaat actgtccttc tagtgtagcc gtagttaggc 5400
caccacttca agaactctgt agcaccgcct acatacctcg ctctgctaat cctgttacca 5460
gtggctgctg ccagtggcga taagtcgtgt cttaccgggt tggactcaag acgatagtta 5520
ccggataagg cgcagcggtc gggctgaacg gggggttcgt gcacacagcc cagcttggag 5580
cgaacgacct acaccgaact gagataccta cagcgtgagc tatgagaaag cgccacgctt 5640
cccgaaggga gaaaggcgga caggtatccg gtaagcggca gggtcggaac aggagagcgc 5700
acgagggagc ttccaggggg aaacgcctgg tatctttata gtcctgtcgg gtttcgccac 5760
ctctgacttg agcgtcgatt tttgtgatgc tcgtcagggg ggcggagcct atggaaaaac 5820
gccagcaacg cggccttttt acggttcctg gccttttgct ggccttttgc tcacatgttc 5880
tttcctgcgt tatcccctga ttctgtggat aaccgtatta ccgcctttga gtgagctgat 5940
accgctcgcc gcagccgaac gaccgagcgc agcgagtcag tgagcgagga agcggaagag 6000
cgcccaatac gcaaaccgcc tctccccgcg cgttggccga ttcattaatg 6050

<210> SEQ ID NO 24
<211> LENGTH: 5908
<212> TYPE: DNA
<213> ORGANISM: Artificial Sequence
<220> FEATURE:
<223> OTHER INFORMATION: Artificial Sequence - AAV targeting sequence

<400> SEQUENCE: 24
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtattc 180
accgtctagg aaattgggaa ctgaaagtcc aatatctgcc tcagtggagt tctggcacct 240
gcattatccc ttctgggtat atcaagatca acagctgcac agatactttt gcttttcaca 300
gattctacac atatcatata aaggtgaata gtgtaaagct acctctacac cttaccaagc 360
acacaggtgc gtgccattta acatctagag cattccattg ccttatacaa gaactcagtt 420

-continued

```
tatatgagct cacaacatcg aaccaatccc cccccaattc agtgtgcatc cattatacct    480
gaaacctgac agagctgggg gctgtgggag gaggttggta ggaagaaatt attttgtgag    540
ctgtgcacat ttttgttcca tttgaaacta ggtagctagg ctgaggggga accaagaggg    600
atgaggatta atgtcctggg tcctcaggaa ctttcattat caacagcaca caggtgaact    660
ccagaaagaa gaagctatgg ccgccgtgat cctggaaagc atcttcctga agcggagcca    720
gcagaagaag aaaaccagcc ccctgaactt caagaagcgg ctgttcctgc tgaccgtgca    780
caagctgtcc tactacgagt acgacttcga gcggggcaga cggggcagca agaagggcag    840
catcgacgtc gagaagatca cctgcgtgga gaccgtggtg cccgagaaga acccccctcc    900
cgagcggcag atccccagac ggggcgagga aagcagcgag atggaacaga tcagcatcat    960
cgagcggttc ccttacccat tccaagtggt gtacgacgag ggcccccctgt acgtgttcag   1020
ccccaccgag gaactgcgga agcggtggat tcaccagctg aagaacgtga tccggtacaa   1080
cagcgacctg gtgcagaagt accacccctg cttttggatc gacggccagt acctgtgctg   1140
cagccagacc gccaagaacg ctatgggctg ccagattctg gaaaaccgga acggcagcct   1200
gaagcccggc agcagccaca gaaagaccaa gaagcccctg ccccccaccc ccgaagagga   1260
ccagatcctg aagaagcctc tgcctcccga gcccgccgct gcacctgtga gcaccagcga   1320
gctgaagaaa gtggtggccc tgtacgacta catgcccatg aacgccaacg acctgcagct   1380
gcggaagggc gacgagtact tcatcctgga agaaagcaac ctgccctggt ggcgggccag   1440
ggacaagaac ggccaggaag gctacatccc cagcaactac gtgaccgagg ccgaggactc   1500
catcgagatg tacgagtggt acagcaagca catgaccaga agccaggccg aacagctgct   1560
gaagcaggaa ggcaaagagg gcggcttcat cgtccgggac agcagcaagg ccggcaagta   1620
caccgtgagc gtgttcgcca agagcaccgg cgacccccag ggcgtgatcc ggcactacgt   1680
ggtgtgcagc accccccaga gccagtacta cctggccgag aagcacctgt tcagcaccat   1740
ccccgagctg atcaactatc accagcacaa cagcgctgga ctgatttctc ggctgaagta   1800
ccccgtgtcc cagcagaaca aaaacgcccc cagcacagcc ggcctgggct acggcagctg   1860
ggagatcgac cccaaggacc tgaccttcct gaaagagctg ggcaccggcc agttcggcgt   1920
ggtgaagtac ggcaagtgga ggggccagta cgacgtggcc atcaagatga tcaaggaagg   1980
cagcatgagc gaggacgagt tcatcgagga agccaaagtg atgatgaacc tgagccacga   2040
gaagctggtg cagctgtacg gcgtgtgcac caagcagcgg cccatcttca tcatcaccga   2100
gtacatggcc aacggctgcc tgctgaacta cctgcgggag atgcggcaca ggttccagac   2160
acagcagctg ctcgaaatgt gcaaggacgt gtgcgaggct atggaatacc tggaatccaa   2220
gcagttcctg caccgggacc tggccgccag aaactgcctg gtgaacgacc agggggtggt   2280
gaaggtgtcc gacttcggcc tgagcagata cgtgctggac gacgagtaca ccagcagcgt   2340
gggcagcaag ttccccgtgc ggtggagccc ccctgaggtg ctgatgtaca gcaagttcag   2400
cagcaagagc gacatctggg ccttcggcgt gctgatgtgg gagatctaca gcctgggcaa   2460
gatgccctac gagcggttca ccaacagcga gaccgccgag cacatcgccc agggcctgcg   2520
gctgtacagg ccccacctgg ccagcgagaa ggtgtacacc atcatgtaca gctgctggca   2580
cgagaaggcc gacgagaggc ccaccttcaa gatcctgctg tccaacatcc tggacgtgat   2640
ggacgaggaa agctgagata atcaacctct ggattacaaa atttgtgaaa gattgactgg   2700
tattcttaac tatgttgctc cttttacgct atgtggatac gctgctttaa tgcctttgta   2760
tcatgctatt gcttcccgta tggctttcat tttctcctcc ttgtataaat cctggttagt   2820
```

```
tcttgccacg gcggaactca tcgccgcctg ccttgcccgc tgctggacag gggctcggct   2880
gttgggcact gacaattccg tggactagtg tcgactgctt tatttgtgaa atttgtgatg   2940
ctattgcttt atttgtaacc attataagct gcaataaaca agttaacaac aacaattgca   3000
ttcattttat gtttcaggtt cagggggagg tgtgggaggt tttttaaagg ggtaagtttc   3060
tcgactatga aaactgagtt tcaagatatc aaggacttgg ccttagatct ttcttgggga   3120
agaggtaaat tttcgttggt aggaggaggg gagtagaatg gacctaagtt ctttcaaatt   3180
cagcaaaata tttcctagcc tataactagc taaagccgga aagtcaaagg tcctaagaag   3240
ccacaaggaa aatattacca tggaatcttg gaattgatga gcactcatta aatgattgtt   3300
gaaaatgaaa tcgaagagtt ggaaattgct tccttacttc ctatgaggaa ggtacataca   3360
gtcattcact cttccatggt atttgccctc catttggtag tcatagattt atagatctgg   3420
aaggattttt ttttcttccc ccacatgaca ggtcctggtg ccacctcact ttgttgaatg   3480
attagataac aaaatctaat catctggttg cttaatccct cttaatcttt ctccattttc   3540
ttcctcattc tagagtagat aagtagcatg gcgggttaat cattaactac aaggaacccc   3600
tagtgatgga gttggccact ccctctctgc gcgctcgctc gctcactgag gccgggcgac   3660
caaaggtcgc ccgacgcccg ggctttgccc gggcggcctc agtgagcgag cgagcgcgcc   3720
agctggcgta atagcgaaga ggcccgcacc gatcgccctt cccaacagtt gcgcagcctg   3780
aatggcgaat ggcgattccg ttgcaatggc tggcggtaat attgttctgg atattaccag   3840
caaggccgat agtttgagtt cttctactca ggcaagtgat gttattacta atcaaagaag   3900
tattgcgaca acggttaatt tgcgtgatgg acagactctt ttactcggtg gcctcactga   3960
ttataaaaac acttctcagg attctggcgt accgttcctg tctaaaatcc ctttaatcgg   4020
cctcctgttt agctcccgct ctgattctaa cgaggaaagc acgttatacg tgctcgtcaa   4080
agcaaccata gtacgcgccc tgtagcggcg cattaagcgc ggcgggtgtg gtggttacgc   4140
gcagcgtgac cgctacactt gccagcgccc tagcgcccgc tcctttcgct ttcttccctt   4200
cctttctcgc cacgttcgcc ggctttcccc gtcaagctct aaatcggggg ctccctttag   4260
ggttccgatt tagtgcttta cggcacctcg accccaaaaa acttgattag ggtgatggtt   4320
cacgtagtgg gccatcgccc tgatagacgg tttttcgccc tttgacgttg gagtccacgt   4380
tctttaatag tggactcttg ttccaaactg gaacaacact caaccctatc tcggtctatt   4440
cttttgattt ataagggatt ttgccgattt cggcctattg gttaaaaaat gagctgattt   4500
aacaaaaatt taacgcgaat tttaacaaaa tattaacgtt tacaatttaa atatttgctt   4560
atacaatctt cctgtttttg gggcttttct gattatcaac cggggtacat atgattgaca   4620
tgctagtttt acgattaccg ttcatcgatt ctcttgtttg ctccagactc tcaggcaatg   4680
acctgatagc ctttgtagag acctctcaaa aatagctacc ctctccggca tgaatttatc   4740
agctagaacg gttgaatatc atattgatgg tgatttgact gtctccggcc tttctcaccc   4800
gtttgaatct ttacctacac attactcagg cattgcattt aaaatatatg agggttctaa   4860
aaatttttat ccttgcgttg aaataaaggc ttctcccgca aaagtattac agggtcataa   4920
tgtttttggt acaaccgatt tagctttatg ctctgaggct ttattgctta attttgctaa   4980
ttctttgcct tgcctgtatg atttattgga tgttggaatc gcctgatgcg gtattttctc   5040
cttacgcatc tgtgcggtat ttcacaccgc atatggtgca ctctcagtac aatctgctct   5100
gatgccgcat agttaagcca gccccgacac ccgccaacac ccgctgacgc gccctgacgg   5160
```

```
gcttgtctgc tcccggcatc cgcttacaga caagctgtga ccgtctccgg gagctgcatg   5220

tgtcagaggt tttcaccgtc atcaccgaaa cgcgcgagac gaaagggcct cgtgatacgc   5280

ctatttttat aggttaatgt catgataata atggtttctt agacgtcagg tggcactttt   5340

cggggaaatg tgcgcggaac ccctatttgt ttatttttct aaatacattc aaatatgtat   5400

ccgctcatga gacaataacc ctgataaatg cttcaataat attgaaaaag gaagagtatg   5460

agtattcaac atttccgtgt cgcccttatt ccctttttg cggcattttg ccttcctgtt   5520

tttgctcacc cagaaacgct ggtgaaagta aaagatgctg aagatcagtt gggtgcacga   5580

gtgggttaca tcgaactgga tctcaacagc ggtaagatcc ttgagagttt tcgccccgaa   5640

gaacgttttc caatgatgag cacttttaaa gttctgctat gtggcgcggt attatcccgt   5700

attgacgccg ggcaagagca actcggtcgc cgcatacact attctcagaa tgacttggtt   5760

gagtactcac cagtcacaga aaagcatctt acggatggca tgacagtaag agaattatgc   5820

agtgctgcca taaccatgag tgataacact gcggccaact tacttctgac aacgatcgga   5880

ggaccgaagg agctaaccgc ttttttgc                                       5908


<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25

gagcaaagac cccaacgaga                                                  20


<210> SEQ ID NO 26
<211> LENGTH: 22
<212> TYPE: DNA
<213> ORGANISM: Artificial Sequence
<220> FEATURE:
<223> OTHER INFORMATION: Synthetic construct

<400> SEQUENCE: 26

aggttttatg tctctcgctc cg                                               22


<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27

gcatggacga gctgtacaag                                                  20


<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28

atggtcagac ccagtgggtg                                                  20


<210> SEQ ID NO 29
<211> LENGTH: 21
<212> TYPE: DNA
<213> ORGANISM: Artificial Sequence
```

<220> FEATURE:
<223> OTHER INFORMATION: Synthetic construct

<400> SEQUENCE: 29
tgacaggtcc tggtgccacc t 21

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
aaagatttgc agagagatga gt 22

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
gccaagcaat gaagttttgt 20

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
cctgggcaac atagtgtgat c 21

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
tcctggttag ttcttgccac 20

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
agaaactgcc tggtgaacga c 21

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
ccccatctca gacattggtc 20

<210> SEQ ID NO 36
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 36

Asp Gly Gly Gly Ser
1 5

<210> SEQ ID NO 37
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 37

Thr Gly Glu Lys Pro
1 5

<210> SEQ ID NO 38
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 38

Gly Gly Arg Arg
1

<210> SEQ ID NO 39
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 39

Gly Gly Gly Gly Ser
1 5

<210> SEQ ID NO 40
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 40

Glu Gly Lys Ser Ser Gly Ser Gly Ser Glu Ser Lys Val Asp
1 5 10

<210> SEQ ID NO 41
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 41

Lys Glu Ser Gly Ser Val Ser Ser Glu Gln Leu Ala Gln Phe Arg Ser
1 5 10 15

Leu Asp

<210> SEQ ID NO 42
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 42

Gly Gly Arg Arg Gly Gly Gly Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 43

Leu Arg Gln Arg Asp Gly Glu Arg Pro
1               5

<210> SEQ ID NO 44
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 44

Leu Arg Gln Lys Asp Gly Gly Gly Ser Glu Arg Pro
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 45

Leu Arg Gln Lys Asp Gly Gly Gly Ser Gly Gly Gly Ser Glu Arg Pro
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 46

Glu Xaa Xaa Tyr Xaa Gln Xaa
1               5

<210> SEQ ID NO 47
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 47

Glu Asn Leu Tyr Phe Gln Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 48

Glu Asn Leu Tyr Phe Gln Ser
1               5

<210> SEQ ID NO 49
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 49

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 50
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 50

Ala Thr Asn Phe Ser Leu Leu Lys Gln Ala Gly Asp Val Glu Glu Asn
1               5                   10                  15

Pro Gly Pro

<210> SEQ ID NO 51
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Leu Leu Lys Gln Ala Gly Asp Val Glu Glu Asn Pro Gly Pro
1               5                   10

<210> SEQ ID NO 52
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Gly Ser Gly Glu Gly Arg Gly Ser Leu Leu Thr Cys Gly Asp Val Glu
1 5 10 15

Glu Asn Pro Gly Pro
20

<210> SEQ ID NO 53
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Glu Gly Arg Gly Ser Leu Leu Thr Cys Gly Asp Val Glu Glu Asn Pro
1 5 10 15

Gly Pro

<210> SEQ ID NO 54
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 54

Leu Leu Thr Cys Gly Asp Val Glu Glu Asn Pro Gly Pro
1 5 10

<210> SEQ ID NO 55
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 56
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Gln Cys Thr Asn Tyr Ala Leu Leu Lys Leu Ala Gly Asp Val Glu Ser
1 5 10 15

Asn Pro Gly Pro
20

<210> SEQ ID NO 57
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Leu Leu Lys Leu Ala Gly Asp Val Glu Ser Asn Pro Gly Pro
1 5 10

<210> SEQ ID NO 58
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 59
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Val Lys Gln Thr Leu Asn Phe Asp Leu Leu Lys Leu Ala Gly Asp Val
1 5 10 15

Glu Ser Asn Pro Gly Pro
20

<210> SEQ ID NO 60
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 60

Leu Leu Lys Leu Ala Gly Asp Val Glu Ser Asn Pro Gly Pro
1 5 10

<210> SEQ ID NO 61
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 61

Leu Leu Asn Phe Asp Leu Leu Lys Leu Ala Gly Asp Val Glu Ser Asn
1 5 10 15

Pro Gly Pro

<210> SEQ ID NO 62
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 62

Thr Leu Asn Phe Asp Leu Leu Lys Leu Ala Gly Asp Val Glu Ser Asn
1 5 10 15

Pro Gly Pro

<210> SEQ ID NO 63
<211> LENGTH: 14
<212> TYPE: PRT

<213> ORGANISM: Artificial Sequence
<220> FEATURE:
<223> OTHER INFORMATION: Self-cleaving polypeptide comprising 2A site

<400> SEQUENCE: 63

Leu Leu Lys Leu Ala Gly Asp Val Glu Ser Asn Pro Gly Pro
1 5 10

<210> SEQ ID NO 64
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 64

Asn Phe Asp Leu Leu Lys Leu Ala Gly Asp Val Glu Ser Asn Pro Gly
1 5 10 15

Pro

<210> SEQ ID NO 65
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 65

Gln Leu Leu Asn Phe Asp Leu Leu Lys Leu Ala Gly Asp Val Glu Ser
1 5 10 15

Asn Pro Gly Pro
20

<210> SEQ ID NO 66
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 66

Ala Pro Val Lys Gln Thr Leu Asn Phe Asp Leu Leu Lys Leu Ala Gly
1 5 10 15

Asp Val Glu Ser Asn Pro Gly Pro
20

<210> SEQ ID NO 67
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 67

Val Thr Glu Leu Leu Tyr Arg Met Lys Arg Ala Glu Thr Tyr Cys Pro
1 5 10 15

Arg Pro Leu Leu Ala Ile His Pro Thr Glu Ala Arg His Lys Gln Lys
20 25 30

Ile Val Ala Pro Val Lys Gln Thr
35 40

<210> SEQ ID NO 68
<211> LENGTH: 18
<212> TYPE: PRT

<213> ORGANISM: Artificial Sequence
<220> FEATURE:
<223> OTHER INFORMATION: Self-cleaving polypeptide comprising 2A site

<400> SEQUENCE: 68

Leu Asn Phe Asp Leu Leu Lys Leu Ala Gly Asp Val Glu Ser Asn Pro
1 5 10 15

Gly Pro

<210> SEQ ID NO 69
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 69

Leu Leu Ala Ile His Pro Thr Glu Ala Arg His Lys Gln Lys Ile Val
1 5 10 15

Ala Pro Val Lys Gln Thr Leu Asn Phe Asp Leu Leu Lys Leu Ala Gly
20 25 30

Asp Val Glu Ser Asn Pro Gly Pro
35 40

<210> SEQ ID NO 70
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 70

Glu Ala Arg His Lys Gln Lys Ile Val Ala Pro Val Lys Gln Thr Leu
1 5 10 15

Asn Phe Asp Leu Leu Lys Leu Ala Gly Asp Val Glu Ser Asn Pro Gly
20 25 30

Pro

<210> SEQ ID NO 71
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 71 gccrccatgg 10

<210> SEQ ID NO 72
<211> LENGTH: 18
<212> TYPE: DNA
<213> ORGANISM: Artificial Sequence
<220> FEATURE:
<223> OTHER INFORMATION: Synthetic construct

<400> SEQUENCE: 72
agctaaagcc ggaaagtc 18

<210> SEQ ID NO 73
<211> LENGTH: 23
<212> TYPE: DNA
<213> ORGANISM: Artificial Sequence
<220> FEATURE:
<223> OTHER INFORMATION: Synthetic construct

```
<400> SEQUENCE: 73

atgagtatga ctttgaacgt ggt                                              23


<210> SEQ ID NO 74
<211> LENGTH: 14
<212> TYPE: DNA
<213> ORGANISM: Artificial Sequence
<220> FEATURE:
<223> OTHER INFORMATION: Synthetic construct

<400> SEQUENCE: 74

gggggtaagt ttct                                                        14
```

TALEN-BASED AND CRISPR/Cas-BASED GENE EDITING FOR BRUTON'S TYROSINE KINASE

CROSS-REFERENCE TO RELATED APPLICATIONS

This application is a U.S. national phase application of PCT/US2019/029417, filed Apr. 26, 2019, which claims priority to U.S. Provisional Application No. 62/664,035, filed on Apr. 27, 2018, each of which is incorporated by reference herein in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SECH_001_01WO_ST25.txt, date recorded: Apr. 26, 2019, file size 75 kilobytes).

BACKGROUND

Technical Field

The present disclosure relates to improved gene editing compositions. More particularly, the disclosure relates to TALEN-based and CRISPR/Cas-based gene editing compositions, and methods of using the same, for editing the Bruton's tyrosine kinase (BTK) gene.

Description of the Related Art

X-linked agammaglobulinemia is a rare immunodeficiency caused by mutations in the Bruton's tyrosine kinase (BTK) gene. More than 600 different mutations in the BTK gene have been linked to X-linked agammaglobulinemia. Most of these mutations result in the absence of the BTK protein. Other mutations change a single protein building block (amino acid), which can lead to abnormal BTK protein production that is quickly broken down in the cell. BTK is required for the normal B maturation and activation, for BCR-mediated signaling, and for some signaling pathways in myeloid cells. Subjects lacking functional BTK have predominantly immature B cells, minimal antibody production, and are prone to recurrent and life-threatening infections.

Existing treatments include life-long intravenous immunoglobulin therapy, which lessens the severity of these infections, and judicious use of antibiotic therapy. Hematopoietic cell transplantation (HCT) is the only available approach with the potential of providing a cure for XLA. However, most XLA patients are not treated with this approach due to the difficult of finding HLA-matched donors and potential toxicities associated with GvHD. Despite significant improvements in transplant survival, the risk of treatment-related mortality has been a barrier to allo-HCT for XLA. Integrating self-inactivating lentiviral vectors (LV) encoding BTK cDNA under the control of the native proximal BTK gene promoter have been developed and evaluated in mouse model of human XLA. However, there are significant risks of insertional mutagenesis and gene expression disregulation associated with retroviral and LV-based gene therapies.

BRIEF SUMMARY

The present disclosure generally relates, in part, to TALEN-based or CRISPR-based gene editing systems that mediate gene editing of the human BTK gene, and methods of using the same.

In various embodiments, a gene editing composition comprises a TALEN that cleaves a target site in the human Bruton's tyrosine kinase (BTK) gene.

In certain embodiments, the TALEN comprises a TAL effector domain having RVDs selected from the group comprising:

a) T1-FRVDs HD NG HD NN NI HD NG NI NG NN NI NI NI NI HD NG;
b) T1-R RVDs HD NG NI NI NN NN HD HD NI NI NN NG HD HD NG;
c) T2-F RVDs NI NG HD NI NI NN NN NI HD NG NG NN NN HD HD NG;
d) T2-R RVDs NI HD HD NI NI HD NN NI NI NI NING NG NG NI HD HD NG;
e) T3-F RVDs NI NG NG NG HD HD NG NI NN HD HD NG NI NG NI NI HD NG;
f) T3-R RVDs NN NN HD NG NG HD NG NG NI NN NN NI HD HD NG NG NG;
g) T4-F RVDs HD HD NI NG NG NG NN NI NI NI HD NG NI NN NN NG; and
h) T4-R RVDs HD HD NG HD NI NG HD HD HD NG HD NG NG NN NN NG NG; and the TAL effector domain is capable of binding target site T1, T2, T3, or T4.

In various embodiments, a gene editing composition comprises a Cas protein or a polynucleotide encoding a Cas protein; a guide-RNA (gRNA); and a repair template comprising a functional BTK gene or fragment thereof; and the gene editing system is capable of repairing an endogenous BTK gene in the B cell or inserting a functional BTK gene into the genome of the B cell.

In certain embodiments, the gRNA comprises a nucleotide sequence set forth in SEQ ID NOs: 9-17.

In various embodiments, a polynucleotide encodes a gene editing composition contemplated herein.

In various embodiments, a mRNA encodes a gene editing composition contemplated herein.

In various embodiments, a cDNA encodes a gene editing composition contemplated herein.

In various embodiments, a vector comprises a polynucleotide encodes a gene editing composition contemplated herein.

In various embodiments, a cell comprises a polynucleotide encoding a gene editing composition contemplated herein.

In various embodiments, a cell comprising a mRNA encoding a gene editing composition contemplated herein.

In various embodiments, a cell comprises a vector comprises a polynucleotide encodes a gene editing composition contemplated herein.

In various embodiments, a cell comprises one or more genome modifications contemplated herein.

In certain embodiments, the cell is a hematopoietic cell.

In certain embodiments, the cell is a hematopoietic stem or progenitor cell.

In certain embodiments, the cell is a $CD34^+$ cell.

In certain embodiments, the cell is a $CD133^+$ cell.

In further embodiments, a composition comprises a cell contemplated herein.

In particular embodiments, the composition further comprises a physiologically acceptable carrier.

In various embodiments, a method of editing a BTK gene in a cell comprises introducing one or more of the gene editing compositions, polynucleotides, and vectors contemplated herein, and a donor repair template into the cell, wherein expression of the gene editing composition creates a double strand break at a target site in a BTK gene and the donor repair template is incorporated into the BTK gene by homology directed repair (HDR) at the site of the double-strand break (DSB).

In certain embodiments, the BTK gene comprises one or more amino acid mutations or deletions that result in X-linked agammaglobulinemia (XLA).

In particular embodiments, the cell is a hematopoietic cell.

In particular embodiments, the cell is a hematopoietic stem or progenitor cell.

In particular embodiments, the cell is a $CD34^+$ cell.

In particular embodiments, the cell is a $CD133^+$ cell.

In particular embodiments, the polynucleotide encodes the polypeptide is an mRNA.

In particular embodiments, the polynucleotide encodes a 5'-3' exonuclease is introduced into the cell.

In further embodiments, a polynucleotide encoding Trex2 or a biologically active fragment thereof is introduced into the cell.

In some embodiments, the donor repair template comprises a 5' homology arm homologous to a BTK gene sequence 5' of the DSB, a donor polynucleotide, and a 3' homology arm homologous to a BTK gene sequence 3' of the DSB.

In various embodiments, the donor polynucleotide is designed to repair one or more amino acid mutations or deletions in the BTK gene.

In particular embodiments, the donor polynucleotide comprises a cDNA encoding a BTK polypeptide.

In further embodiments, the donor polynucleotide comprises an expression cassette comprising a promoter operable linked to a cDNA encoding a BTK polypeptide.

In particular embodiments, the lengths of the 5' and 3' homology arms are independently selected from about 100 bp to about 2500 bp.

In various embodiments, the lengths of the 5' and 3' homology arms are independently selected from about 600 bp to about 1500 bp.

In some embodiments, the 5'homology arm is about 1500 bp and the 3' homology arm is about 1000 bp.

In certain embodiments, the 5'homology arm is about 600 bp and the 3' homology arm is about 600 bp.

In further embodiments, a viral vector is used to introduce the donor repair template into the cell.

In certain embodiments, the viral vector is a recombinant adeno-associated viral vector (rAAV) or a retrovirus.

In various embodiments, the rAAV has one or more ITRs from AAV2.

In further embodiments, the rAAV has a serotype selected from the group consisting of: AAV1, AAV2, AAV3, AAV4, AAV5, AAV6, AAV7, AAV8, AAV9, and AAV10.

In particular embodiments, the rAAV has an AAV2 or AAV6 serotype.

In some embodiments, the retrovirus is a lentivirus.

In certain embodiments, the lentivirus is an integrase deficient lentivirus (IDLV).

In particular embodiments, a method of treating, preventing, or ameliorating at least one symptom of X-linked agammaglobulinemia (XLA), or condition associated therewith, comprises harvesting a population of cells from the subject; editing the population of cells according to a method of editing a BTK gene contemplated herein, and administering the edited population of cells to the subject.

BRIEF DESCRIPTION OF THE SEQUENCE IDENTIFIERS

Figure 1A:
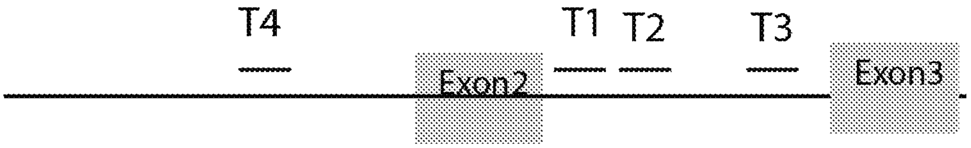
FIG. 1A shows a schematic of the BTK locus annotated with the location of the TALENs (T1-T4) cleavage sites within the human BTK gene. Schema is not drawn to scale.

- SEQ ID NOs: 1-8 are TALEN target sites in the first and second introns of the human BTK gene.
- SEQ ID NOs: 9-17 are gRNA sequences G1-G9.
- SEQ ID NO: 18 is an amino acid sequence of a human BTK polypeptide.
- SEQ ID NOs: 19-24 are the sequences of an AAV targeting vectors for BTK locus.
- SEQ ID NOs: 25-35 are oligos and probes used for determining HDR in $CD34^+$ cells either using RNP or TALEN plus AAV.MND.GFP vectors or using RNPs and ATG.coBTK expressing AAV vectors.

DETAILED DESCRIPTION

A. Overview

The present disclosure generally relates to, in part, improved genome editing compositions and methods of use thereof. Without wishing to be bound by any particular theory, the genome editing compositions contemplated herein are used to increase the amount of Bruton's tyrosine kinase (BTK) in a cell to treat, prevent, or ameliorate symptoms associated with X-linked agammaglobulinemia (XLA). Thus, the compositions contemplated herein offer a potentially curative solution to subjects that have XLA. Without wishing to be bound to any particular theory, it is contemplated that a gene editing approach that introduces a polynucleotide encoding a functional BTK protein into a BTK gene that has one or more mutations and/or deletions that leads to XLA, will rescue the immunologic and functional deficits caused by XLA and to provide a potentially curative therapy.

In various embodiments, genome editing strategies, compositions, genetically modified cells, and methods of use thereof to increase or restore BTK function are contemplated. Without wishing to be bound by any particular theory, it is contemplated that genome editing of the BTK gene to introduce a polynucleotide encoding a functional copy of the BTK protein. In one embodiment, editing the BTK gene comprises introducing a polynucleotide encoding a functional copy of the BTK protein in such a way that it is under control of the endogenous promoter and enhancer in hematopoietic stem cells (HSC). Restoration of functional BTK in immune cells will effectively treat, prevent, and/or ameliorate one or more symptoms associated with subjects that have XLA.

Genome editing methods contemplated in various embodiments comprise TALEN (Transcription activator-like effector nuclease) variants designed to bind and cleave a target binding site in the BTK gene. The TALEN variants contemplated in particular embodiments, can be used to introduce a double-strand break in a target polynucleotide sequence, and in the presence of a polynucleotide template, e.g., a donor repair template, result in homology directed repair (HDR), i.e., homologous recombination of the donor repair template into the BTK gene. TALEN variants contemplated in certain embodiments, can also be designed as nickases, which generate single-stranded DNA breaks that can be repaired using the cell's base-excision-repair (BER) machinery or homologous recombination in the presence of a donor repair template. Homologous recombination requires homologous DNA as a template for repairing the double-stranded DNA break and can be leveraged to create a limitless variety of modifications specified by the introduction of donor DNA comprising an expression cassette or polynucleotide encoding a therapeutic gene, e.g., BTK, at the target site, flanked on either side by sequences bearing homology to regions flanking the target site.

Genome editing methods contemplated in various other embodiments comprise CRISPR/Cas systems designed to bind and cleave a target binding site in the BTK gene. The CRISPR/Cas systems contemplated in particular embodiments, can be used to introduce a double-strand break in a target polynucleotide sequence, and in the presence of a polynucleotide template, e.g., a donor repair template, result in homology directed repair (HDR), i.e., homologous recombination of the donor repair template into the BTK gene. CRISPR/Cas systems complemplated in certain embodiments can also be guided to one or more cleavage sites by one or more guide RNAs (gRNAs). CRISPR/Cas systems contemplated in certain embodiments, can also be designed as nickases, which generate single-stranded DNA breaks that can be repaired using the cell's base-excision-repair (BER) machinery or homologous recombination in the presence of a donor repair template. Homologous recombination requires homologous DNA as a template for repairing the double-stranded DNA break and can be leveraged to create a limitless variety of modifications specified by the introduction of donor DNA comprising an expression cassette or polynucleotide encoding a therapeutic gene, e.g., BTK, at the target site, flanked on either side by sequences bearing homology to regions flanking the target site.

In one preferred embodiment, the genome editing compositions contemplated herein comprise a Transcription activator-like effector nucleases (TALEN) that target the human BTK gene.

In one preferred embodiment, the genome editing compositions contemplated herein comprise a CRISPR (Clustered Regularly Interspaced Short Palindromic Repeats)/Cas (CRISPR Associated) nuclease systems that target the human BTK gene. In such embodiments, the site-directed nuclease is a CRISPR-associated endonuclease (a "Cas "endonuclease") and the nucleic acid guide molecule is a guide RNA (gRNA).

In various embodiments, wherein a DNA break is generated in the first or second intron of the BTK gene and a donor repair template, i.e., a donor repair template, comprising a polynucleotide encoding a functional BTK polypeptide is provided, the DSB is repaired with the sequence of the template by homologous recombination at the DNA breaksite. In preferred embodiments, the repair template comprises a polynucleotide sequence that encodes a functional BTK polypeptide designed to be inserted at a site where the expression of the polynucleotide and BTK polypeptide is under the control of the endogenous BTK promoter and/or enhancers.

In one preferred embodiment, the genome editing compositions contemplated herein comprise TALEN variants and one or more end-processing enzymes to increase HDR efficiency.

In one preferred embodiment, the genome editing compositions contemplated herein comprise a TALEN or CRISPR/Cas nuclease system that targets a human BTK gene, a donor repair template encoding a functional BTK protein, and an end-processing enzyme, e.g., Trex2.

In various embodiments, genome edited cells are contemplated. The genome edited cells comprise a functional BTK polypeptide, rescue B cell development, and prevent XLA.

Accordingly, the methods and compositions contemplated herein represent a quantum improvement compared to existing gene editing strategies for the treatment of XLA.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in*

*Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols* (*Methods in Molecular Biology*) (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir andCC Blackwell, eds., 1986); Roitt, *Essential Immunology,* 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology.*

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of' indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a TALEN variant, genome editing composition, or genome edited cell contemplated herein to produce, elicit, or cause a greater response (i.e., physiological response) compared to the response caused by either vehicle or control. A measurable response may include an increase in HDR, and/or BTK expression, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of TALEN variant, CRISPR/Cas system, genome editing composition, or genome edited cell contemplated herein to produce, elicit, or cause a lesser response (i.e., physiological response) compared to the response caused by either vehicle or control. A measurable response may include a decrease in one or more symptoms associated with XLA. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a TALEN variant, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of TALEN variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, a TALEN selectively binds an on-target DNA binding site about 5, 10, 15, 20, 25, 50, 100, or 1000 times more frequently than the TALEN binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a TALEN variant or CRISPR/Cas system is double-standed and comprises the reference sequence and its complement. In a preferred embodiment, the target site is a sequence in the human BTK gene.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and TALENs variants, e.g., TALENs, etc. contemplated herein are used for targeted double-stranded DNA cleavage. Endonuclease cleavage recognition sites may be on either DNA strand or both DNA strands.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, IRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extrachromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more TALEN variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

C. TALEN-Based Systems

TALEN variants contemplated in particular embodiments herein that are suitable for genome editing a target site in the BTK gene comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," "nuclease variant," or "TALEN variant" are used interchangeably and refer to a TALEN comprising one or more DNA binding domains and one or more DNA cleavage domains, wherein the TALEN has been designed and/or modified from a parental or naturally occurring TALEN, to bind and cleave a double-stranded DNA target sequence in a BTK gene, preferably a target sequence in the first or second intron of the human BTK gene, and more preferably a target sequence in the first or second intron of the human BTK gene as set forth in SEQ ID NOS: 1-8. The TALEN variant may be designed and/or modified from a naturally occurring effector domain or from a previous TALEN variant. TALEN variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerase or template-independent DNA polymerase activity.

In various embodiments, a TALEN is reprogrammed to introduce double-strand breaks (DSBs) in a BTK gene, preferably a target sequence in the first or second intron of the human BTK gene, and more preferably a target sequence in the first or second intron of the human BTK gene as set forth in SEQ ID NOS: 1-8. "TALEN" refers to a protein comprising a TAL effector DNA binding domain and an enzymatic domain. They are made by fusing a TAL effector DNA-binding domain to a DNA cleavage domain (a nuclease which cuts DNA strands). The FokI restriction enzyme described above is an exemplary enzymatic domain suitable for use in TALEN-based gene regulating systems.

TAL effectors are proteins that are secreted by *Xanthomonas* bacteria via their type III secretion system when they infect plants. The DNA binding domain contains a repeated, highly conserved, 33-34 amino acid sequence with divergent 12th and 13th amino acids. These two positions, referred to as the Repeat Variable Diresidue (RVD), are highly variable and strongly correlated with specific nucleotide recognition. Therefore, the TAL effector domains can be engineered to bind specific target DNA sequences by selecting a combination of repeat segments containing the appropriate RVDs. The nucleic acid specificity for RVD combinations is as follows: HD targets cytosine, NI targets adenenine, NG targets thymine, and NN targets guanine (though, in some embodiments, NN can also bind adenenine with lower specificity).

In some embodiments, the TAL effector domains bind to a target DNA sequence that is at least 90% identical to a target DNA sequence within a target locus of the BTK gene. In some embodiments, the TAL effector domains bind to a target DNA sequence that is at least 95%, 96%, 97%, 98%, or 99% identical to a target DNA sequence within a target locus of a target gene selected those listed in Table 1. In some embodiments, the TAL effector domains bind to a target DNA sequence that is 100% identical to a target DNA sequence within a target locus of a target gene selected those listed in Table 1.

In some embodiments, the TAL effector domains bind to a target DNA sequence that is at least 90% identical to a target DNA sequence within a target locus within an exon or within an intron of the BTK gene, preferably within the second or third exon of the BTK gene. In some embodiments, the TAL effector domains bind to a target DNA sequence that is at least 95%, 96%, 97%, 98%, or 99% identical to a target DNA sequence within a target locus within an exon or within an intron of the BTK gene, preferably within the second or third exon of the BTK gene. In some embodiments, the TAL effector domains bind to a target DNA sequence that is 100% identical to a target DNA sequence within a target locus within an exon or within an intron of the BTK gene, preferably within the second or third exon of the BTK gene.

In some embodiments, the TAL effector domains bind to a target DNA sequence that is at least 90% identical to one of SEQ ID NOS: 1-8. In some embodiments, the TAL effector domains bind to a target DNA sequence that is at least 95%, 96%, 97%, 98%, or 99% identical to one of SEQ ID NOS: 1-8. In some embodiments, the TAL effector domains bind to a target DNA sequence that is 100% identical to one of SEQ ID NOS: 1-8.

In some embodiments, the TAL effector domains bind to a target DNA sequence that is at least 90% identical to a target DNA sequence within a target locus of the BTK gene. In some embodiments, the TAL effector domains bind to a target DNA sequence that is at least 95%, 96%, 97%, 98%, or 99% identical to a target DNA sequence within a target locus of a target gene selected those listed in Table 1. In some embodiments, the TAL effector domains bind to a target DNA sequence that is 100% identical to a target DNA sequence within a target locus of a target gene selected those listed in Table 1.

TABLE 1

| Target Sites | |
|---|---|
| SEQ ID NO: 1 TALEN 1-F target site | TCTCGACTATGAAAACT |
| SEQ ID NO: 2 TALEN 1-R target site | TCTAAGGCCAAGTCCT |
| SEQ ID NO: 3 TALEN 2-F target site | TATCAAGGACTTGGCCT |
| SEQ ID NO: 4 TALEN 2-R target site | TACCAACGAAAATTTACCT |
| SEQ ID NO: 5 TALEN 3-F target site | TATTTCCTAGCCTATAACT |
| SEQ ID NO: 6 TALEN 3-R target site | TGGCTTCTTAGGACCTTT |
| SEQ ID NO: 7 TALEN 4-F target site | CCATTTGAAACTAGGT |
| SEQ ID NO: 8 TALEN 4-R target site | CCTCATCCCTCTTGGTT |

In some embodiments, the TAL effector domains bind to a target DNA sequence that is at least 90% identical to a target DNA sequence within a target locus within an exon or within an intron of the BTK gene, preferably within the second or third exon of the BTK gene. In some embodiments, the TAL effector domains bind to a target DNA sequence that is at least 95%, 96%, 97%, 98%, or 99% identical to a target DNA sequence within a target locus within an exon or within an intron of the BTK gene, preferably within the second or third exon of the BTK gene. In some embodiments, the TAL effector domains bind to a target DNA sequence that is 100% identical to a target DNA sequence within a target locus within an exon or within an intron of the BTK gene, preferably within the second or third exon of the BTK gene.

In some embodiments, the TAL effector domains bind to a target DNA sequence that is at least 90% identical to one of SEQ ID NOS: 1-8. In some embodiments, the TAL effector domains bind to a target DNA sequence that is at least 95%, 96%, 97%, 98%, or 99% identical to one of SEQ ID NOS: 1-8. In some embodiments, the TAL effector domains bind to a target DNA sequence that is 100% identical to one of SEQ ID NOS: 1-8.

In some embodiments, the gene editing composition comprises two or more TAL effector-fusion proteins each comprising a TAL effector domain, wherein at least one of the TAL effector domains bind to a target DNA sequence that is at least 90% identical to a target DNA sequence within a target locus of the BTK gene. In some embodiments, the gene editing composition comprises two or more TAL effector-fusion proteins each comprising a TAL effector domain, wherein at least one of the TAL effector domains bind to a target DNA sequence that is at least 95%, 96%, 97%, 98%, or 99% identical to a target DNA sequence within a target locus of a target gene selected those listed in Table 1. In some embodiments, the gene editing composition comprises two or more TAL effector-fusion proteins each comprising a TAL effector domain, wherein at least one of the TAL effector domains bind to a target DNA sequence that is 100% identical to a target DNA sequence within a target locus of a target gene selected those listed in Table 1. In some embodiments, the gene editing composition comprises two or more TAL effector-fusion proteins each comprising a TAL effector domain, wherein at least one of the TAL effector domains bind bind to a target DNA sequence that is at least 90% identical to a target DNA sequence within a target locus within an exon or within an intron of the BTK gene, preferably within the second or third exon of the BTK gene. In some embodiments, the gene editing composition comprises two or more TAL effector-fusion proteins each comprising a TAL effector domain, wherein at least one of the TAL effector domains bind to a target DNA sequence that is at least 95%, 96%, 97%, 98%, or 99% identical to a target DNA sequence within a target locus within an exon or within an intron of the BTK gene, preferably within the second or third exon of the BTK gene. In some embodiments, the gene editing composition comprises two or more TAL effector-fusion proteins each comprising a TAL effector domain, wherein at least one of the TAL effector domains bind to a target DNA sequence that is 100% identical to a target DNA sequence within a target locus within an exon or within an intron of the BTK gene, preferably within the second or third exon of the BTK gene.

In some embodiments, the gene editing composition comprises two or more TAL effector-fusion proteins each comprising a TAL effector domain, wherein at least one of the TAL effector domains bind to a target DNA sequence that is at least 90% identical to one of SEQ ID NOS: 1-8. In some embodiments, the gene editing composition comprises two or more TAL effector-fusion proteins each comprising a TAL effector domain, wherein at least one of the TAL effector domains bind to a target DNA sequence that is at least 95%, 96%, 97%, 98%, or 99% identical to one of SEQ ID NOS: 1-8. In some embodiments, the gene editing composition comprises two or more TAL effector-fusion proteins each comprising a TAL effector domain, wherein at least one of the TAL effector domains bind to a target DNA sequence that is 100% identical to one of SEQ ID NOS: 1-8.

In some embodiments, the TAL effectors domain comprises RVD sequences as shown in Table 2.

TABLE 2

| TAL effector domain RVDs | |
|---|---|
| T1 (#1181) | |
| T1-F RVDs | HD NG HD NN NI HD NG NI NG NN NI NI NI NI HD NG |
| T1-R RVDs | HD NG NI NI NN NN HD HD NI NI NN NG HD HD NG |
| T2 (#1182) | |
| T2-F RVDs | NI NG HD NI NI NN NN NI HD NG NG NN NN HD HD NG |
| T2-R RVDs | NI HD HD NI NI HD NN NI NI NI NI NG NG NG NI HD HD NG |
| T3 (#1183) | |
| T3-F RVDs | NI NG NG NG HD HD NG NI NN HD HD NG NI NG NI NI HD NG |
| T3-R RVDs | NN NN HD NG NG HD NG NG NI NN NN NI HD HD NG NG NG |
| T4 | |
| T4-F RVDs | HD HD NI NG NG NG NN NI NI NI HD NG NI NN NN NG |
| T4-R RVDs | HD HD NG HD NI NG HD HD HD NG HD NG NG NN NN NG NG |

Methods and compositions for assembling the TAL-effector repeats are known in the art. See e.g., Cermak et al, Nucleic Acids Research, 39:12, 2011, e82. Plasmids for constructions of the TAL-effector repeats are commercially available from Addgene.

D. CRISPR/Cas-Based Systems

Combination gene-regulating systems comprise a site-directed modifying polypeptide and a nucleic acid guide molecule. Herein, a "site-directed modifying polypeptide" refers to a polypeptide that binds to a nucleic acid guide molecule, is targeted to a target nucleic acid sequence, such as, for example, a DNA sequence, by the nucleic acid guide molecule to which it is bound, and modifies the target DNA sequence (e.g., cleavage, mutation, or methylation of target DNA). A site-directed modifying polypeptide comprises two portions, a portion that binds the nucleic acid guide and an activity portion. In some embodiments, a site-directed modifying polypeptide comprises an activity portion that exhibits site-directed enzymatic activity (e.g., DNA methylation, DNA cleavage, histone acetylation, histone methylation, etc.), wherein the site of enzymatic activity is determined by the guide nucleic acid. In some cases, a site-directed modifying polypeptide has enzymatic activity that modifies target DNA (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). In other cases, a site-directed modifying polypeptide has enzymatic activity that modifies a polypeptide (e.g., a histone) associated with target DNA (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity). In some embodiments, the activity portion modulates transcription of the target DNA sequence (e.g., to increase or decrease transcription).

The nucleic acid guide comprises two portions: a first portion that is complementary to, and capable of binding with, an endogenous target DNA sequence (referred to herein as a "DNA-binding segment"), and a second portion that is capable of interacting with the site-directed modifying polypeptide (referred to herein as a "protein-binding segment"). In some embodiments, the DNA-binding segment and protein-binding segment of a nucleic acid guide are comprised within a single polynucleotide molecule. In some embodiments, the DNA-binding segment and protein-binding segment of a nucleic acid guide are each comprised within separate polynucleotide molecules, such that the nucleic acid guide comprises two polynucleotide molecules that associate with each other to form the functional guide.

The nucleic acid guide mediates the target specificity of the combined protein/nucleic gene regulating systems by specifically hybridizing with a target DNA sequence comprised within the DNA sequence of a target gene. Reference herein to a target gene encompasses the full-length DNA sequence for that particular gene and a full-length DNA sequence for a particular target gene will comprise a plurality of target genetic loci, which refer to portions of a particular target gene sequence (e.g., an exon or an intron). Within each target genetic loci are shorter stretches of DNA sequences referred to herein as "target DNA sequences" or "target sequences" that can be modified by the gene-regulating systems described herein. Further, each target genetic loci comprises a "target modification site," which refers to the precise location of the modification induced by the gene-regulating system (e.g., the location of an insertion, a deletion, or mutation, the location of a DNA break, or the location of an epigenetic modification). The gene-regulating systems described herein may comprise a single nucleic acid guide, or may comprise a plurality of nucleic acid guides (e.g., 2, 3, 4, 5, 6, 7, 8, 9, 10, or more nucleic acid guides).

The CRISPR/Cas systems described below are exemplary embodiments of a combination protein/nucleic acid system.

In some embodiments, the gene editing systems described herein are CRISPR (Clustered Regularly Interspaced Short Palindromic Repeats)/Cas (CRISPR Associated) nuclease systems. In such embodiments, the site-directed modifying polypeptide is a CRISPR-associated endonuclease (a "Cas" endonuclease) and the nucleic acid guide molecule is a guide RNA (gRNA).

A Cas polypeptide refers to a polypeptide that can interact with a gRNA molecule and, in concert with the gRNA molecule, homes or localizes to a target DNA sequence and includes naturally occurring Cas proteins and engineered, altered, or otherwise modified Cas proteins that differ by one or more amino acid residues from a naturally-occurring Cas sequence.

In some embodiments, the Cas protein is a Cas9 protein. Cas9 is a multi-domain enzyme that uses an HNH nuclease domain to cleave the target strand of DNA and a RuvC-like domain to cleave the non-target strand. In some embodiments, mutants of Cas9 can be generated by selective domain inactivation enabling the conversion of WT Cas9 into an enzymatically inactive mutant (e.g., dCas9), which is unable to cleave DNA, or a nickase mutant, which is able to produce single-stranded DNA breaks by cleaving one or the other of the target or non-target strand.

A guide RNA (gRNA) comprises two segments, a DNA-binding segment and a protein-binding segment. In some embodiments, the protein-binding segment of a gRNA is comprised in one RNA molecule and the DNA-binding segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The protein-binding segment of a gRNA comprises, in part, two complementary stretches of nucleotides that hybridize to one another to form a double stranded RNA duplex (dsRNA duplex), which facilitates binding to the Cas protein.

The DNA-binding segment (or "DNA-binding sequence") of a gRNA comprises a nucleotide sequence that is complementary to and capable of binding to a specific sequence target DNA sequence. The protein-binding segment of the gRNA interacts with a Cas polypeptide and the interaction of the gRNA molecule and site-directed modifying polypeptide results in Cas binding to the endogenous DNA and produces one or more modifications within or around the target DNA sequence. The precise location of the target modification site is determined by both (i) base-pairing complementarity between the gRNA and the target DNA sequence; and (ii) the location of a short motif, referred to as the protospacer adjacent motif (PAM), in the target DNA sequence. The PAM sequence is required for Cas binding to the target DNA sequence. A variety of PAM sequences are known in the art and are suitable for use with a particular Cas endonuclease (e.g., a Cas9 endonuclease) are known in the art (See e.g., Nat Methods. 2013 November; 10(11): 1116-1121 and Sci Rep. 2014; 4:5405). In some embodiments, the PAM sequence is located within 50 base pairs of the target modification site. In some embodiments, the PAM sequence is located within 10 base pairs of the target modification site. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

Cas Proteins

In some embodiments, the site-directed modifying polypeptide is a Cas protein. Cas molecules of a variety of species can be used in the methods and compositions described herein, including Cas molecules derived from *S. pyogenes, S. aureus, N. meningitidis*, S. thermophiles, Acidovorax *avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae*.

In some embodiments, the Cas protein is a Cas9 protein or a Cas9 ortholog and is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the endonuclease is selected from the group consisting of C2C1, C2C3, Cpf1 (also referred to as Cas12a), Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. Additional Cas9 orthologs are described in International PCT Publication No. WO 2015/071474.

In some embodiments, the Cas9 protein is a naturally-occurring Cas9 protein. Exemplary naturally occurring Cas9 molecules are described in Chylinski et al., RNA Biology 2013 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 1 1 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

In some embodiments, a Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, a Cas polypeptide comprises one or more of the following activities:

a) a nickase activity, i.e., the ability to cleave a single strand, e.g., the non-complementary strand or the complementary strand, of a nucleic acid molecule;
b) a double stranded nuclease activity, i.e., the ability to cleave both strands of a double stranded nucleic acid and create a double stranded break, which in an embodiment is the presence of two nickase activities;
c) an endonuclease activity;
d) an exonuclease activity; and/or
e) a helicase activity, i.e., the ability to unwind the helical structure of a double stranded nucleic acid.

In some embodiments, the Cas9 is a wildtype (WT) Cas9 protein or ortholog. WT Cas9 comprises two catalytically active domains (HNH and RuvC). Binding of WT Cas9 to DNA based on gRNA specificity results in double-stranded DNA breaks that can be repaired by non-homologous end joining (NHEJ) or homology-directed repair (HDR). In some embodiments, Cas9 is fused to heterologous proteins that recruit DNA-damage signaling proteins, exonucleases, or phosphatases to further increase the likelihood or the rate of repair of the target sequence by one repair mechanism or another. In some embodiments, a WT Cas9 is co-expressed with a nucleic acid repair template to facilitate the incorporation of an exogenous nucleic acid sequence by homology-directed repair.

In some embodiments, different Cas9 proteins (i.e., Cas9 proteins from various species) may be advantageous to use in the various provided methods in order to capitalize on various enzymatic characteristics of the different Cas9 proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from *S. pyogenes* and recognizes the PAM sequence motif NGG, NAG, NGA (*Mali* et al, Science 2013; 339 (6121): 823-826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J BACTERIOL 2008; 190 (4): 1390-1400). In some embodiments, the Cas protein is a Cas9 protein derived from *S. mutans* and recognizes the PAM sequence motif NGG and/or NAAR (R=A or G) (See, e.g., Deveau et al, J BACTERIOL 2008; 190 (4): 1390-1400). In some embodiments, the Cas protein is a Cas9 protein derived from *S. aureus* and recognizes the PAM sequence motif NNGRR (R=A or G). In some embodiments, the Cas protein is a Cas9 protein derived from *S. aureus* and recognizes the PAM sequence motif N GRRT (R=A or G). In some embodiments, the Cas protein is a Cas9 protein derived from *S. aureus* and recognizes the PAM sequence motif N GRRV (R=A or G). In some embodiments, the Cas protein is a Cas9 protein derived from *N. meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T.

In some embodiments, a polynucleotide encoding a Cas protein is provided. In some embodiments, the polynucleotide encodes a Cas protein that is at least 90% identical to a Cas protein described in International PCT Publication No. WO 2015/071474 or Chylinski et al., RNA Biology 2013 10:5, 727-737. In some embodiments, the polynucleotide encodes a Cas protein that is at least 95%, 96%, 97%, 98%, or 99% identical to a Cas protein described in International PCT Publication No. WO 2015/071474 or Chylinski et al., RNA Biology 2013 10:5, 727-737. In some embodiments, the polynucleotide encodes a Cas protein that is 100% identical to a Cas protein described in International PCT Publication No. WO 2015/071474 or Chylinski et al., RNA Biology 2013 10:5, 727-737.

Cas Mutants

In some embodiments, the Cas polypeptides are engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild-type Cas protein.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a Cas nickase mutant. Cas nickase mutants comprise only one catalytically active domain (either the HNH domain or the RuvC domain). The Cas nickase mutants retain DNA binding based on gRNA specificity, but are capable of cutting only one strand of DNA resulting in a single-strand break (e.g. a "nick"). In some embodiments, two complementary Cas nickase mutants (e.g., one Cas nickase mutant with an inactivated RuvC domain, and one Cas nickase mutant with an inactivated HINH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas nickase mutant is co-expressed with a nucleic acid repair template to facilitate the incorporation of an exogenous nucleic acid sequence by homology-directed repair.

In some embodiments, the Cas is a deactivated Cas (dCas) mutant. In such embodiments, the Cas polypeptide does not comprise any intrinsic enzymatic activity and is unable to mediate DNA cleavage. In such embodiments, the dCas may be fused with a heterologous protein that is capable of modifying the DNA in a non-cleavage based manner. For example, in some embodiments, a dCas protein is fused to transcription activator or transcription repressor domains (e.g., the Kruppel associated box (KRAB or SKD); the Mad mSIN3 interaction domain (SID or SID4X); the ERF repressor domain (ERD); the MAX-interacting protein 1 (MXI1); etc). In some such cases, the dCas fusion protein is targeted by the guide RNA to a specific location (i.e., sequence) in the target DNA and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, the Cas polypeptides described herein can be engineered to alter the PAM specificity of the Cas polypeptide. In some embodiments, a mutant Cas polypeptide has a PAM specificity that is different from the PAM specificity of the parental Cas polypeptide. For example, a naturally occurring Cas protein can be modified to alter the PAM sequence that the mutant Cas polypeptide recognizes to decrease off target sites, improve specificity, or eliminate a PAM recognition requirement. In some embodiments, a Cas protein can be modified to increase the length of the PAM recognition sequence. In some embodiments, the length of the PAM recognition sequence is at least 4, 5, 6, 7, 8, 9, 10 or 15 amino acids in length. Cas polypeptides that recognize different PAM sequences and/or have reduced off-target activity can be generated using directed evolution. Exemplary methods and systems that can be used for directed evolution of Cas polypeptides are described, e.g., in Esvelt et al. Nature 2011, 472(7344): 499-503.

Exemplary Cas mutants are described in International PCT Publication No. WO 2015/161276, which is incorporated herein by reference in its entirety.

gRNAS

The present disclosure provides guide RNAs (gRNAs) that direct a site-directed modifying polypeptide to a specific target DNA sequence. A gRNA comprises a DNA-targeting segment and protein-binding segment. The DNA-targeting segment of a gRNA comprises a nucleotide sequence that is complementary to a sequence in the target DNA sequence. As such, the DNA-targeting segment of a gRNA interacts with a target DNA in a sequence-specific manner via hybridization (i.e., base pairing), and the nucleotide sequence of the DNA-targeting segment determines the location within the target DNA that the gRNA will bind. The DNA-targeting segment of a gRNA can be modified (e.g., by genetic engineering) to hybridize to any desired sequence within a target DNA sequence.

The protein-binding segment of a guide RNA interacts with a site-directed modifying polypeptide (e.g. a Cas9 protein) to form a complex. The guide RNA guides the bound polypeptide to a specific nucleotide sequence within target DNA via the above-described DNA-targeting segment. The protein-binding segment of a guide RNA comprises two stretches of nucleotides that are complementary to one another and which form a double stranded RNA duplex.

In some embodiments, a gRNA comprises two separate RNA molecules. In such embodiments, each of the two RNA molecules comprises a stretch of nucleotides that are complementary to one another such that the complementary nucleotides of the two RNA molecules hybridize to form the double-stranded RNA duplex of the protein-binding segment. In some embodiments, a gRNA comprises a single RNA molecule (sgRNA).

The specificity of a gRNA for a target loci is mediated by the sequence of the DNA-binding segment, which comprises about 20 nucleotides that are complementary to a target DNA sequence within the target locus. In some embodiments, the corresponding target DNA sequence is approximately 20 nucleotides in length. In some embodiments, the DNA-binding segments of the gRNA sequences of the present invention are at least 90% complementary to a target DNA sequence within a target locus. In some embodiments, the DNA-binding segments of the gRNA sequences of the present invention are at least 95%, 96%, 97%, 98%, or 99% complementary to a target DNA sequence within a target locus. In some embodiments, the DNA-binding segments of the gRNA sequences of the present invention are 100% complementary to a target DNA sequence within a target locus.

In some embodiments, the DNA-binding segments of the gRNA sequences bind to a target DNA sequence that is at least 90% identical to a target DNA sequence within a target locus of the BTK gene. In some embodiments, the DNA-binding segments of the gRNA sequences bind to a target DNA sequence that is at least 95%, 96%, 97%, 98%, or 99% identical to a target DNA sequence within a target locus of a target gene selected those listed in Table 1. In some embodiments, the DNA-binding segments of the gRNA sequences bind to a target DNA sequence that is 100% identical to a target DNA sequence within a target locus of a target gene selected those listed in Table 1. In some embodiments, the DNA-binding segments of the gRNA sequences bind to a target DNA sequence that is at least 90% identical to a target DNA sequence within a target locus within an exon or within an intron of the BTK gene, preferably within the second or third exon of the BTK gene. In some embodiments, the DNA-binding segments of the gRNA sequences bind to a target DNA sequence that is at least 95%, 96%, 97%, 98%, or 99% identical to a target DNA sequence within a target locus within an exon or within an intron of the BTK gene, preferably within the second or third exon of the BTK gene. In some embodiments, t the DNA-binding segments of the gRNA sequences bind to a target DNA sequence that is 100% identical to a target DNA sequence within a target locus within an exon or within an intron of the BTK gene, preferably within the second or third exon of the BTK gene.

In some embodiments, the DNA-binding segments of the gRNA sequences bind to a target DNA sequence that is at least 90% identical to one of the sequences in Table 3.

TABLE 3

| Exemplary Guide Sequences | |
|---|---|
| Guide | Sequence |
| G1 | AGCTATGGCCGCAGTGATTC (SEQ ID NO: 9) |
| G2 | AGGCGCTTCTTGAAGTTTAG (SEQ ID NO: 10) |
| G3 | ATGAGTATGACTTTGAACGT (SEQ ID NO: 11) |
| G4 | AGGGATGAGGATTAATGTCC (SEQ ID NO: 12) |
| G5 | ACACTGAATTGGGGGGGGAT (SEQ ID NO: 13) |
| G6 | AACTAGGTAGCTAGGCTGAG (SEQ ID NO: 14) |
| G7 | GCTTTAGCTAGTTATAGGCT (SEQ ID NO: 15) |
| G8 | AGAGGTAAATTTTCGTTGGT (SEQ ID NO: 16) |
| G9 | GATGCACACTGAATTGGGGG (SEQ ID NO: 17) |

In some embodiments, the DNA-binding segments of the gRNA sequences bind to a target DNA sequence that is at least 95%, 96%, 97%, 98%, or 99% identical to one of the sequences in Table 3. In some embodiments, the DNA-binding segments of the gRNA sequences bind to a target DNA sequence that is 100% identical to one of the sequences in Table 3.

In some embodiments, the gene editing composition comprises two or more gRNA molecules each comprising a DNA-binding segment, wherein at least one of the DNA-binding segments bind to a target DNA sequence that is at least 90% identical to a target DNA sequence within a target locus of the BTK gene. In some embodiments, the gene editing composition comprises two or more gRNA molecules each comprising a DNA-binding segment, wherein at least one of the DNA-binding segments bind to a target DNA sequence that is at least 95%, 96%, 97%, 98%, or 99% identical to a target DNA sequence within a target locus of a target gene selected those listed in Table 1. In some embodiments, the gene editing composition comprises two or more gRNA molecules each comprising a DNA-binding segment, wherein at least one of the DNA-binding segments bind to a target DNA sequence that is 100% identical to a target DNA sequence within a target locus of a target gene selected those listed in Table 1. In some embodiments, the gene editing composition comprises two or more gRNA molecules each comprising a DNA-binding segment, wherein at least one of the DNA-binding segments bind bind to a target DNA sequence that is at least 90% identical to a target DNA sequence within a target locus within an exon or within an intron of the BTK gene, preferably within the second or third exon of the BTK gene. In some embodiments, the gene editing composition comprises two or more gRNA molecules each comprising a DNA-binding segment, wherein at least one of the DNA-binding segments bind to a target DNA sequence that is at least 95%, 96%, 97%, 98%, or 99% identical to a target DNA sequence within a target locus within an exon or within an intron of the BTK gene, preferably within the second or third exon of the BTK gene. In some embodiments, the gene editing composition comprises two or more gRNA molecules each comprising a DNA-binding segment, wherein at least one of the DNA-binding segments bind to a target DNA sequence that is 100% identical to a target DNA sequence within a target locus within an exon or within an intron of the BTK gene, preferably within the second or third exon of the BTK gene.

In some embodiments, the gene editing composition comprises two or more gRNA molecules each comprising a DNA-binding segment, wherein at least one of the DNA-binding segments bind to a target DNA sequence that is at least 90% identical to one of SEQ ID NOS: 1-8. In some embodiments, the gene editing composition comprises two or more gRNA molecules each comprising a DNA-binding segment, wherein at least one of the DNA-binding segments bind to a target DNA sequence that is at least 95%, 96%, 97%, 98%, or 99% identical to one of SEQ ID NOS: 1-8. In some embodiments, the gene editing composition comprises two or more gRNA molecules each comprising a DNA-binding segment, wherein at least one of the DNA-binding segments bind to a target DNA sequence that is 100% identical to one of SEQ ID NOS: 1-8.

In some embodiments, the DNA-binding segments of the gRNA sequences described herein are designed to minimize off-target binding using algorithms known in the art (e.g., Cas-OFF finder) to identify target sequences that are unique to a particular target locus or target gene.

In some embodiments, the gRNAs described herein can comprise one or more modified nucleosides or nucleotides which introduce stability toward nucleases. In such embodiments, these modified gRNAs may elicit a reduced innate immune as compared to a non-modified gRNA. The term "innate immune response" includes a cellular response to exogenous nucleic acids, including single stranded nucleic acids, generally of viral or bacterial origin, which involves the induction of cytokine expression and release, particularly the interferons, and cell death.

In some embodiments, the gRNAs described herein are modified at or near the 5' end (e.g., within 1-10, 1-5, or 1-2 nucleotides of their 5' end). In some embodiments, the 5' end of a gRNA is modified by the inclusion of a eukaryotic mRNA cap structure or cap analog (e.g., a G(5 ')ppp(5')G cap analog, a m7G(5 ')ppp(5')G cap analog, or a 3 '-0-Me-m7G(5')ppp(5 ')G anti reverse cap analog (ARCA)). In some embodiments, an in vitro transcribed gRNA is modified by treatment with a phosphatase (e.g., calf intestinal alkaline phosphatase) to remove the 5' triphosphate group. In some embodiments, a gRNA comprises a modification at or near its 3' end (e.g., within 1-10, 1-5, or 1-2 nucleotides of its 3' end). For example, in some embodiments, the 3' end of a gRNA is modified by the addition of one or more (e.g., 25-200) adenine (A) residues.

In some embodiments, modified nucleosides and modified nucleotides can be present in a gRNA, but also may be present in other gene-regulating systems, e.g., mRNA, RNAi, or siRNA-based systems. In some embodiments, modified nucleosides and nucleotides can include one or more of:

a) alteration, e.g., replacement, of one or both of the non-linking phosphate oxygens and/or of one or more of the linking phosphate oxygens in the phosphodiester backbone linkage;
b) alteration, e.g., replacement, of a constituent of the ribose sugar, e.g., of the 2' hydroxyl on the ribose sugar;
c) wholesale replacement of the phosphate moiety with "dephospho" linkers;
d) modification or replacement of a naturally occurring nucleobase;
e) replacement or modification of the ribose-phosphate backbone;
f) modification of the 3' end or 5' end of the oligonucleotide, e.g., removal, modification or replacement of a terminal phosphate group or conjugation of a moiety; and
g) modification of the sugar.

In some embodiments, the modifications listed above can be combined to provide modified nucleosides and nucleotides that can have two, three, four, or more modifications. For example, in some embodiments, a modified nucleoside or nucleotide can have a modified sugar and a modified nucleobase. In some embodiments, every base of a gRNA is modified. In some embodiments, each of the phosphate groups of a gRNA molecule are replaced with phosphorothioate groups.

In some embodiments, a software tool can be used to optimize the choice of gRNA within a user's target sequence, e.g., to minimize total off-target activity across the genome. Off target activity may be other than cleavage. For example, for each possible gRNA choice using *S. pyogenes* Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool.

End-Processing Enzymes

Genome editing compositions and methods contemplated in particular embodiments comprise editing cellular genomes using a TALEN variant or Cas protein and an end-processing enzyme. In particular embodiments, a single polynucleotide encodes a TALEN or Cas protein and an end-processing enzyme, separated by a linker, a self-cleaving peptide sequence, e.g., 2A sequence, or by an IRES sequence. In particular embodiments, genome editing compositions comprise a polynucleotide encoding a TALEN variant or Cas protein and a separate polynucleotide encoding an end-processing enzyme.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a TALEN or a CRISPR/Cas system and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a TALEN or Cas protein and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' or 5' exonuclease, preferably Trex 1 or Trex2, more preferably Trex2, and even more preferably human or mouse Trex2.

E. Target Sites

Nuclease variants contemplated in particular embodiments can be designed to bind to any suitable target sequence in a BTK gene and can have a novel binding specificity, compared to a naturally-occurring effector domain. In particular embodiments, the target site is a regulatory region of a gene including, but not limited to promoters, enhancers, repressor elements, and the like. In particular embodiments, the target site is a coding region of a gene or a splice site. In particular embodiments, a TALEN variant or CRISPR/Cas system and donor repair template can be designed to insert a therapeutic polynucleotide. In particular embodiments, a TALEN variant or CRISPR/Cas system and donor repair template can be designed to insert a therapeutic polynucleotide under control of the endogenous BTK gene regulatory elements or expression control sequences.

In various embodiments, TALEN variants or CRISPR/Cas systems bind to and cleave a target sequence in the Bruton's tyrosine kinase (BTK) gene, which is located on the X chromosome. The BTK gene encodes a tyrosine kinase, which is essential for the development and maturation of B cells. BTK is also referred to as Bruton Agammaglobulinemia Tyrosine Kinase, B-Cell Progenitor Kinase (BPK), Tyrosine-Protein Kinase BTK Isoform (Lacking Exon 13 To 17), Dominant-Negative Kinase-Deficient Brutons Tyrosine Kinase, Tyrosine-Protein Kinase BTK Isoform (Lacking Exon 14), Truncated Bruton Agammaglobulinemia Tyrosine Kinase, PSCTK1, AGMX1, Agammaglobulinaemia Tyrosine Kinase (ATK), Agammaglobulinemia Tyrosine Kinase, Tyrosine-Protein Kinase BTK, and IMD1, among others. Exemplary BTK reference sequences numbers used in particular embodiments include, but are not limited to NM_000061.2, NP_000052.1, AK057105, BC109079, DA619542, DB636737, CCDS14482.1, Q06187, Q5JY90, ENSP00000308176.7, OTTHUMP00000023676, ENST00000308731.7, OTTHUMT00000057532, NM_001287344.1, NP_001274273.1, NM_001287345.1, and NP_001274274.1.

In particular embodiments, a TALEN variant or CRISPR/Cas system introduces a double-strand break (DSB) in a BTK gene, preferably a target sequence in the first or second intron of the human BTK gene, and more preferably a target sequence in the first or second intron of the human BTK gene as set forth in SEQ ID NOS: 1-8. In particular embodiments, the TALEN or CRISPR/Cas system comprises a nuclease that introduces a double strand break at the target site in the first or second intron of the BTK gene as set forth in SEQ ID NOS: 1-8 by cleaving the sequence "ACTT."

In a preferred embodiment, a TALEN or CRISPR/Cas system cleaves double-stranded DNA and introduces a DSB into the polynucleotide sequence set forth in SEQ ID NOS: 1-8.

In a preferred embodiment, the BTK gene is a human BTK gene.

F. Donor Repair Templates

Nuclease variants may be used to introduce a DSB in a target sequence; the DSB may be repaired through homology directed repair (HDR) mechanisms in the presence of one or more donor repair templates. In particular embodiments, the donor repair template is used to insert a sequence into the genome. In particular preferred embodiments, the donor repair template is used to insert a polynucleotide sequence encoding a therapeutic BTK polypeptide, e.g., SEQ ID NO: 18.

(SEQ ID NO: 18)

```
MAAVILESIFLKRSQQKKKTSPLNFKKRLFLLTVHKLSYYEYDFERGRR
GSKKGSIDVEKITCVETVVPEKNPPPERQIPRRGEESSEMEQISIIERF
PYPFQVVYDEGPLYVESPTEELRKRWIHQLKNVIRYNSDLVQKYHPCFW
IDGQYLCCSQTAKNAMGCQILENRNGSLKPGSSHRKTKKPLPPTPEEDQ
ILKKPLPPEPAAAPVSTSELKKVVALYDYMPMNANDLQLRKGDEYFILE
ESNLPWWRARDKNGQEGYIPSNYVTEAEDSIEMYEWYSKHMTRSQAEQL
LKQEGKEGGFIVRDSSKAGKYTVSVFAKSTGDPQGVIRHYVVCSTPQSQ
YYLAEKHLFSTIPELINYHQHNSAGLISRLKYPVSQQNKNAPSTAGLGY
GSWEIDPKDLTFLKELGTGQFGVVKYGKWRGQYDVAIKMIKEGSMSEDE
FIEEAKVMMNLSHEKLVQLYGVCTKQRPIFIITEYMANGCLLNYLREMR
HRFQTQQLLEMCKDVCEAMEYLESKQFLHRDLAARNCLVNDQGVVKVSD
EGLSRYVLDDEYTSSVGSKFPVRWSPPEVLMYSKESSKSDIWAFGVLMW
EIYSLGKMPYERFTNSETAEHIAQGLRLYRPHLASEKVYTIMYSCWHEK
ADERPTFKILLSNILDVMDEES
```

In particular preferred embodiments, the donor repair template is used to insert a polynucleotide sequence encoding a therapeutic BTK polypeptide, such that the expression of the BTK polypeptide is under control of the endogenous BTK promoter and/or enhancers.

In various embodiments, a donor repair template is introduced into a hematopoietic cell, e.g., a hematopoietic stem or progenitor cell, or $CD34^+$ cell, by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, the donor repair template comprises one or more homology arms that flank the DSB site.

As used herein, the term "homology arms" refers to a nucleic acid sequence in a donor repair template that is identical, or nearly identical, to DNA sequence flanking the DNA break introduced by the nuclease at a target site. In one embodiment, the donor repair template comprises a 5' homology arm that comprises a nucleic acid sequence that is identical or nearly identical to the DNA sequence 5' of the DNA break site. In one embodiment, the donor repair template comprises a 3' homology arm that comprises a nucleic acid sequence that is identical or nearly identical to the DNA sequence 3' of the DNA break site. In a preferred embodiment, the donor repair template comprises a 5' homology arm and a 3' homology arm. The donor repair template may comprise homology to the genome sequence immediately adjacent to the DSB site, or homology to the genomic sequence within any number of base pairs from the DSB site. In one embodiment, the donor repair template comprises a nucleic acid sequence that is homologous to a genomic sequence about 5 bp, about 10 bp, about 25 bp, about 50 bp, about 100 bp, about 250 bp, about 500 bp, about 1000 bp, about 2500 bp, about 5000 bp, about 10000 bp or more, including any intervening length of homologous sequence.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of the 5' and 3' homology arms are independently selected from about 500 bp to about 1500 bp. In one embodiment, the 5'homology arm is about 1500 bp and the 3' homology arm is about 1000 bp. In one embodiment, the 5'homology arm is between about 200 bp to about 600 bp and the 3' homology arm is between about 200 bp to about 600 bp. In one embodiment, the 5'homology arm is about 200 bp and the 3' homology arm is about 200 bp. In one embodiment, the 5'homology arm is about 300 bp and the 3' homology arm is about 300 bp. In one embodiment, the 5'homology arm is about 400 bp and the 3' homology arm is about 400 bp. In one embodiment, the 5'homology arm is about 500 bp and the 3' homology arm is about 500 bp. In one embodiment, the 5'homology arm is about 600 bp and the 3' homology arm is about 600 bp.

G. Polypeptides

Various polypeptides are contemplated herein, including, but not limited to, TALENs and Cas proteins. In preferred embodiments, a polypeptide comprises the amino acid sequence encoding one or more of the RVDs set forth in Table 2. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Illustrative examples of polypeptides contemplated in particular embodiments include, but are not limited to TALENs, Cas proteins, end-processing nucleases, fusion polypeptides and variants thereof.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a TALEN, CRISPR/Cas or the like that binds and cleaves a target site in the human BTK gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a TALEN variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a TALEN or TAL effector domain compared to a corresponding wild type TALEN or TAL effector domain sequence, more preferably a deletion of the 4 N-terminal amino acids of a TALEN or TAL effector domain compared to a corresponding wild type TALEN or TAL effector domain sequence. In a particular embodiment, a biologically active fragment lacks or comprises a deletion of the 1, 2, 3, 4, or 5 C-terminal amino acids of a TALEN or TAL effector domain compared to a corresponding wild type TALEN or TAL effector domain, more preferably a deletion of the 2 C-terminal amino acids of a TALEN or TAL effector domain compared to a corresponding wild type TALEN or TAL effector domain. In a particular preferred embodiment, a biologically active fragment lacks or comprises a deletion of the 4 N-terminal amino acids and 2 C-terminal amino acids of a TALEN or TAL effector domain compared to a corresponding wild type TALEN or TAL effector domain.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82:488-492), Kunkel et al., (1987, *Methods in Enzymol,* 154:367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (*Natl. Biomed. Res. Found.*, Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | GCU | | |
| Cysteine | C | Cys | UGC | UGU | | | | |
| Aspartic acid | D | Asp | GAC | GAU | | | | |
| Glutamic acid | E | Glu | GAA | GAG | | | | |
| Phenylalanine | F | Phe | UUC | UUU | | | | |
| Glycine | G | Gly | GGA | GGC | GGG | GGU | | |
| Histidine | H | His | CAC | CAU | | | | |
| Isoleucine | I | Iso | AUA | AUC | AUU | | | |
| Lysine | K | Lys | AAA | AAG | | | | |
| Leucine | L | Leu | UUA | UUG | CUA | CUC | CUG | CUU |
| Methionine | M | Met | AUG | | | | | |
| Asparagine | N | Asn | AAC | AAU | | | | |
| Proline | P | Pro | CCA | CCC | CCG | CCU | | |
| Glutamine | Q | Gln | CAA | CAG | | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | | |
| Valine | V | Val | GUA | GUC | GUG | GUU | | |
| Tryptophan | W | Trp | UGG | | | | | |
| Tyrosine | Y | Tyr | UAC | UAU | | | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more TAL effector domain and one or more nucleases, and one or more linker and/or self-cleaving polypeptides.

In one embodiment, a fusion protein contemplated herein comprises a TALEN variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers (G) n; glycine-serine polymers $(G_{1-5}S_{1-5})_n$, where n is an integer of at least one, two, three, four, or five; glycine-alanine polymers; alanine-serine polymers; GGG; DGGGS (SEQ ID NO: 36); TGEKP (SEQ ID NO: 37) (see e.g., Liu et al., *PNAS* 5525-5530 (1997)); GGRR (SEQ ID NO: 38) (Pomerantz et al. 1995, supra); $(GGGGS)_n$ wherein n=1, 2, 3, 4 or 5 (SEQ ID NO: 39) (Kim et al., *PNAS* 93, 1156-1160 (1996.); EGKSSGSGSESKVD (SEQ ID NO: 40) (Chaudhary et al., 1990, *Proc. Natl. Acad. Sci. U.S.A.* 87:1066-1070); KESGSVSSEQLAQFRSLD (SEQ ID NO 41) (Bird et al., 1988, *Science* 242:423-426), GGRRGGGS (SEQ ID NO: 42); LRQRDGERP (SEQ ID NO: 43); LRQKDGGGSERP (SEQ ID NO:44); LRQKD (GGGS) 2ERP (SEQ ID NO: 45). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5 (8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ (G/S) (SEQ ID NO: 46), for example, ENLYFQG (SEQ ID NO: 47) and ENLYFQS (SEQ ID NO: 48), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

| Exemplary 2A sites include the following sequences: | |
|---|---|
| SEQ ID NO: 49 | GSGATNFSLLKQAGDVEENPGP |
| SEQ ID NO: 50 | ATNFSLLKQAGDVEENPGP |
| SEQ ID NO: 51 | LLKQAGDVEENPGP |
| SEQ ID NO: 52 | GSGEGRGSLLTCGDVEENPGP |
| SEQ ID NO: 53 | EGRGSLLTCGDVEENPGP |
| SEQ ID NO: 54 | LLTCGDVEENPGP |
| SEQ ID NO: 55 | GSGQCTNYALLKLAGDVESNPGP |
| SEQ ID NO: 56 | QCTNYALLKLAGDVESNPGP |
| SEQ ID NO: 57 | LLKLAGDVESNPGP |
| SEQ ID NO: 58 | GSGVKQTLNFDLLKLAGDVESNPGP |
| SEQ ID NO: 59 | VKQTLNFDLLKLAGDVESNPGP |
| SEQ ID NO: 60 | LLKLAGDVESNPGP |
| SEQ ID NO: 61 | LLNFDLLKLAGDVESNPGP |
| SEQ ID NO: 62 | TLNFDLLKLAGDVESNPGP |
| SEQ ID NO: 63 | LLKLAGDVESNPGP |
| SEQ ID NO: 64 | NFDLLKLAGDVESNPGP |
| SEQ ID NO: 65 | QLLNFDLLKLAGDVESNPGP |

TABLE 2-continued

| Exemplary 2A sites include the following sequences: | |
|---|---|
| SEQ ID NO: 66 | APVKQTLNFDLLKLAGDVESNPGP |
| SEQ ID NO: 67 | VTELLYRMKRAETYCPRPLLAIHPTEA RHKQKIVAPVKQT |
| SEQ ID NO: 68 | LNFDLLKLAGDVESNPGP |
| SEQ ID NO: 69 | LLAIHPTEARHKQKIVAPVKQTLNFDL LKLAGDVESNPGP |
| SEQ ID NO: 70 | EARHKQKIVAPVKQTLNFDLLKLAGDV ESNPGP |

H. Polynucleotides

In particular embodiments, polynucleotides encoding one or more TALENs, TAL effector domains, Cas proteins, guide RNAs (gRNA), end-processing enzymes, and fusion polypeptides contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), synthetic RNA, synthetic mRNA, genomic DNA (gDNA), PCR amplified DNA, complementary DNA (cDNA), synthetic DNA, and recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994*, Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

In various illustrative embodiments, polynucleotides contemplated herein include, but are not limited to polynucleotides encoding TALEN, CRISPR/Cas systems, guide RNAs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

In various embodiments, a polynucleotide comprises an mRNA encoding a polypeptide contemplated herein including, but not limited to, a TALEN, TAL effector domain, Cas protein, and an end-processing enzyme. In certain embodiments, the mRNA comprises a cap, one or more nucleotides and/or modified nucleotides, and a poly(A) tail.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' AGTCATG3' is 3'TCAGTAC5'. The latter sequence is often written as the reverse complement with the 5' end on the left and the 3' end on the right, 5' CATGA CT 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, Piggy Bac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector-origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately to 30 bases upstream from the site where transcription is initiated and/or another 25 sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc.

Conditional expression can also be achieved by using a site specific DNA recombinase. According to certain embodiments, polynucleotides comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, @C31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. RNA 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3):1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC) RCCATGG (SEQ ID NO: 71), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences can promote mRNA stability by addition of a poly A tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal poly A sequence (e.g., AATAAA, ATTAAA, AGTAAA). In particular embodiments, the poly(A) sisequence is an SV40 poly A sequence, a bovine growth hormone polyA sequence (BGHpA), a rabbit β-globin polyA sequence (rßgpA), variants thereof, or another suitable heterologous or endogenous poly A sequence known in the art.

In particular embodiments, polynucleotides encoding one or more TALENS, CRISPR/Cas systems, end-processing enzymes, or fusion polypeptides may be introduced into hematopoietic cells, e.g., $CD34^+$ cells, by both non-viral and viral methods. In particular embodiments, delivery of one or more polynucleotides encoding TALEN or Cas nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a $CD34^+$ cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid: nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising TALEN variants or CRISPR/Cas systems and/or donor repair templates are administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include, but are not limited to adeno-associated virus (AAV), retrovirus, herpes simplex virus, adenovirus, and vaccinia virus vectors.

I. Genome Edited Cells

The genome edited cells manufactured by the methods contemplated in particular embodiments provide improved cell-based therapeutics for the treatment of X-linked agammaglobulinemia (XLA). Without wishing to be bound to any particular theory, it is believed that the compositions and methods contemplated herein can be used to introduce a polynucleotide encoding a functional BTK polypeptide into a BTK gene that comprises one or more mutations and/or deletions that result in little or no endogenous BTK expression and XLA; and thus, provide a more robust genome edited cell composition that may be used to treat, and in some embodiments potentially cure, XLA.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

Illustrative examples of cell types whose genome can be edited using the compositions and methods contemplated herein include, but are not limited to, cell lines, primary cells, stem cells, progenitor cells, and differentiated cells.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

In particular embodiments, the cell is a primary cell. The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, Methods Mol Biol. 1997). Primary cells for use in the methods contemplated herein are derived from umbilical cord blood, placental blood, mobilized peripheral blood and bone marrow. In one embodiment, the primary cell is a hematopoietic stem or progenitor cell.

In one embodiment, the genome edited cell is an embryonic stem cell.

In one embodiment, the genome edited cell is an adult stem or progenitor cell.

In one embodiment, the genome edited cell is primary cell.

In a preferred embodiment, the genome edited cell is a hematopoietic cell, e.g., hematopoietic stem cell, hematopoietic progenitor cell, such as a B cell progenitor cell, or cell population comprising hematopoietic cells.

As used herein, the term "population of cells" refers to a plurality of cells that may be made up of any number and/or combination of homogenous or heterogeneous cell types, as described elsewhere herein. For example, for transduction of hematopoietic stem or progenitor cells, a population of cells may be isolated or obtained from umbilical cord blood, placental blood, bone marrow, or mobilized peripheral blood. A population of cells may comprise about 10%, about 20%, about 30%, about 40%, about 50%, about 60%, about 70%, about 80%, about 90%, or about 100% of the target cell type to be edited. In certain embodiments, hematopoietic stem or progenitor cells may be isolated or purified from a population of heterogeneous cells using methods known in the art.

Illustrative sources to obtain hematopoietic cells include, but are not limited to: cord blood, bone marrow or mobilized peripheral blood.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Additional illustrative examples of hematopoietic stem or progenitor cells suitable for use with the methods and compositions contemplated herein include hematopoietic cells that are $CD34^{+}CD38^{Lo}CD90^{+}CD45^{RA-}$, hematopoietic cells that are $CD34^{+}$, $CD59^{+}$, Thy $1/CD90^{+}$, $CD38^{Lo/-}$, C-kit/$CD117^{+}$, and $Lin^{(-)}$, and hematopoietic cells that are $CD133^{+}$.

In a preferred embodiment, the hematopoietic cells that are $CD133^{+}CD90^{+}$.

In a preferred embodiment, the hematopoietic cells that are $CD133^{+}CD34^{+}$.

In a preferred embodiment, the hematopoietic cells that are $CD133^{+}CD90^{+}CD34^{+}$.

Various methods exist to characterize hematopoietic hierarchy. One method of characterization is the SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD150, CD244, etc., CD150 being the founding member, and, thus, also called slamF1, i.e., SLAM family member 1. The signature SLAM code for the hematopoietic hierarchy is hematopoietic stem cells (HSC)-$CD150^{+}CD48^{-}CD244^{-}$; multipotent progenitor cells (MPPs)-$CD150^{-}CD48^{-}CD244^{+}$; lineage-restricted progenitor cells (LRPs)-$CD150^{-}CD48^{+}CD244^{+}$; common myeloid progenitor (CMP)-lin-SCA-1-c-$kit^{+}$ $CD34^{+}CD16/32^{mid}$; granulocyte-macrophage progenitor (GMP)-$lin^{-}$SCA-1-c-$kit^{+}CD34^{+}CD16/32^{hi}$; and megakaryocyte-erythroid progenitor (MEP)-$lin^{-}$SCA-1-c-$kit^{+}CD34^{-}$ $CD16/32^{low}$.

Preferred target cell types edited with the compositions and methods contemplated herein include, hematopoietic cells, preferably human hematopoietic cells, more preferably human hematopoietic stem and progenitor cells, and even more preferably $CD34^{+}$ human hematopoietic stem cells. The term "CD34+ cell," as used herein refers to a cell expressing the CD34 protein on its cell surface. "CD34," as used herein refers to a cell surface glycoprotein (e.g., sialomucin protein) that often acts as a cell-cell adhesion factor. CD34+ is a cell surface marker of both hematopoietic stem and progenitor cells.

In one embodiment, the genome edited hematopoietic cells are $CD150^{+}CD48^{-}CD244^{-}$cells.

In one embodiment, the genome edited hematopoietic cells are $CD34^{+}CD133^{+}$ cells.

In one embodiment, the genome edited hematopoietic cells are $CD133^{+}$ cells.

In one embodiment, the genome edited hematopoietic cells are $CD34^{+}$ cells.

In particular embodiments, a population of hematopoietic cells comprising hematopoietic stem and progenitor cells (HSPCs) comprises a defective BTK gene edited to express a functional BTK polypeptide, wherein the edit is a DSB repaired by HDR.

In particular embodiments, the genome edited cells comprise B cell progenitor cells.

In particular embodiments, the genome edited cells comprise one or more mutations and/or deletions in a BTK gene that result in little or no endogenous BTK expression.

J. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in the human BTK gene in a cell or a population of cells. In preferred embodiments, a genome editing composition is used to edit a BTK gene by HDR in a hematopoietic cell, e.g., a hematopoietic stem or progenitor cell, or a $CD34^{+}$ cell.

In various embodiments, the compositions contemplated herein comprise a TALEN variant or CRISPR/Cas system, and optionally an end-processing enzyme, e.g., a 3'-5' exonuclease (Trex2). The TALEN variant or Cas protein may be in the form of an mRNA that is introduced into a cell via polynucleotide delivery methods disclosed supra, e.g., electroporation, lipid nanoparticles, etc. In one embodiment, a composition comprising an mRNA encoding a TALEN or a Cas protein, along with a guide RNA if a Cas protein is used, and optionally a 3'-5' exonuclease, is introduced in a cell via polynucleotide delivery methods disclosed supra.

In particular embodiments, the compositions contemplated herein comprise a population of cells, a TALEN variant or CRISPR/Cas system, and optionally, a donor repair template. In particular embodiments, the compositions contemplated herein comprise a population of cells, a TALEN variant or CRISPR/Cas system, an end-processing enzyme, and optionally, a donor repair template. The TALEN variant, or CRISPR/Cas system, and/or end-processing enzyme may be in the form of an mRNA that is introduced into the cell via polynucleotide delivery methods disclosed supra. The donor repair template may also be introduced into the cell by means of a separate composition.

In particular embodiments, the compositions contemplated herein comprise a population of cells, a TALEN or CRISPR/Cas and gRNA, and optionally, a donor repair template. In particular embodiments, the compositions contemplated herein comprise a population of cells, a TALEN or CRISPR/Cas and gRNA, a 3'-5' exonuclease, and optionally, a donor repair template. The TALEN, or CRISPR/Cas and gRNA, and/or 3'-5' exonuclease may be in the form of an mRNA that is introduced into the cell via polynucleotide delivery methods disclosed supra. The donor repair template may also be introduced into the cell by means of a separate composition. The gRNA and Cas protein may also be introduced into the cell together or by means of separate compositions. The Cas protein can be supplied as a protein or as a polynucleotide encoding the protein.

In particular embodiments, the population of cells comprise genetically modified hematopoietic cells including, but not limited to, hematopoietic stem cells, hematopoietic progenitor cells, $CD133^{+}$ cells, and $CD34^{+}$ cells.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified hematopoietic stem and/or progenitor cells comprising an exogenous polynucleotide encoding a functional BTK polypeptide and a pharmaceutically acceptable carrier.

In particular embodiments, compositions contemplated herein comprise genetically modified hematopoietic stem and/or progenitor cells comprising a BTK gene comprising one or more mutations and/or deletions and an exogenous polynucleotide encoding a functional BTK polypeptide and a pharmaceutically acceptable carrier. A composition comprising a cell-based composition contemplated herein can be administered by parenteral administration methods.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a nontoxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited hematopoietic stem and/or progenitor cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited cells, e.g., hematopoietic stem and progenitor cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions include, but are not limited to QBSF-60 (Quality Biological, Inc.), StemPro-34 (Life Technologies), and X-VIVO 10.

In a preferred embodiment, the compositions comprising genome edited hematopoietic stem and/or progenitor cells are formulated in PlasmaLyte.

In various embodiments, compositions comprising hematopoietic stem and/or progenitor cells are formulated in a cryopreservation medium. For example, cryopreservation media with cryopreservation agents may be used to maintain a high cell viability outcome post-thaw. Illustrative examples of cryopreservation media used in particular compositions include, but are not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contains about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more TALEN variants or CRISPR/Cas systems, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intraarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, PA: Pharmaceutical Press; 2012, which is incorporated by reference herein, in its entirety.

K. Genome Edited Cell Therapies

The genome edited cells manufactured by the methods contemplated in particular embodiments provide improved drug products for use in the prevention, treatment, and amelioration of X-linked agammaglobulinemia (XLA) or for preventing, treating, or ameliorating at least one symptom associated with XLA or a subject having an XLA causing mutation in a BTK gene. As used herein, the term "drug product" refers to genetically modified cells produced using the compositions and methods contemplated herein. In particular embodiments, the drug product comprises genetically modified hematopoietic stem or progenitor cells, e.g., CD34$^+$ cells. The genetically modified hematopoietic stem or progenitor cells give rise to the entire B cell lineage, whereas non-modified cells comprising one or more mutations and/or deletions in a BTK gene that lead to XLA are defective in B cell development.

In particular embodiments, hematopoietic stem or progenitor cells that will be edited comprise a non-functional or disrupted, ablated, or partially deleted BTK gene, thereby reducing or eliminating BTK expression and abrogating normal B cell development.

In particular embodiments, genome edited hematopoietic stem or progenitor cells comprise a non-functional or disrupted, ablated, or partially deleted BTK gene, thereby reducing or eliminating endogenous BTK expression and further comprise a polynucleotide, inserted into the BTK gene, encoding a functional BTK polypeptide that restores normal B cell development.

In particular embodiments, genome edited hematopoietic stem or progenitor cells provide a curative, preventative, or ameliorative therapy to a subject diagnosed with or that is suspected of having XLA.

In various embodiments, the genome editing compositions are administered by direct injection to a cell, tissue, or organ of a subject in need of gene therapy, in vivo, e.g., bone marrow. In various other embodiments, cells are edited in vitro or ex vivo with TALEN variants or CRISPR/Cas systems contemplated herein, and optionally expanded ex vivo. The genome edited cells are then administered to a subject in need of therapy.

Preferred cells for use in the genome editing methods contemplated herein include autologous/autogeneic ("self") cells, preferably hematopoietic cells, more preferably hematopoietic stem or progenitor cell, and even more preferably CD34$^+$ cells.

As used herein, the terms "individual" and "subject" are often used interchangeably and refer to any animal that exhibits a symptom of XLA that can be treated with the TALEN or CRISPR/Cas, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having XLA.

As used herein, the term "patient" refers to a subject that has been diagnosed with XLA that can be treated with the TALEN or CRISPR/Cas, genome editing compositions, gene therapy vectors, genome editing vectors, genome edited cells, and methods contemplated elsewhere herein.

As used herein "treatment" or "treating," includes any beneficial or desirable effect on the symptoms or pathology of XLA, and may include even minimal reductions in one or more measurable markers of XLA. Treatment can optionally involve delaying of the progression of XLA. "Treatment" does not necessarily indicate complete eradication or cure of XLA, or associated symptoms thereof.

As used herein, "prevent," and similar words such as "prevention," "prevented," "preventing" etc., indicate an approach for preventing, inhibiting, or reducing the likelihood of the occurrence or recurrence of, XLA. It also refers to delaying the onset or recurrence of XLA or delaying the occurrence or recurrence of XLA. As used herein, "prevention" and similar words also includes reducing the intensity, effect, symptoms and/or burden of XLA prior to its onset or recurrence.

As used herein, the phrase "ameliorating at least one symptom of" refers to decreasing one or more symptoms of XLA. In particular embodiments, one or more symptoms of XLA that are ameliorated include, but are not limited to, common infections including but not limited to bronchitis (airway infection), chronic diarrhea, conjunctivitis (eye infection), otitis media (middle ear infection), pneumonia (lung infection), sinusitis (sinus infection), skin infections, upper respiratory tract infections; infections due to bacteria, viruses, and other microbes; and bacterial infections including, but not limited to, *Haemophilus influenzae*, pneumococci (*Streptococcus pneumoniae*), and staphylococci infections.

As used herein, the term "amount" refers to "an amount effective" or "an effective amount" of a TALEN variant or CRISPR/Cas system, genome editing composition, or genome edited cell sufficient to achieve a beneficial or desired prophylactic or therapeutic result, including clinical results.

A "prophylactically effective amount" refers to an amount of a TALEN variant or CRISPR/Cas system, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a TALEN variant or CRISPR/Cas system, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

The genome edited cells may be administered as part of a bone marrow or cord blood transplant in an individual that has or has not undergone bone marrow ablative therapy. In one embodiment, genome edited cells contemplated herein are administered in a bone marrow transplant to an individual that has undergone chemoablative or radioablative bone marrow therapy.

In one embodiment, a dose of genome edited cells is delivered to a subject intravenously. In preferred embodiments, genome edited hematopoietic stem cells are intravenously administered to a subject.

In one illustrative embodiment, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of genome edited cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

Some variation in dosage will necessarily occur depending on the condition of the subject being treated. The person responsible for administration will, in any event, determine the appropriate dose for the individual subject.

In particular embodiments, a genome edited cell therapy is used to treat, prevent, or ameliorate XLA, or a condition associated therewith, comprising administering to subject having one or more mutations and/or deletions in a BTK gene that results in little or no endogenous BTK expression, a therapeutically effective amount of the genome edited cells contemplated herein. In one embodiment, the genome edited cell therapy lacks functional endogenous BTK expression, but comprises an exogenous polynucleotide encoding a functional BTK polypeptide.

In various embodiments, a subject is administered an amount of genome edited cells comprising an exogenous polynucleotide encoding a functional BTK polypeptide, effective to increase BTK expression in the subject. In particular embodiments, the amount of BTK expression from the exogenous polynucleotide in genome edited cells comprising one or more deleterious mutations or deletions in a BTK gene is increased at least about 10%, at least about 20%, at least about 30%, at least about 40%, at least about 50%, at least about 60%, at least about 70%, at least about 80%, at least about 90%, at least about 100%, at least about 2-fold, at least about 5-fold, at least about 10-fold, at least about 50-fold, at least about 100-fold, at least about 200-fold, at least about 300-fold, at least about 400-fold, at least about 500-fold, or at least about 1000-fold, or more compared endogenous BTK expression.

One of ordinary skill in the art would be able to use routine methods in order to determine the appropriate route of administration and the correct dosage of an effective amount of a composition comprising genome edited cells contemplated herein. It would also be known to those having ordinary skill in the art to recognize that in certain therapies, multiple administrations of pharmaceutical compositions contemplated herein may be required to effect therapy.

One of the prime methods used to treat subjects amenable to treatment with genome edited hematopoietic stem and progenitor cell therapies is blood transfusion. Thus, one of the chief goals of the compositions and methods contemplated herein is to reduce the number of, or eliminate the need for, transfusions.

In particular embodiments, the drug product is administered once.

In certain embodiments, the drug product is administered 1, 2, 3, 4, 5, 6, 7, 8, 9, or 10 or more times over a span of 1 year, 2 years, 5, years, 10 years, or more.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

TALEN-Based Gene Editing at Target Site in Intron 2 of the Human BTK Gene

TALENs were generated to target sites T1-T4 within the human BTK gene. (FIG. 1A). The sequences of the TALENs were as follows:

TABLE 2

| TAL effector domain RVDs | |
|---|---|
| T1 (#1181) | |
| T1-F RVDs | HD NG HD NN NI HD NG NI NG NN NI NI NI NI HD NG |
| T1-R RVDs | HD NG NI NI NN NN HD HD NI NI NN NG HD HD NG |
| T2 (#1182) | |
| T2-F RVDs | NI NG HD NI NI NN NN NI HD NG NG NN NN HD HD NG |
| T2-R RVDs | NI HD HD NI NI HD NN NI NI NI NI NG NG NG NI HD HD NG |
| T3 (#1183) | |
| T3-F RVDs | NI NG NG NG HD HD NG NI NN HD HD NG NI NG NI NI HD NG |
| T3-R RVDs | NN NN HD NG NG HD NG NG NI NN NN NI HD HD NG NG NG |
| T4 | |
| T4-F RVDs | HD HD NI NG NG NG NN NI NI NI HD NG NI NN NN NG |
| T4-R RVDs | HD HD NG HD NI NG HD HD HD NG HD NG NG NN NN NG NG |

Figure 1B:
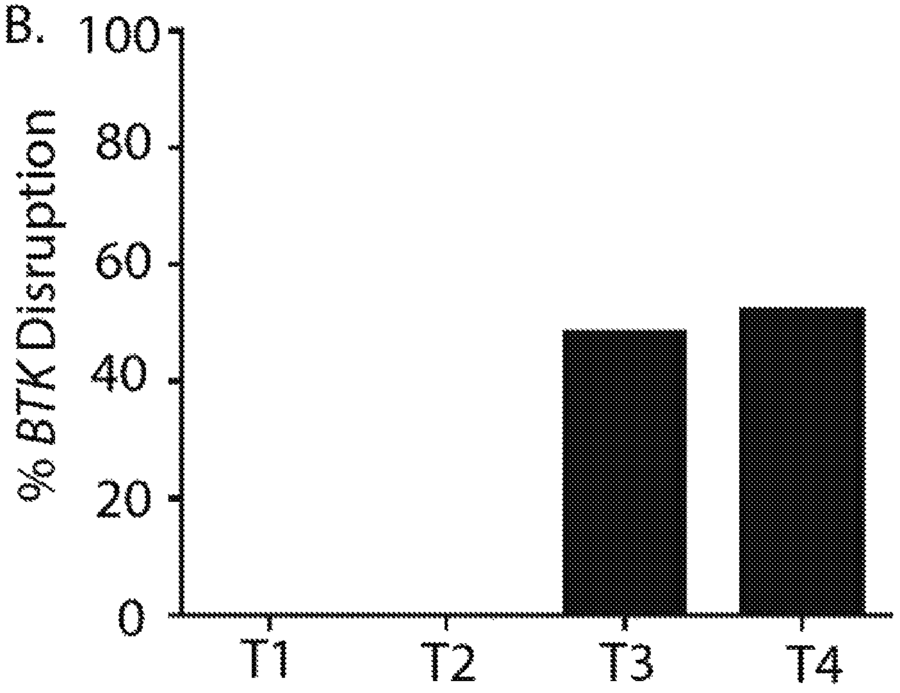
FIG. 1B shows the percent disruption achieved with each TALEN in primary T cells. Primary human T cells were cultured in T cell growth medium supplemented with IL-2 (50 ng/ml), IL-7 (5 ng/ml), and IL-15 (5 ng/ml) and stimulated using CD3/CD28 beads (Dynabeads, Life Technologies) for 48 hours. Beads were removed and cells rested overnight followed by electroporation using Neon Transfection system with either TALEN mRNA (1 μg of each RNA monomer) Cells were cultured for 5 more days and genomic DNA was extracted. The region surrounding the cut site was amplified and purified using PCR purification kit. 200 ng of purified PCR product was incubated with T7 endonuclease (NEB), analyzed on a gel and percent disruption quantified using Licor Image Studio Lite software. TALEN T3 was used in experiments in subsequent figures.

FIG. 1B shows the percent disruption achieved with each TALEN in primary T cells. Primary human T cells were cultured in T cell growth medium supplemented with IL-2 (50 ng/ml), IL-7 (5 ng/ml), and IL-15 (5 ng/ml) and stimulated using CD3/CD28 beads (Dynabeads, Life Technologies) for 48 hours. Beads were removed and cells rested overnight followed by electroporation using Neon Transfection system with either TALEN mRNA (1 μg of each RNA monomer) Cells were cultured for 5 more days and genomic DNA was extracted. The region surrounding the cut site was amplified and purified using PCR purification kit. 200 ng of purified PCR product was incubated with T7 endonuclease (NEB), analyzed on a gel and percent disruption quantified using Licor Image Studio Lite software. TALEN T3 was used in experiments in subsequent figures.

Figure 1C:
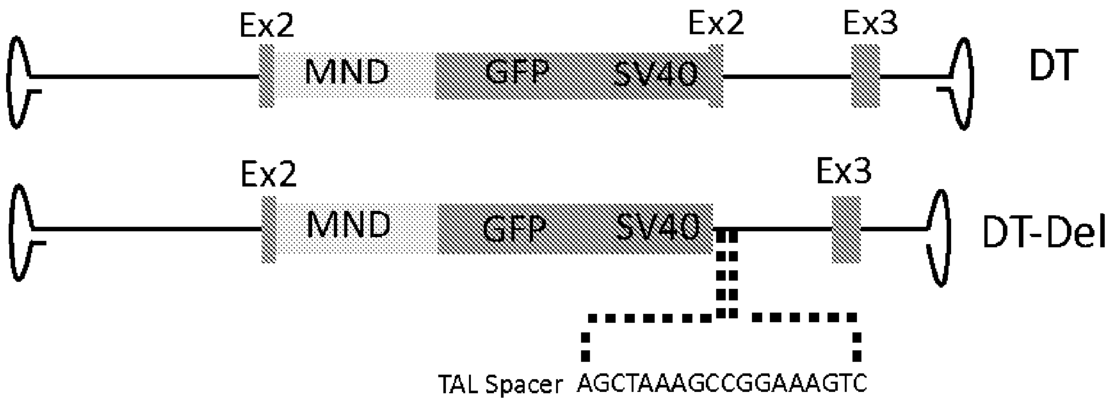
FIG. 1C shows a schematic of AAV donor templates for editing BTK gene using TALENs. DT AAV vector has 1 kb of homology arms flanking an MND promoter driven green fluorescent protein (GFP) cassette. DT-Del AAV donor has deletion of the genomic region spanning the end of the 5' homology arm to the TAL spacer domain (SEQ ID NO: 72) resulting in a partial deletion of the second exon and intron to abolish cleavage by the TALEN.

FIG. 1C shows a schematic of AAV donor templates for editing BTK gene using TALENs. DT AAV vector has 1 kb of homology arms flanking an MND promoter driven green fluorescent protein (GFP) cassette. DT-Del AAV donor has deletion of the genomic region spanning the end of the 5' homology arm to the TAL spacer domain resulting in a partial deletion of the second exon and intron to abolish cleavage by the TALEN.

Figure 1D:
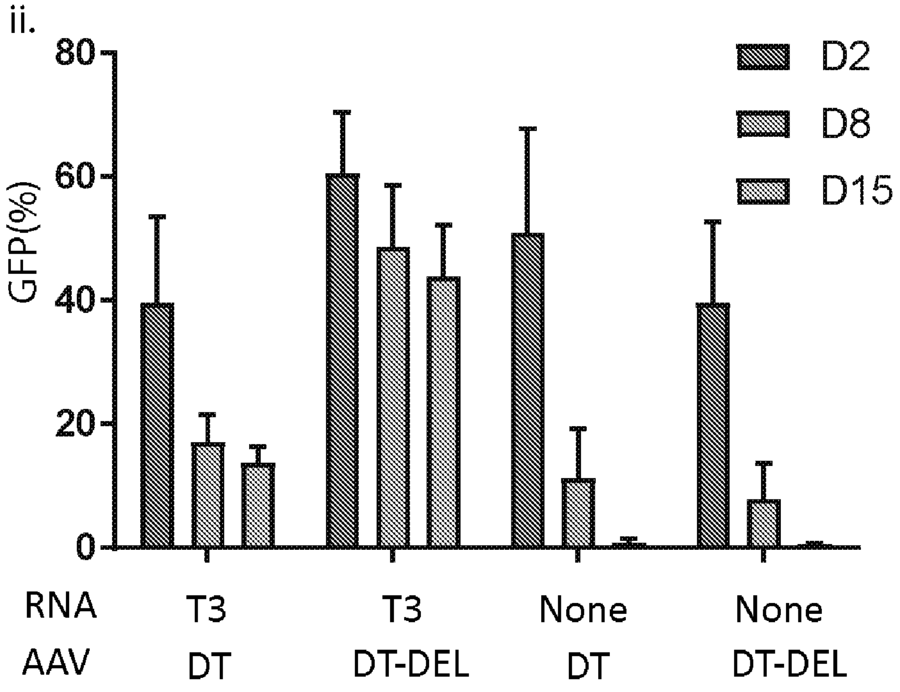
FIG. 1D shows editing in primary T cells using TALENs and AAV donor templates. Bar graphs depicts the time course of GFP expression. Percent homologous recombination (HR) is reported as percent (%) GFP at day 15.

FIG. 1D shows editing in primary T cells using TALENs and AAV donor templates. Bar graphs depicts the time course of GFP expression. Percent homologous recombination (HR) is reported as percent (%) GFP at day 15.

Figure 1E:
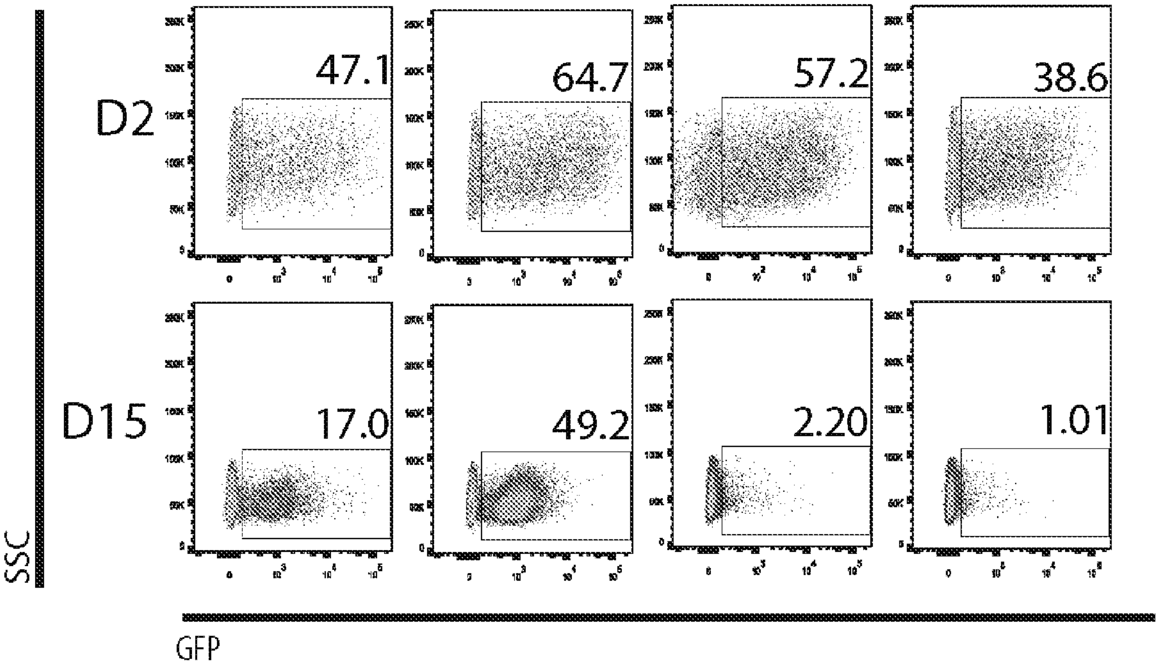
FIG. 1E shows representative FACS plots showing GFP expression at days 2 and 15 post-editing of primary T cells using co-delivery of TALENs and AAV donors.

FIG. 1E shows representative FACS plots showing GFP expression at days 2 and 15 post-editing of primary T cells using co-delivery of TALENs and AAV donors.

Example 2

CRISPR/Cas Gene Editing at Target Site in Intron 2 of the Human BTK Gene

Figure 2A:
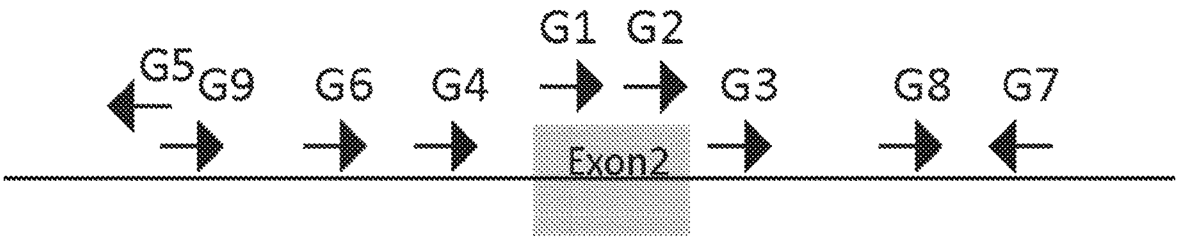
FIG. 2A shows a schematic of BTK locus with CRISPR guides annotated. Location of the guide RNAs (G1-G9) within the human BTK gene is shown. Schema is not drawn to scale.

TALENs were generated to target sites within the human BTK gene corresponding to guide RNA locations G1-G9. (FIG. 2A). The gRNA sequences were as follows:

| Guide | Sequence |
|---|---|
| G1 | AGCTATGGCCGCAGTGATTC |
| G2 | AGGCGCTTCTTGAAGTTTAG |
| G3 | ATGAGTATGACTTTGAACGT |
| G4 | AGGGATGAGGATTAATGTCC |

-continued

| Guide | Sequence |
|---|---|
| G5 | ACACTGAATTGGGGGGGGAT |
| G6 | AACTAGGTAGCTAGGCTGAG |
| G7 | GCTTTAGCTAGTTATAGGCT |
| G8 | AGAGGTAAATTTTCGTTGGT |
| G9 | GATGCACACTGAATTGGGGG |

Figure 2B:
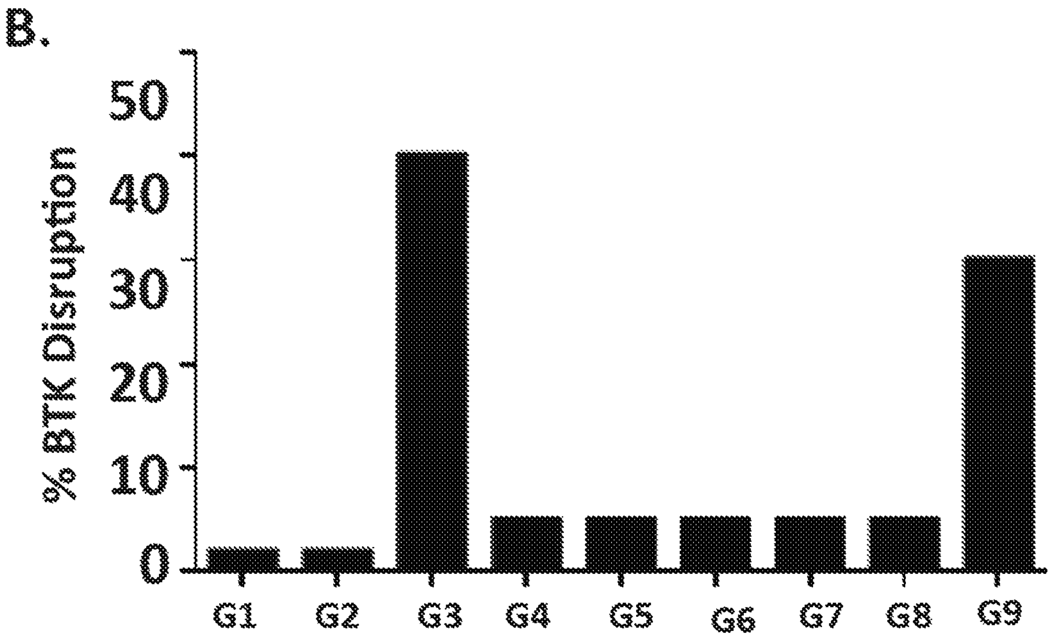
FIG. 2B shows percent (%) disruption at the BTK locus with guides G1 through G9 as determined by T7 endonuclease (New England Biolabs). Percent disruption was quantified using Licor Image Studio Lite software. Guide G3 was used in experiments in subsequent figures.

FIG. 2B shows percent (%) disruption at the BTK locus with guides G1 through G9 as determined by T7 endonuclease (New England Biolabs). Percent disruption was quantified using Licor Image Studio Lite software. Guide G3 was used in experiments in subsequent figures.

Figure 2C:
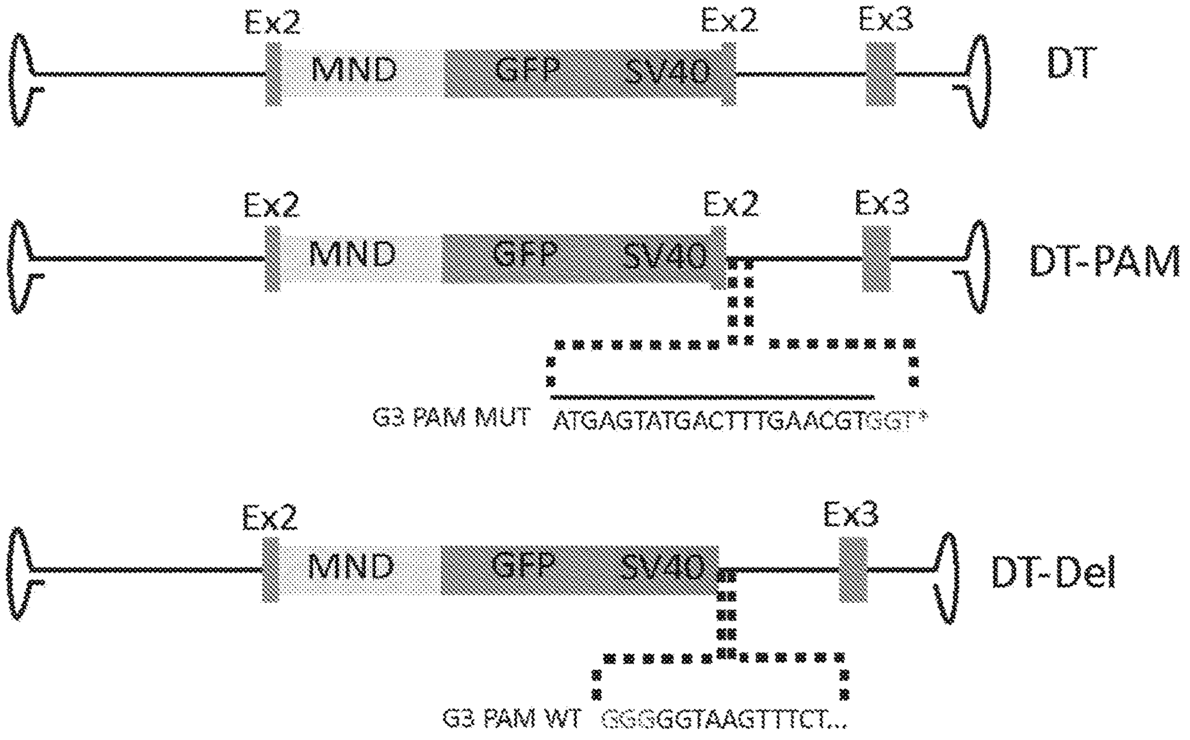
FIG. 2C shows chematic of three exemplary AAV donor templates for editing BTK gene using CRISPR-Cas. DT AAV vector has 1 kb of homology arms flanking an MND promoter driven green fluorescent protein (GFP). DT-PAM AAV donor has mutations in PAM sequence (SEQ ID NO: 73) to abolish cleavage by guide G3. The DT-Del vector has a deletion (SEQ ID NO: 74) to abolish cleavage by guide G3.

FIG. 2C shows chematic of three exemplary AAV donor templates for editing BTK gene using CRISPR-Cas. DT AAV vector has 1 kb of homology arms flanking an MND promoter driven green fluorescent protein (GFP). DT-PAM AAV donor has mutations in PAM sequence to abolish cleavage by guide G3. The DT-Del vector has a deletion to abolish cleavage by guide G3.

Example 3

Figure 2D:
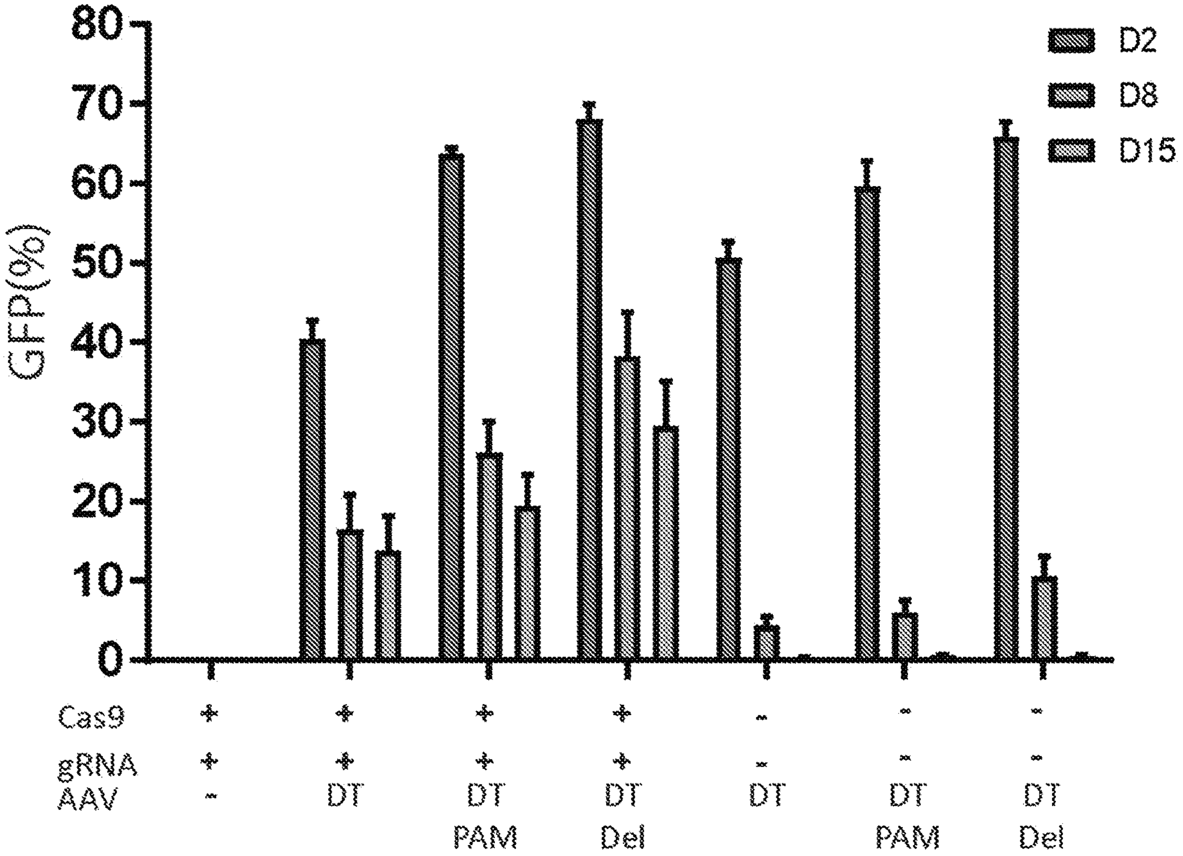
FIG. 2D shows editing in primary T cells using co-delivery of Cas9 plus guides and AAV donor templates. Primary human $CD3^+$ T cells were cultured and bead stimulated. Cells were then transfected with Ribonucleoprotein complex (RNP) of Cas9 protein and single guide RNA and AAV donors added two hours later at 20% of culture volume. Cells were analyzed for GFP expression on Days 2, 8 and 15. GFP expression at day 15 is indicative of homology directed repair (HDR).

CRISPR/Cas Gene Editing in Primary T Cells by Co-Delivery of Ribonucleoprotein complex (RNP) of Cas9 protein and single guide RNA and AAV donors FIG. 2D shows editing in primary T cells using co-delivery of Cas9 plus guides and AAV donor templates. Primary human CD3+ T cells were cultured and bead stimulated. Cells were then transfected with Ribonucleoprotein complex (RNP) of Cas9 protein and single guide RNA and AAV donors added two hours later at 20% of culture volume. Cells were analyzed for GFP expression on Days 2, 8 and 15. GFP expression at day 15 is indicative of homology directed repair (HDR).

Figure 2E:
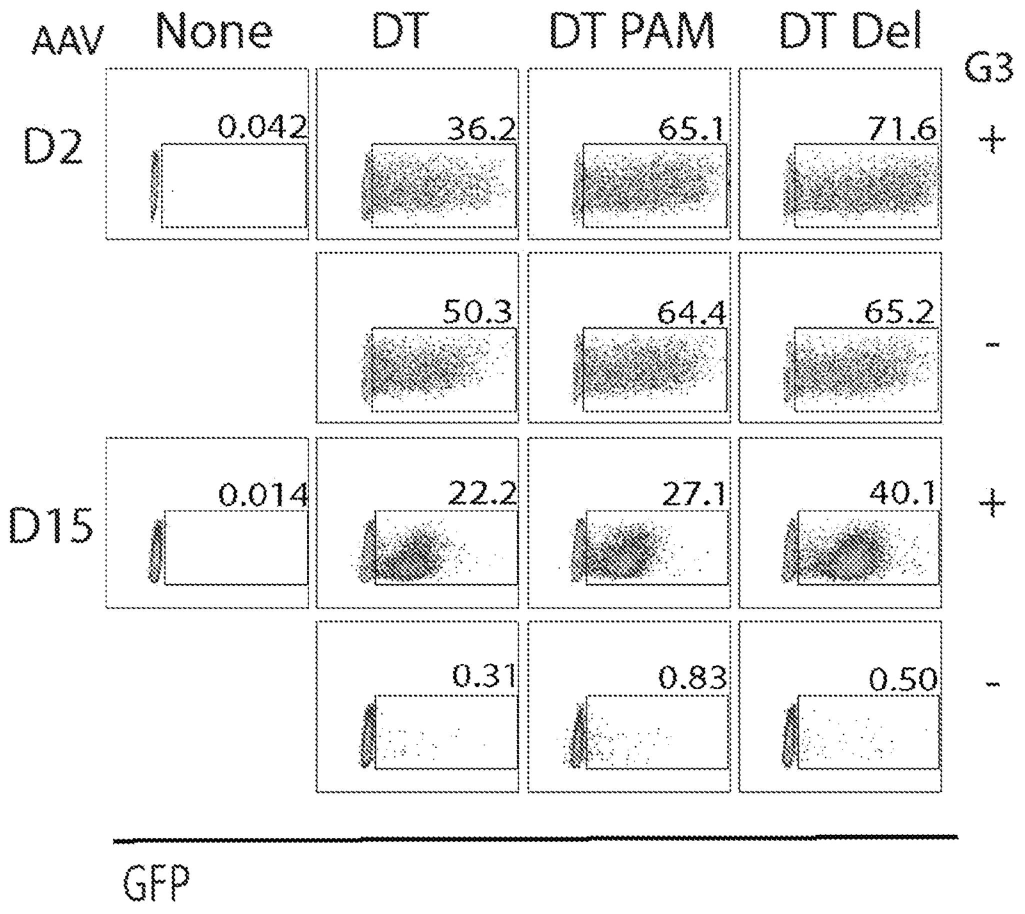
FIG. 2E shows representative FACS plots showing GFP expression at days 2 and 15 post editing of primary T cells using RNPs plus AAV donors.

FIG. 2E shows representative FACS plots showing GFP expression at days 2 and 15 post editing of primary T cells using RNPs plus AAV donors.

Example 4

GENE EDITING IN CD34$^{+}$T CELLS WITH CRISPR/CAS OR TALEN-BASED SYSTEMS

Figure 3A:
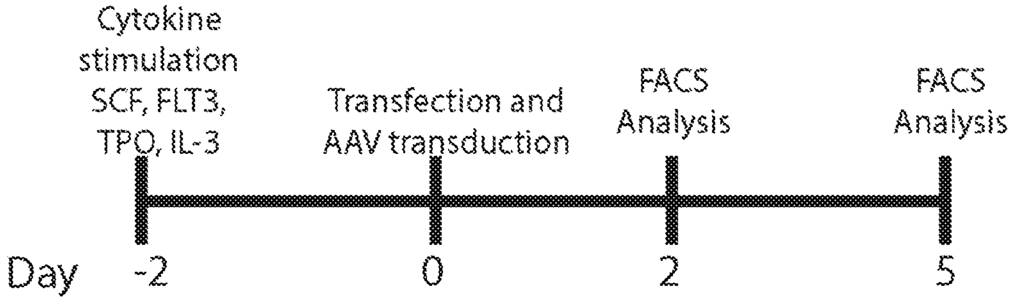
FIG. 3A shows a schematic of human $CD34^+$ cell editing protocol. Adult human Mobilized $CD34^+$ cells were cultured in SCGM media supplemented with TPO, SCF, FLT3L (100 ng/ml) and IL3 (60 ng/ml) for 48 hours, followed by electroporation using Neon electroporation system with either TALENs or Ribonucleoprotein complex (RNP) of Cas9 protein and single guide RNA mixed in 1:1.2 ratio. The sgRNA was purchased from Trilink Biotechnologies and has chemically modified nucleotides at the three terminal positions at 5' and 3' ends. The cells were analyzed by flow cytometry on days 2 and 5.

FIG. 3A shows a schematic of human CD34$^{+}$ cell editing protocol. Adult human Mobilized CD34$^{+}$ cells were cultured in SCGM media supplemented with TPO, SCF, FLT3L (100 ng/ml) and IL3 (60 ng/ml) for 48 hours, followed by electroporation using Neon electroporation system with either TALENs or Ribonucleoprotein complex (RNP) of Cas9 protein and single guide RNA mixed in 1:1.2 ratio. The sgRNA was purchased from Trilink Biotechnologies and has chemically modified nucleotides at the three terminal positions at 5' and 3' ends. The cells were analyzed by flow cytometry on days 2 and 5.

Figure 3B:
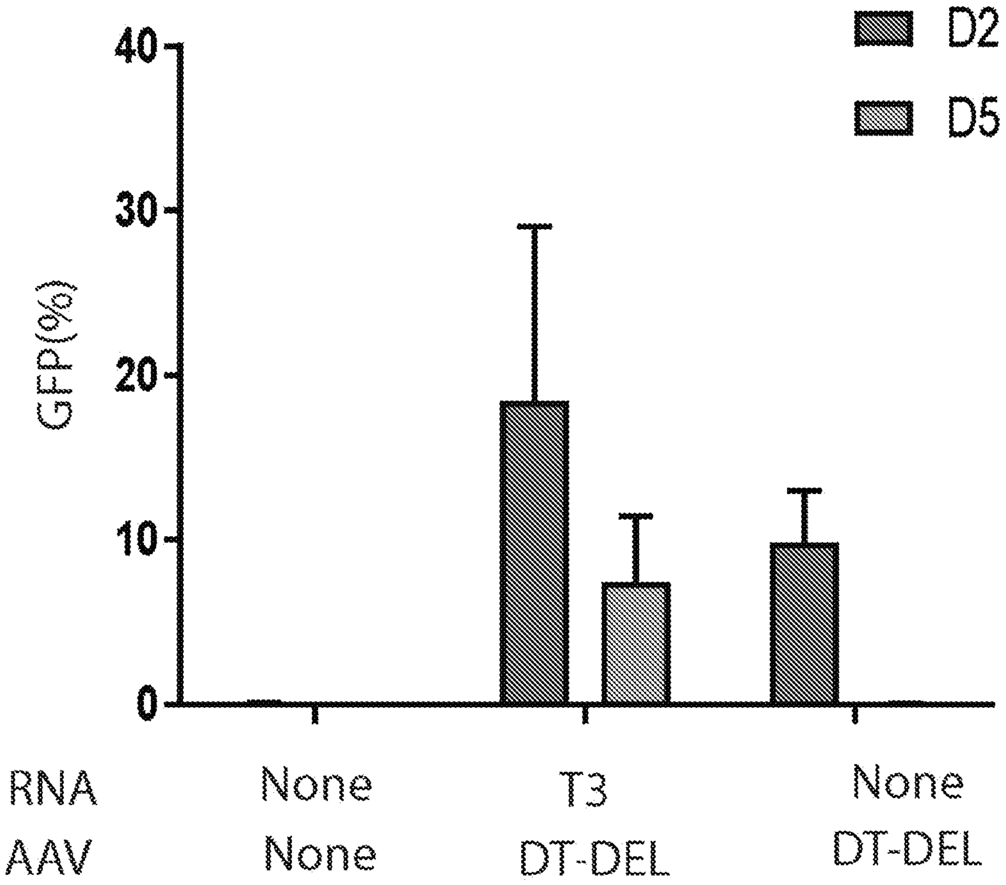
FIG. 3B shows editing of the BTK locus in $CD34^+$ HSCs using co-delivery of TALEN mRNA and AAV donor template. Adult mobilized human $CD34^+$ cells were cultured in SCGM media as described before followed by electroporation using Neon electroporation system with TALEN mRNA. AAV vector carrying the donor template was added immediately after electroporation. Controls included un-manipulated cells and cells transduced with AAV only without transfection of a nuclease (AAV). Bar graphs depict % GFP at day 5, indicative of HDR.

FIG. 3B shows editing of the BTK locus in CD34$^{+}$HSCs using co-delivery of TALEN mRNA and AAV donor template. Adult mobilized human CD34$^{+}$ cells were cultured in SCGM media as described before followed by electroporation using Neon electroporation system with TALEN mRNA. AAV vector carrying the donor template was added immediately after electroporation. Controls included un-manipulated cells and cells transduced with AAV only without transfection of a nuclease (AAV). Bar graphs depict % GFP at day 5, indicative of HDR.

Figure 3C:
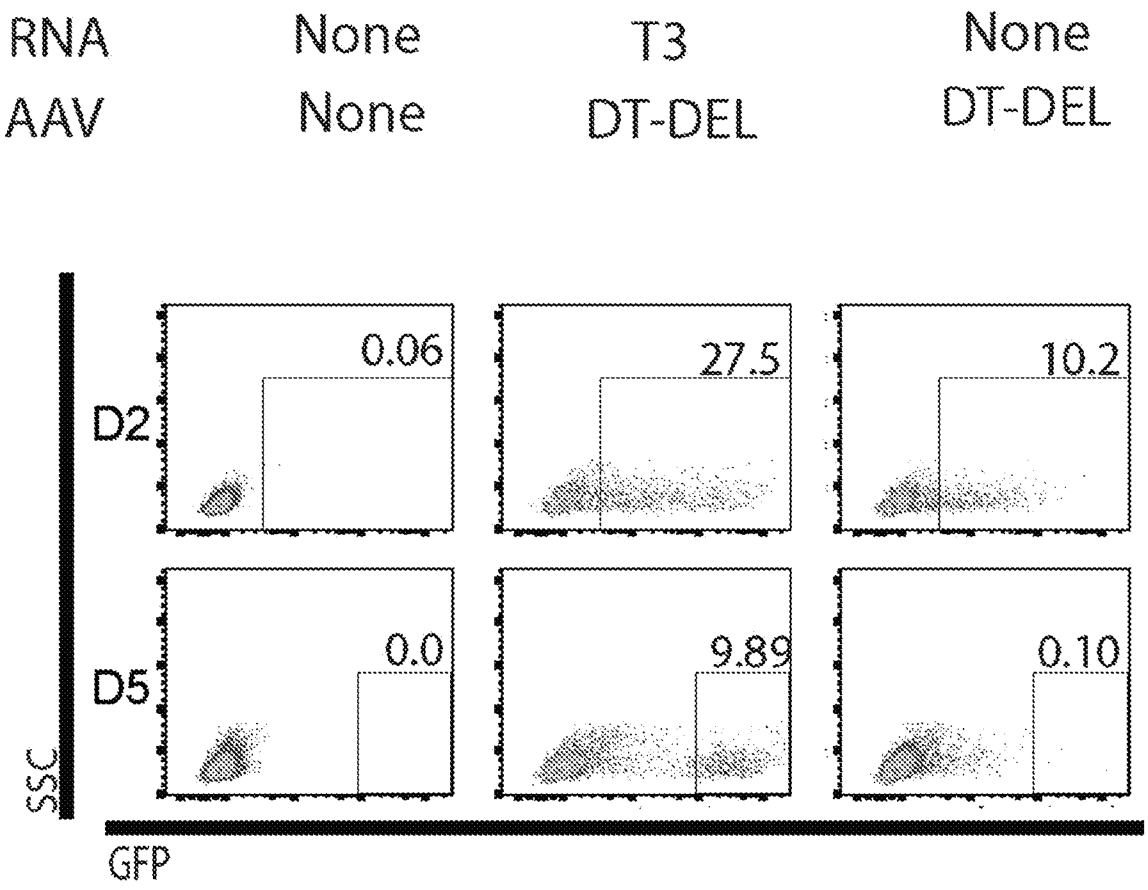
FIG. 3C shows FACS plots depicting GFP expression from Mock, AAV or AAV plus TALEN treated $CD34^+$ cells, 2 and 5 days post editing.

FIG. 3C shows FACS plots depicting GFP expression from Mock, AAV or AAV plus TALEN treated CD34$^{+}$ cells, 2 and 5 days post editing.

Figure 3D:
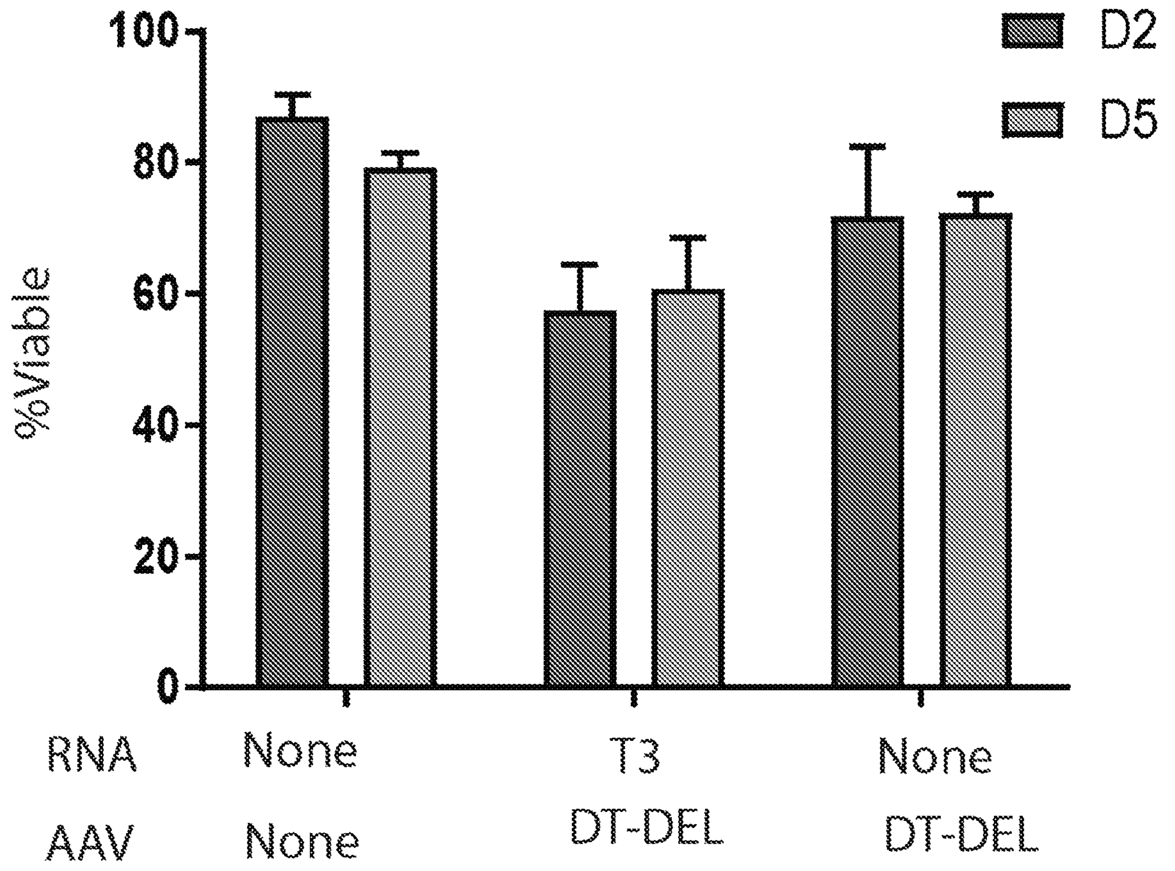
FIG. 3D shows $CD34^+$ cell viability post editing with TALENs and AAV donors. Bar graphs represent viability of mock and AAV only and AAV plus TALEN treated cells 2 and 5 days post editing.

FIG. 3D shows CD34$^{+}$ cell viability post editing with TALENs and AAV donors. Bar graphs represent viability of mock and AAV only and AAV plus TALEN treated cells 2 and 5 days post editing.

Figure 3E:
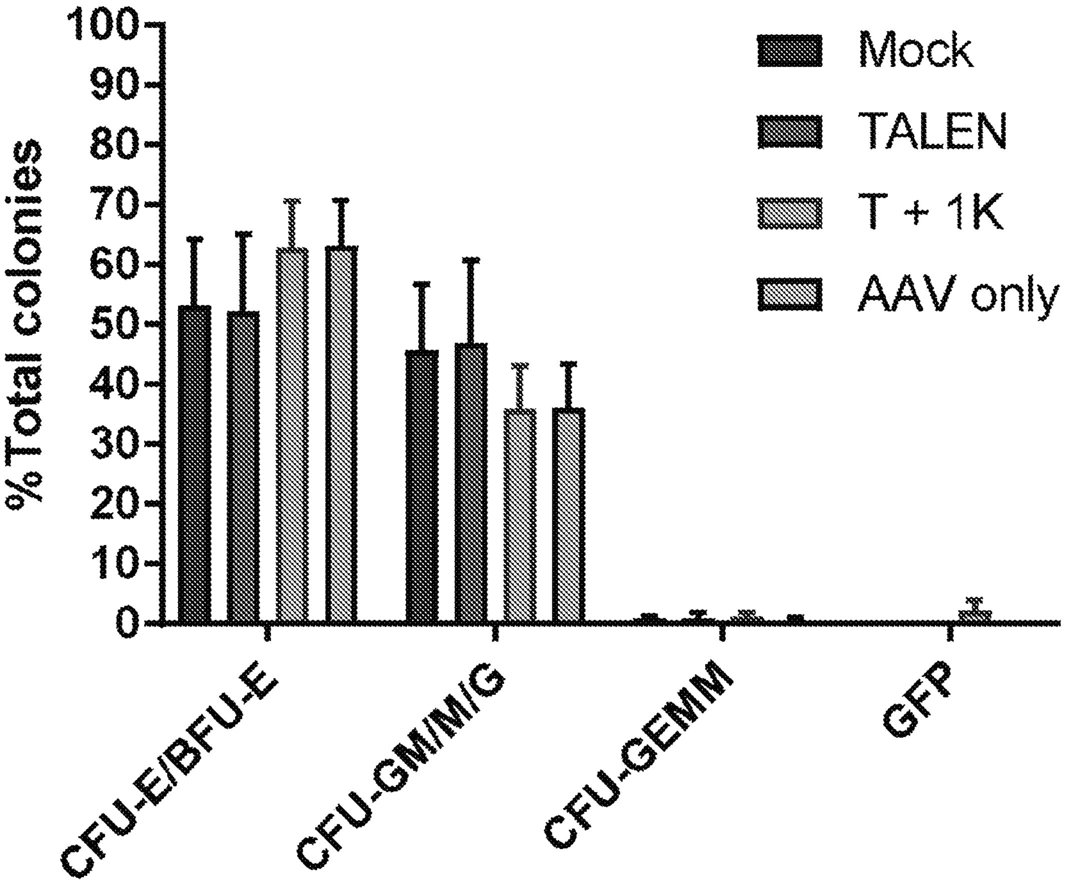
FIG. 3E shows CFU assay for TALEN edited $CD34^+$ cells. TALEN edited, TALEN only, AAV only and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 independent donors. Data are presented as mean±SEM.

FIG. 3E shows CFU assay for TALEN edited CD34$^{+}$ cells. TALEN edited, TALEN only, AAV only and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 independent donors. Data are presented as mean±SEM.

Figure 4A:
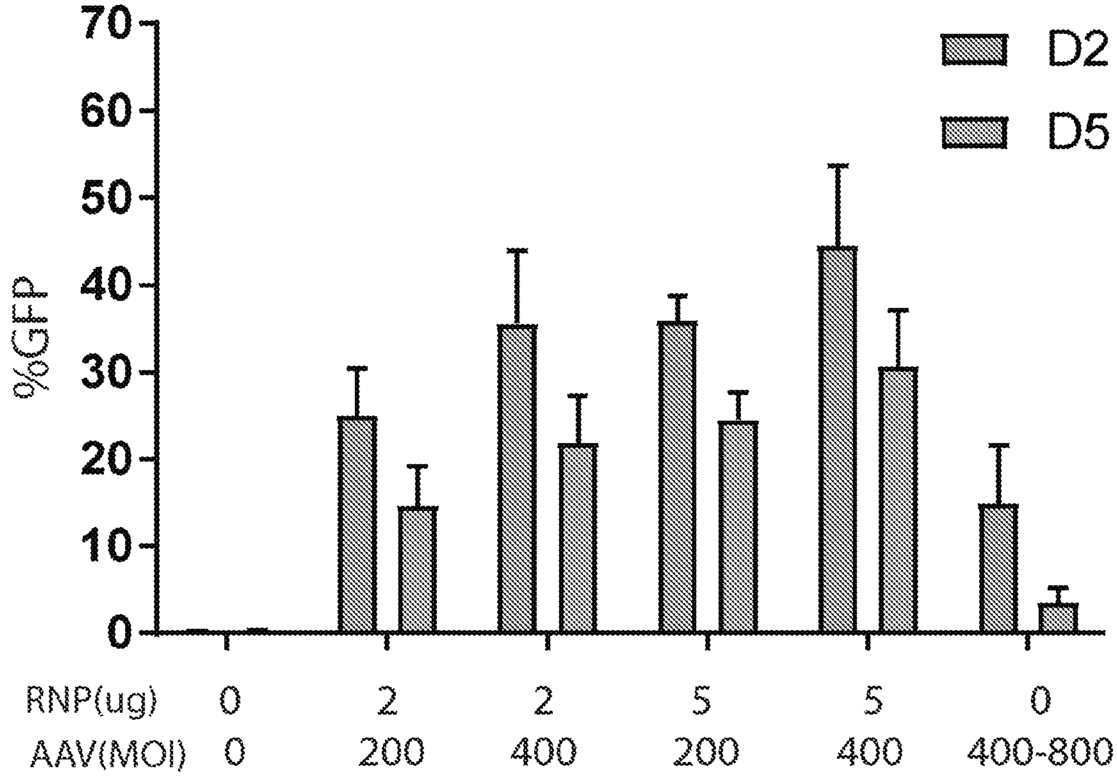
FIG. 4A shows editing of the BTK locus in $CD34^+$ HSCs using co-delivery of RNPs and AAV donor template. Adult mobilized human $CD34^+$ cells were cultured in SCGM media as described before followed by electroporation using Neon electroporation system with RNP complex. AAV vector carrying the donor template was added immediately after electroporation. Controls included un-manipulated cells and cells transduced with AAV only without transfection of a nuclease (AAV). Bar graphs depict % GFP at day 5, indicative of HDR.

FIG. 4A shows editing of the BTK locus in CD34$^{+}$HSCs using co-delivery of RNPs and AAV donor template. Adult mobilized human CD34$^{+}$ cells were cultured in SCGM media as described before followed by electroporation using Neon electroporation system with RNP complex. AAV vector carrying the donor template was added immediately after electroporation. Controls included un-manipulated cells and cells transduced with AAV only without transfection of a nuclease (AAV). Bar graphs depict % GFP at day 5, indicative of HDR.

Figure 4B:
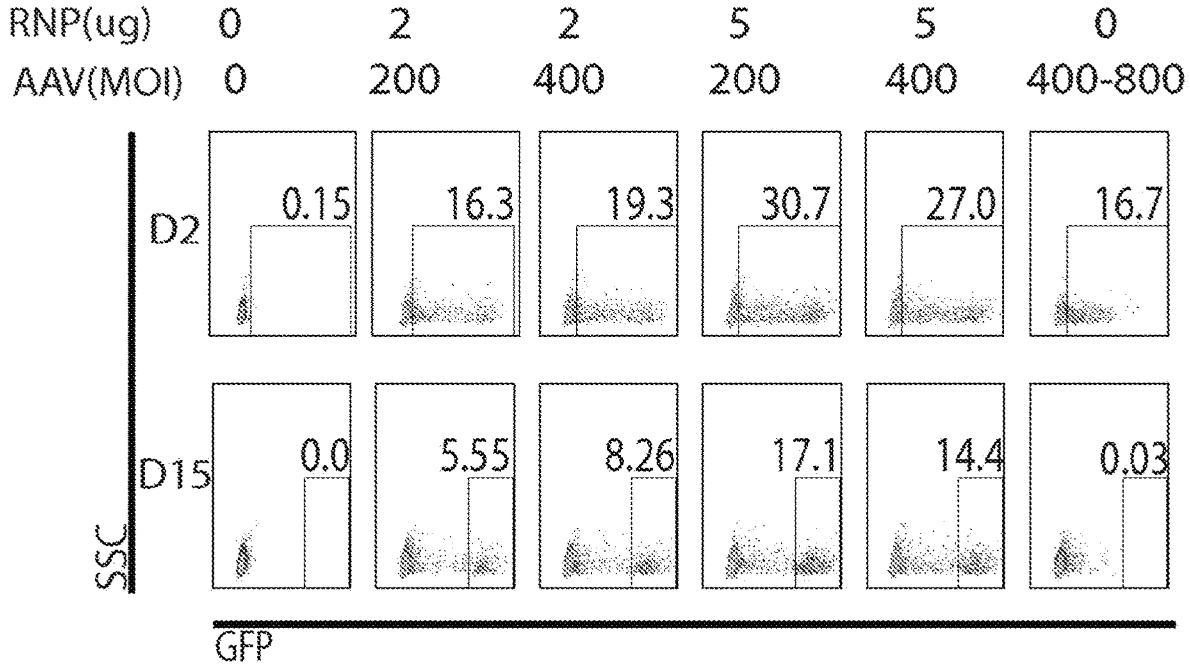
FIG. 4B shows the same experiment as FIG. 4A and depicts representative FACs plots showing GFP expression at days 2 and 5.

FIG. 4B shows the same experiment as FIG. 4A and depicts representative FACs plots showing GFP expression at days 2 and 5.

Figure 4C:
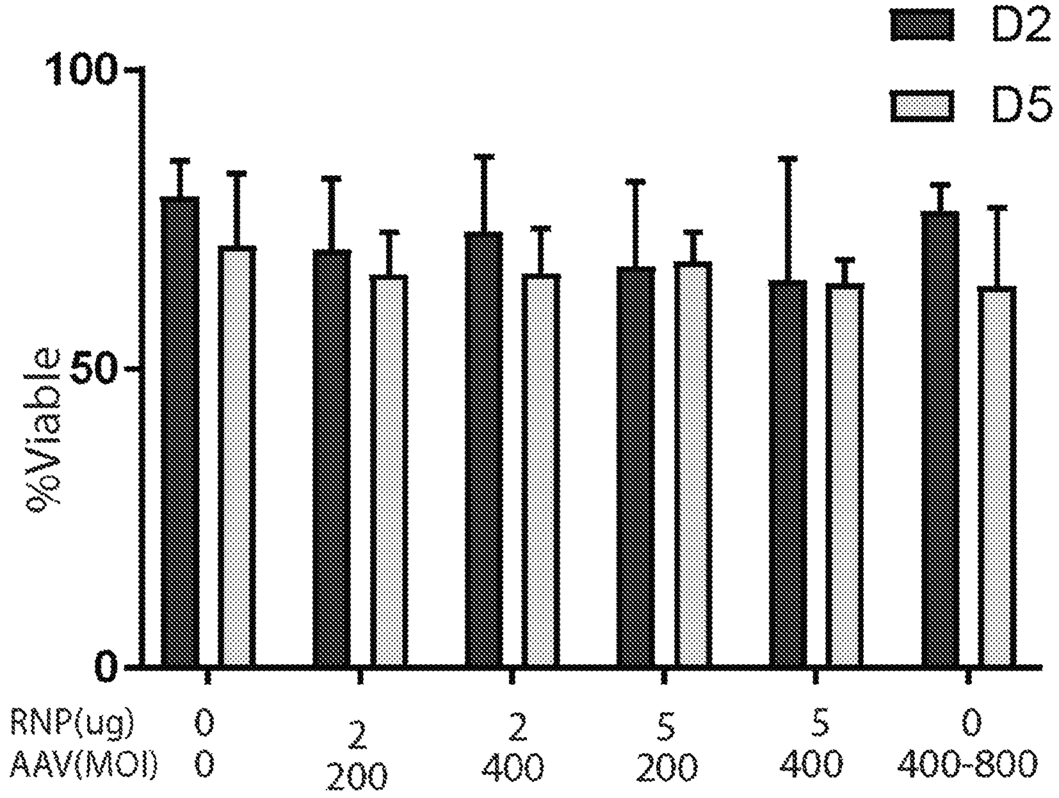
FIG. 4C shows $CD34^+$ cell viability post editing with RNPs and AAV donors. Bar graphs represent viability of mock and AAV only and AAV plus RNP treated cells (at various RNP and AAV doses) 2 and 5 days post editing.

FIG. 4C shows CD34$^{+}$ cell viability post editing with RNPs and AAV donors. Bar graphs represent viability of mock and AAV only and AAV plus RNP treated cells (at various RNP and AAV doses) 2 and 5 days post editing.

Figure 4D:
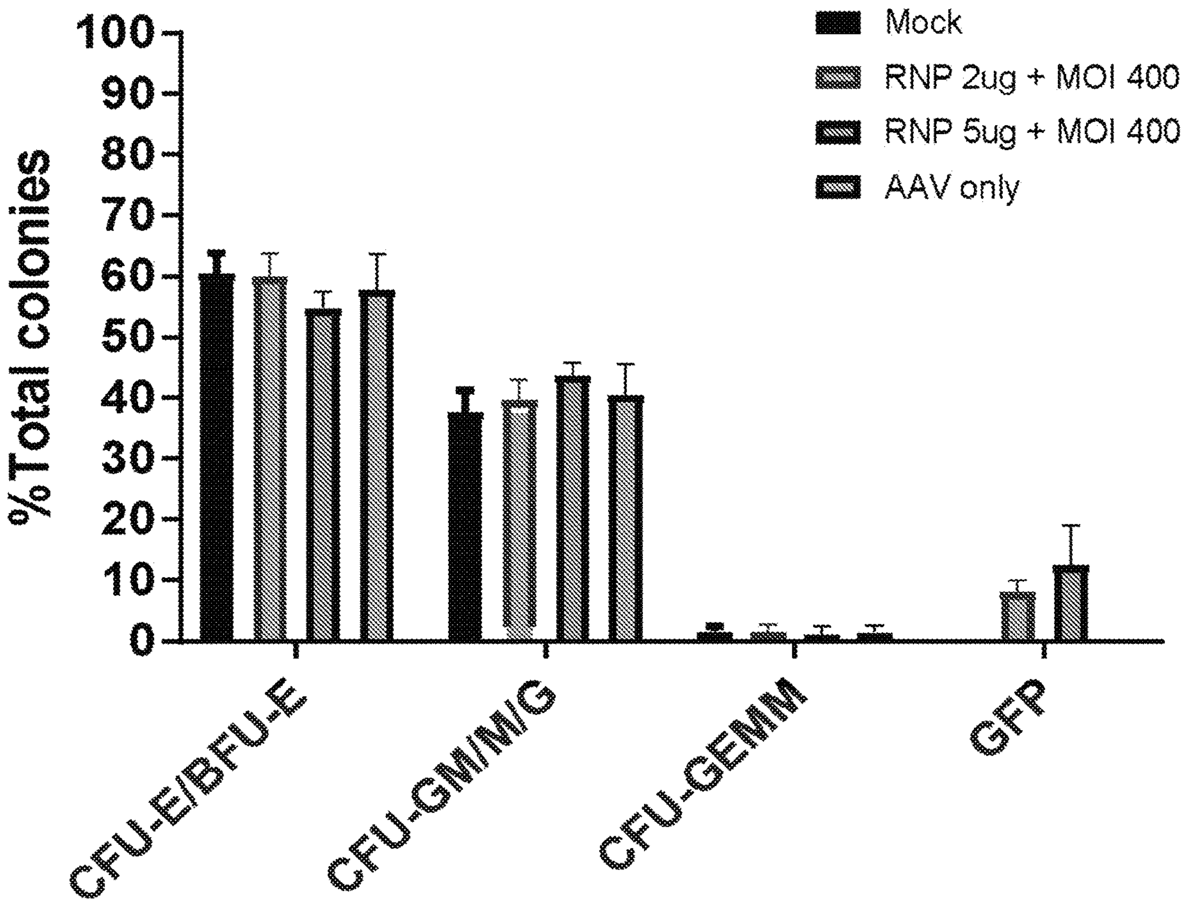
FIG. 4D shows CFU assay for RNP edited $CD34^+$ cells. RNP edited, AAV only and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 independent donors. Data are presented as mean±SEM.

FIG. 4D shows CFU assay for RNP edited CD34$^{+}$ cells. RNP edited, AAV only and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 independent donors. Data are presented as mean±SEM.

Figure 5A:
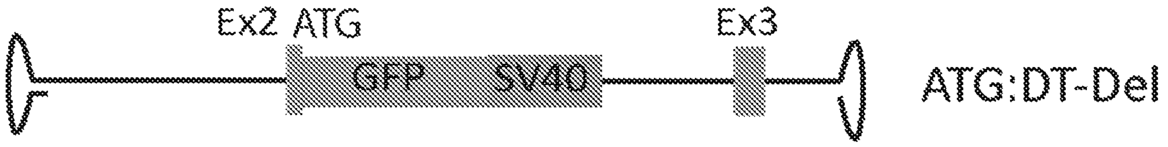
FIG. 5A shows schematic of promoter-less AAV donor template expressing GFP. This vector contains a GFP, a truncated woodchuck hepatitis virus posttranscriptional regulatory element (WPRE3) and an SV40 polyadenylation signal. This insert is flanked on either side by 0.5 kb homology arms to the BTK locus.

FIG. 5A shows schematic of promoter-less AAV donor template expressing GFP. This vector contains a GFP, a truncated woodchuck hepatitis virus posttranscriptional regulatory element (WPRE3) and an SV40 polyadenylation signal. This insert is flanked on either side by 0.5 kb homology arms to the BTK locus.

Figure 5B:
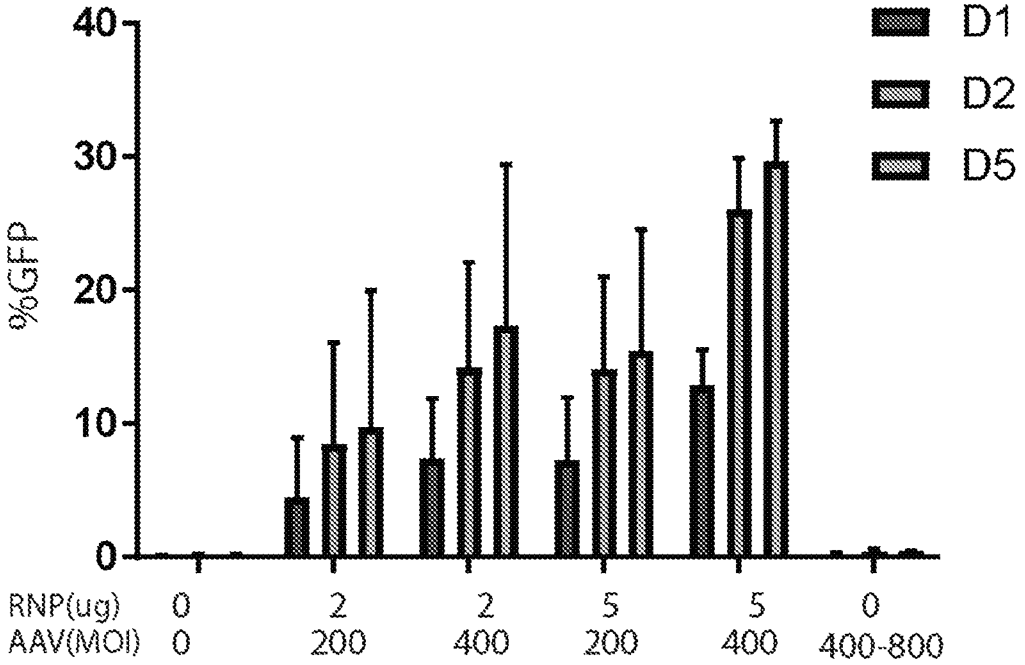
FIG. 5B shows editing of the BTK locus using promoter-less GFP vector in $CD34^+$ HSCs using co-delivery of RNPs and AAV donor template. Bar graphs depict % GFP at days 1, 2 and 5, % GFP at day 5 is indicative of HDR.

FIG. 5B shows editing of the BTK locus using promoter-less GFP vector in CD34$^{+}$HSCs using co-delivery of RNPs and AAV donor template. Bar graphs depict % GFP at days 1, 2 and 5, % GFP at day 5 is indicative of HDR.

Figure 5C:
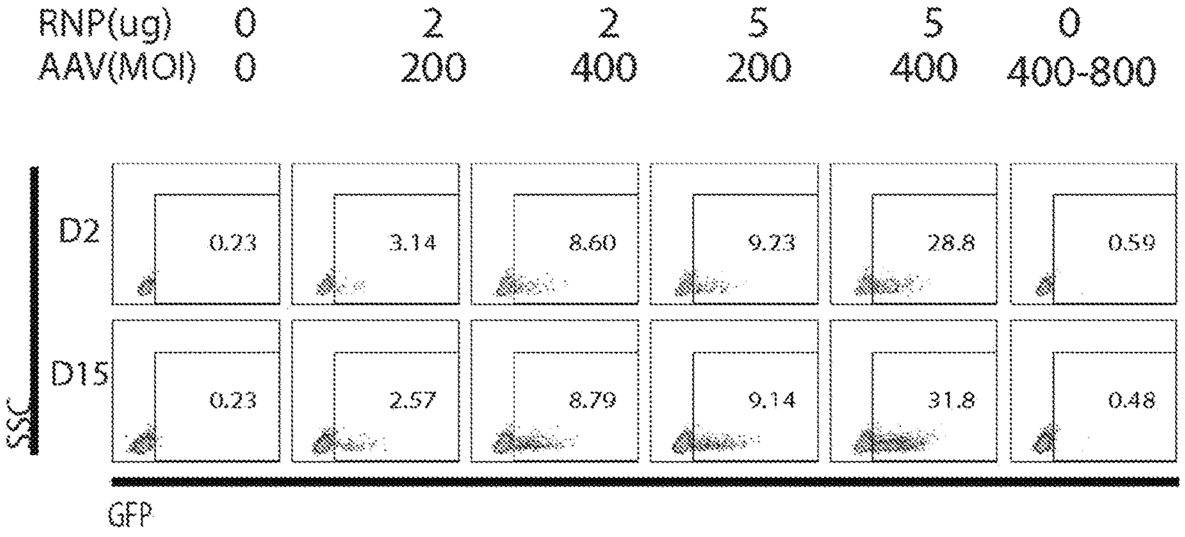
FIG. 5C shows the same experiment as FIG. 4A and depicts representative FACs plots showing GFP expression at days 2 and 5.

FIG. 5C shows the same experiment as FIG. 4A and depicts representative FACs plots showing GFP expression at days 2 and 5.

Figure 5D:
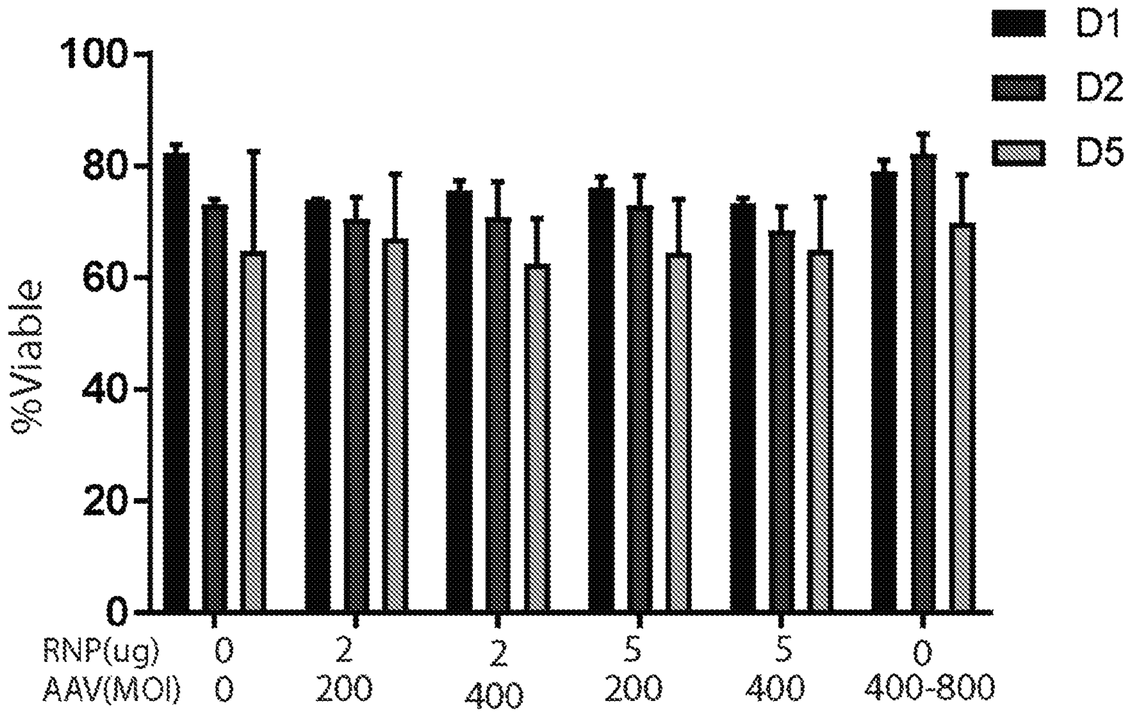
FIG. 5D shows $CD34^+$ cell viability post editing with RNPs and promoter-less AAV donor. Bar graphs represent viability of mock and AAV only and AAV plus RNP treated cells (at various RNP and AAV doses) 1, 2 and 5 days post editing. % GFP at day 5 is indicative of % HDR.

FIG. 5D shows CD34$^{+}$ cell viability post editing with RNPs and promoter-less AAV donor. Bar graphs represent viability of mock and AAV only and AAV plus RNP treated cells (at various RNP and AAV doses) 1, 2 and 5 days post editing. % GFP at day 5 is indicative of % HDR.

Figure 5E:
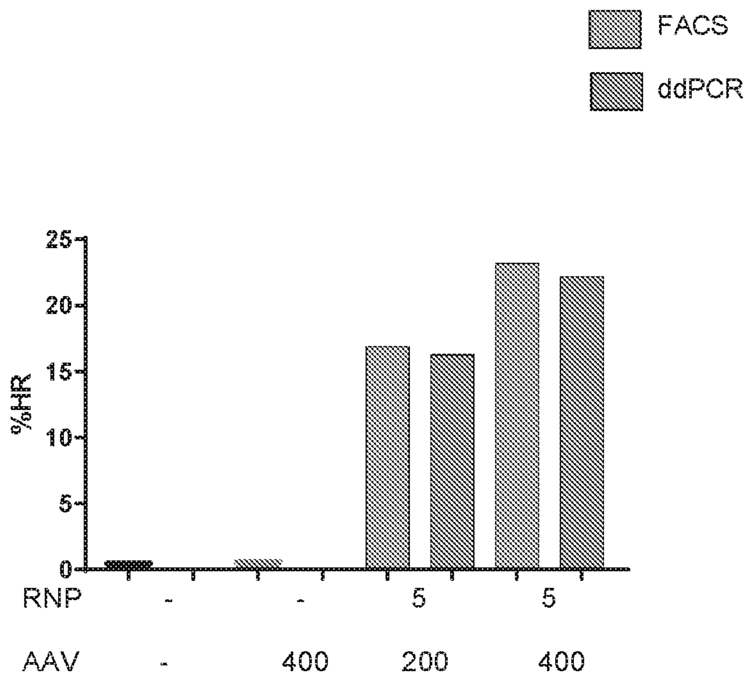
FIG. 5E shows digital droplet PCR assay for determining HDR. Genomic DNA was isolated from hematopoietic stem and progenitor cells (HSPCs) using a DNeasy Blood and Tissue kit (Qiagen). To assess editing rates, "in-out" droplet digital PCR was performed with the forward primer binding within the AAV insert and the reverse primer binding the BTK locus outside the region of homology. A control amplicon of similar size was generated for the ActB gene to serve as a control. All reactions were performed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe, 50 ng of genomic DNA, and 1% DMSO. Droplets were analyzed on the QX200 Droplet Digital PCR System (Bio-Rad) using QuantaSoft software (Bio-Rad).

FIG. 5E shows digital droplet PCR assay for determining HDR. Genomic DNA was isolated from hematopoietic stem and progenitor cells (HSPCs) using a DNeasy Blood and Tissue kit (Qiagen). To assess editing rates, "in-out" droplet digital PCR was performed with the forward primer binding within the AAV insert and the reverse primer binding the BTK locus outside the region of homology. A control amplicon of similar size was generated for the ActB gene to serve as a control. All reactions were performed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe, 50 ng of genomic DNA, and 1% DMSO. Droplets were analyzed on the QX200 Droplet Digital PCR System (Bio-Rad) using QuantaSoft software (Bio-Rad).

Figure 6A:
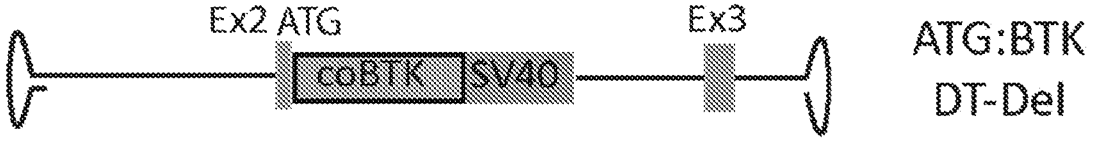
FIG. 6 shows a schematic of AAV donor template expressing codon optimized BTK.

FIG. 6 shows a schematic of AAV donor template expressing codon optimized BTK.

Example 5

AAV TARGETING VECTORS_SEQUENCES

#DT (#1177) (SEQ ID NO: 19)

AAV targeting vector for BTK locus. This vector contains an MND promoter, eGFP (enhanced green fluorescent protein) and an SV40 polyadenylation signal and is flanked by ~1 kb homology arms.

DT-Del (#1233) (SEQ ID NO: 20)

This vector contains an MND promoter, eGFP and an SV40 polyadenylation signal. This insert is flanked on either side by roughly 1 kb homology arms to the BTK locus. This vector is specifically designed for use with BTK TALEN T3. The TALEN binding site is deleted to abolish cleavage by the TALEN.

DT-PAM 1254 (SEQ ID NO: 21)

This vector contains an MND promoter, eGFP and an SV40 polyadenylation signal. This insert is flanked on either side by roughly 1 kb homology arms to the BTK locus. This vector is designed to work with BTK guide G3 as the PAM site is deleted to abolish cleavage of repair template by the guide.

DT-PAM mut (#1251) (SEQ ID NO: 22)

This vector contains an MND promoter, eGFP and an SV40 polyadenylation signal. This insert is flanked on either side by roughly 1 kb homology arms to the BTK locus. The PAM site is mutated to abolish cleavage by guide G3.

ATG-DT-Del (#1375) (SEQ ID NO: 23)

This vector contains eGFP, a truncated woodchuck hepatitis virus posttranscriptional regulatory element (WPRE3) and an SV40 polyadenylation signal and is flanked by 0.5 kb homology rams to the BTK locus. It is designed to work with BTK guide G3.

ATG-BTK DT-DEL (#1379) (SEQ ID NO: 24)

This vector contains a codon-optimized BTK cDNA, a truncated woodchuck hepatitis virus posttranscriptional regulatory element (WPRE3) and an SV40 polyadenylation signal. This insert is flanked on either side by 0.5 kb homology arms to the BTK locus and is specifically designed to work with BTK guide G3.

Example 6

HDR: NHEJ Ratios in CD34$^+$T Cells with CRISPR/Cas or TALEN-Based Systems

Summary

Figure 7:
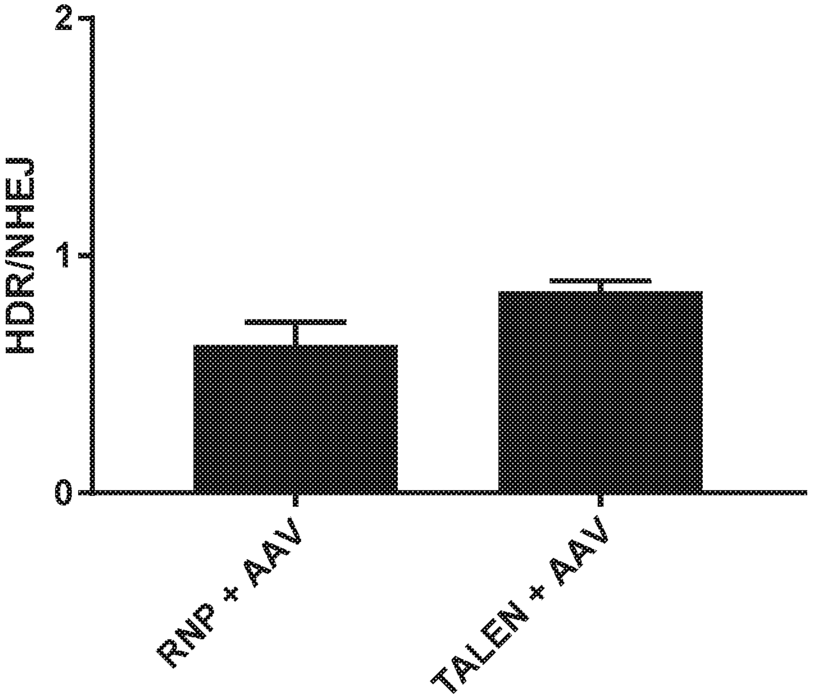
FIG. 7 shows a comparison of ratio of HDR (homology directed repair) versus NHEJ (non-homologous end joining) in cells edited with TALEN plus AAV or RNP plus AAV.

FIG. 7 depicts comparison of the ratio of homology directed repair: non-homologous end joining with RNP to the TALENs platform (when co-delivered with rAAV6 targeting vectors). A higher HDR: NHEJ ratio is favorable as it means that the cells are primed to repair the cut using HDR instead of mutagenic NHEJ.

While high-levels of HDR are achieved with both nuclease platforms, the HDR: NHEJ ratio is higher for TALEN plus AAV compared to RNP plus AAV delivery.

Figure 8A:
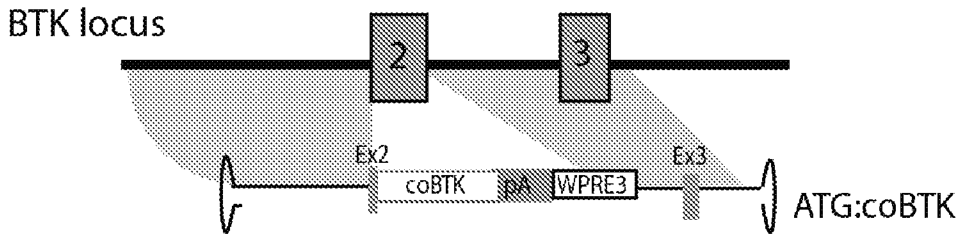
FIG. 8A is a schematic of the rAAV6 donor vector expressing codon optimized BTK cDNA from the endogenous promoter.
Figure 8B:
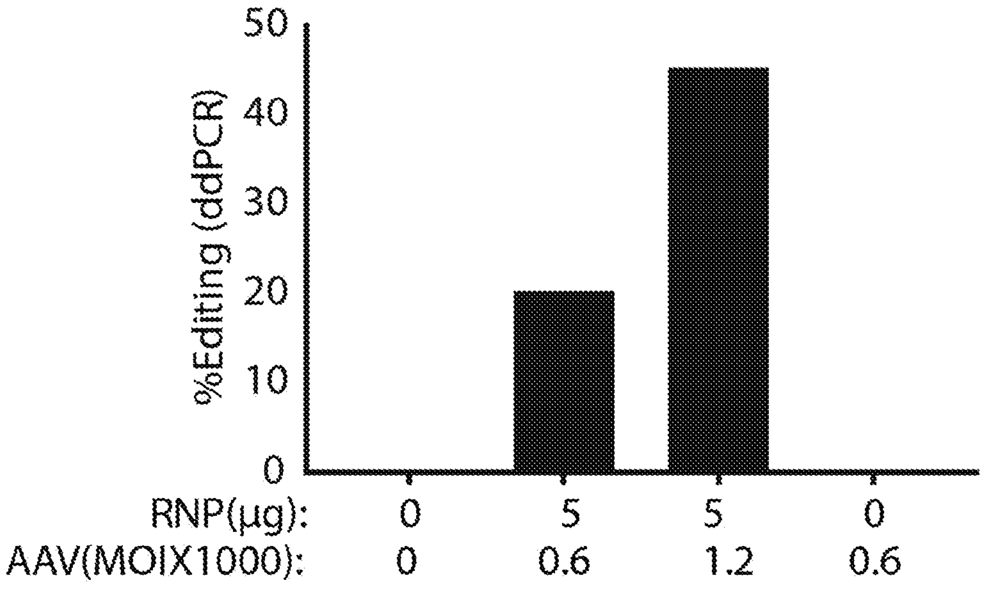
FIG. 8B shows data from a single $CD34^+$ donor demonstrating that ability to introduce the BTK cDNA into the endogenous BTK locus at levels predicted to readily provide clinical benefit in XLA.

FIGS. 8A-8B illustrate HDR editing in CD34$^+$ cells treated with RNPs and a rAAV6 BTK cDNA targeting vector designed to express codon optimized BTK cDNA into the endogenous BTK locus at levels predicted to readily provide clinical benefit in X-linked agammaglobulinemia (XLA).

Results

FIG. 7 shows a comparison of ratio of HDR (homology directed repair) versus NHEJ (non-homologous end joining) in cells edited with TALEN plus AAV or RNP plus AAV. Adult human mobilized CD34+ cells were cultured in SCGM media supplemented with TPO, SCF, FLT3L and IL6 (100 ng/ml) for 48 hours, followed by electroporation using Neon. The cells were transfected with either 0.5 μg of each TALEN monomer or 2 μg of RNP (Cas9: guide ratio of 1:1.2) followed by AAV transduction at a culture volume of 3%. Genomic DNA was extracted from the cultured cells at day 5 and ddPCR performed to determine HDR rates.

To assess editing rates, "in-out" droplet digital PCR was performed with the forward primer binding within the AAV insert and the reverse primer, binding the BTK locus outside the region of homology. A control amplicon of similar size was generated for the CCR5 gene to serve as a control. All reactions were performed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe and 50 ng of genomic DNA. Droplets were analyzed on the QX200 Droplet Digital PCR System (Bio-Rad) using QuantaSoft software (Bio-Rad). Additionally, the region around the cut site was amplified, gel extracted and subjected to ICE (Inference of CRISPR Edits) analysis to determine the NHEJ rates. The ratio of HDR vs NHEJ was plotted on the graph. Colors represent independent CD34$^+$donors. Data are presented as mean±SEM.

A higher HDR: NHEJ ratio is favorable as it means that the cells are primed to repair the cut using HDR instead of mutagenic NHEJ. While higher levels of HDR are achieved with the RNP platform, the HDR: NHEJ ratio is relatively higher for TALEN plus AAV compared to RNP plus AAV delivery.

FIGS. 8A-8B show HDR editing in CD34$^+$ cells treated with RNPs and a rAAV6 BTK cDNA targeting vector designed to express codon optimized BTK cDNA in successfully edited HSC. FIG. 8A is a schematic of the rAAV6 donor vector expressing codon optimized BTK cDNA from the endogenous promoter. Adult human mobilized CD34$^+$ cells were cultured as previously described, followed by electroporation using the Neon instrument. HSC cells were transfected with 5 μg of RNP (Cas9: guide ratio of 1:1.2) followed by AAV transduction at the MOIs of 600 and 1200. Genomic DNA was extracted from the cultured cells at day 5 and a droplet-digital PCR (ddPCR) assay was performed to determine HDR rates.

To assess editing rates, "in-out" droplet digital PCR was performed with the forward primer binding within the AAV insert and the reverse primer, binding the BTK locus outside the region of homology. A control amplicon of similar size was generated for the CCR5 gene to serve as a control. All reactions were performed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe and 50 ng of genomic DNA. Droplets were analyzed on the QX200 Droplet Digital PCR System (Bio-Rad) using QuantaSoft software (Bio-Rad).

In FIG. 8B, data from a single CD34$^+$donor is shown clearly demonstrating that ability to introduce the BTK cDNA into the endogenous BTK locus at levels predicted to readily provide clinical benefit in XLA.

Table 5 provides a list of oligos and probes for determining HDR in CD34$^+$ cells targeted using RNP or TALEN plus AAV.MND.GFP vectors.

TABLE 5

| | | |
|---|---|---|
| BTK RNP/ TALEN_HR forward oligo | GAGCAAAGACCCCAACG AGA | SEQ ID NO: 25 |
| BTK RNP_HR_reverse oligo | AGGTTTTATGTCTCTCG CTCCG | SEQ ID NO: 26 |
| BTK_RNP(GFP) HR probe | GCATGGACGAGCTGTAC AAG | SEQ ID NO: 27 |
| TALEN_HR reverse oligo | ATGGTCAGACCCAGTGG GTG | SEQ ID NO: 28 |
| TALEN_HR Probe | TGACAGGTCCTGGTGCC ACCT | SEQ ID NO: 29 |
| CCR5_control forward oligo | AAAGATTTGCAGAGAGA TGAGT | SEQ ID NO: 30 |
| CCR5_control reverse oligo | GCCAAGCAATGAAGTTT TGT | SEQ ID NO: 31 |
| CCR5_probe | CCTGGGCAACATAGTGT GATC | SEQ ID NO: 32 |

Table 6 provides a list of oligos and probes for determining HDR in CD34⁺ cells targeted using RNPs and ATG-.coBTK expressing AAV vectors. Control CCR5 oligos/probe are the same as for GFP vectors.

TABLE 6

| | | |
|---|---|---|
| BTK (coBTK)_WPRE3 probe | TCCTGGTTAGTTCTTGCCAC | SEQ ID NO: 33 |
| BTKco_HR forward oligo | AGAAACTGCCTGGTGAACGAC | SEQ ID NO: 34 |

TABLE 6-continued

| | | |
|---|---|---|
| BTKco_HR reverse oligo | CCCCATCTCAGACATTGGTC | SEQ ID NO: 35 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A gene editing composition comprising:

a) a Cas protein or a polynucleotide encoding a Cas protein;

b) a guide-RNA (gRNA), wherein the gRNA consists of SEQ ID NO: 11; and c) a repair template comprising a functional BTK gene or fragment thereof encoding a BTK polypeptide that restores normal B cell development.

2. A polynucleotide encoding the gene editing composition of claim 1, or a vector comprising the polynucleotide.

3. The polynucleotide of claim 2, which is an mRNA encoding the gene editing composition or a cDNA encoding the gene editing composition.

4. An isolated cell comprising the gene editing composition of claim 1, or a polynucleotide encoding the gene editing composition, or a vector encoding the polynucleotide.

5. The isolated cell of claim 4, wherein the cell is a hematopoietic cell, or a hematopoietic stem or progenitor cell.

6. The isolated cell of claim 5, wherein the cell is a $CD34^+$ cell or a $CD133^+$ cell.

7. A composition comprising an isolated cell according to claim 4 and a physiologically acceptable carrier.

8. An isolated cell comprising one or more genome modifications introduced by the gene editing composition of claim 1.

* * * * *